US011712271B2

(12) United States Patent
Boehm, Jr. et al.

(10) Patent No.: US 11,712,271 B2
(45) Date of Patent: Aug. 1, 2023

(54) DEVICE AND METHOD TO ESTABLISH STABILIZATION OF THE CERVICAL SPINE WITHOUT IMPLANTATION OF HARDWARE OR VIOLATION OF THE CORTICAL BONE

(71) Applicants: Frank H. Boehm, Jr., New Hartford, NY (US); Todd M. Cramer, North Syracuse, NY (US)

(72) Inventors: Frank H. Boehm, Jr., New Hartford, NY (US); Todd M. Cramer, North Syracuse, NY (US)

( * ) Notice: Subject to any disclaimer, the term of this patent is extended or adjusted under 35 U.S.C. 154(b) by 0 days.

(21) Appl. No.: 16/206,509

(22) Filed: Nov. 30, 2018

(65) Prior Publication Data
US 2020/0170682 A1 Jun. 4, 2020

(51) Int. Cl.
*A61B 17/70* (2006.01)

(52) U.S. Cl.
CPC ................. *A61B 17/7047* (2013.01)

(58) Field of Classification Search
CPC ................................. A61B 17/7047
See application file for complete search history.

(56) References Cited

U.S. PATENT DOCUMENTS

| 1,156,440 | A |   | 10/1915 | Smith |  |
|---|---|---|---|---|---|
| 3,242,922 | A |   | 3/1966 | Thomas |  |
| 4,570,618 | A |   | 2/1986 | Wu |  |
| 4,611,582 | A | * | 9/1986 | Duff | ................... A61B 17/7047 606/258 |
| 5,374,267 | A |   | 12/1994 | Siegal |  |
| 6,132,464 | A |   | 10/2000 | Martin |  |
| 6,589,243 | B1 |   | 7/2003 | Viart et al. |  |
| 8,034,079 | B2 |   | 10/2011 | Bruneau et al. |  |
| 8,361,117 | B2 | * | 1/2013 | Michielli | ............ A61B 17/7049 606/253 |
| 8,419,771 | B2 | * | 4/2013 | Poirier | ............... A61B 17/7052 606/250 |
| 8,801,757 | B2 |   | 8/2014 | Abdou |  |
| 2002/0151895 | A1 |   | 10/2002 | Soboleski et al. |  |

(Continued)

FOREIGN PATENT DOCUMENTS

| CN | 205458992 | 8/2016 |
|---|---|---|
| JP | 3608943 | 1/2005 |

OTHER PUBLICATIONS

ISA/US; International Search Report for International Application PCT/US16/13030; dated Mar. 17, 2016; 10 pgs.

(Continued)

*Primary Examiner* — Tessa M Matthews
(74) *Attorney, Agent, or Firm* — Christopher E. Blank; Schmeiser, Olsen & Watts, LLP

(57) ABSTRACT

A system of devices and methods for use by which one or more target motion segments of the cervical spine are stabilized without any violation of the cortical bone of the target vertebrae. The devices are brought against strategic aspects of these vertebrae, thus permitting the disclosed inventions to achieve secure control of each vertebra. Connecting elements then stabilize the constructs. Preferred and alternative embodiments of the invention are disclosed, along with methods of implantation, and adjunct devices used in the implantation of the disclosed invention.

7 Claims, 65 Drawing Sheets

(56) References Cited

U.S. PATENT DOCUMENTS

| | | |
|---|---|---|
| 2005/0228377 A1* | 10/2005 | Chao .................. A61B 17/7052 |
| | | 606/252 |
| 2006/0241591 A1 | 10/2006 | Biscup et al. |
| 2006/0241614 A1 | 10/2006 | Bruneau et al. |
| 2008/0103512 A1 | 5/2008 | Gately |
| 2011/0307011 A1 | 12/2011 | Moskowitz et al. |
| 2013/0231704 A1 | 9/2013 | Larroque-Lahitette |
| 2016/0228154 A1* | 8/2016 | Mickiewicz ....... A61B 17/7047 |
| 2017/0319238 A1 | 11/2017 | Boehm, Jr. |
| 2018/0289403 A1 | 10/2018 | Shoshtaev |
| 2018/0360501 A1 | 12/2018 | Lasswell et al. |

OTHER PUBLICATIONS

ISA/US; International Search Report for International Application PCT/US20/27936; dated Jul. 17, 2020; 11 pgs.
ISA/US; International Search Report for International Application PCT/US19/63751; dated Feb. 19, 2020; 8 pgs.
EPO; Extended European Search Report dated Jul. 7, 2022 in related European Application 19891583.7.

* cited by examiner

DEVICE AND METHOD TO ESTABLISH STABILIZATION OF THE CERVICAL SPINE WITHOUT IMPLANTATION OF HARDWARE OR VIOLATION OF THE CORTICAL BONE

CROSS-REFERENCE TO RELATED APPLICATIONS

The disclosure of this patent application relates to the disclosure of U.S. patent application Ser. No. 15/646,615 filed Jul. 11, 2017, the entirety of which is incorporated herein by reference.

BACKGROUND OF THE INVENTION

The point in history when ancient physicians first recognized the cervical spine as a site of significant human pathology has been lost in the mists of time. The Smith Papyrus demonstrates that Egyptian physicians during the period of the Middle Kingdom were aware of pathology of the neck, and there is evidence to suggest that this document may have been copied from works of physicians from even earlier civilizations.

Today, cervical spine pain and related symptoms are among the most common reasons for patients to visit health care providers, as well as one of the most common sites for elective surgery upon the spinal column. Furthermore, these are very frequently the major complaints following motor vehicle accidents and other domestic I civilian trauma, and is probably the leading cause of litigation in that scenario. Cervical spine pain is a common complaint associated with Workers' Compensation injuries, leading to billions of dollars in medical care, disability benefits, and lost productivity. It cannot be overlooked, either, that such injuries plague military personnel and in particular pilots that operate supersonic aircraft; in this scenario, it has been often commented that for such pilots, it is "only a matter of time" until they experience CS-6 degeneration. Clearly, this is a very major problem in the United States, as well as most technologically advanced countries going forward into the New Millennium.

This contention is also supported by the fact that there are over 50,000 anterior cervical fusions performed every year in the United States alone. Primary posterior procedures may add up to 25, 000 additional cases. Moreover, millions of patients suffer with chronic neck pain. This great prevalence has also spawned a vast number of alternative therapies to speak to this large patient population.

There are many theories as to the genesis of chronic neck I spine pain, but one of the more well-established hypotheses is that such "axial" pain represents an element of abnormal motion between two or more vertebrae, the so-called syndrome of "microinstability." Furthermore, it is speaking to this issue of "Microinstability" that theoretically serves as the primary indication for spinal fusion; if one believes that the symptoms are the result of excessive motion then, obviously, successful fusion of the segment and hence eliminating all movement should resolve the issues. Unfortunately, for reasons that are not yet fully elucidated, this does not always resolve to be true.

In order to better understand the relationship between spinal biodynamics and axial pain, scientist and physicians studying the spine have developed a paradigm referred to as the "motion segment." This refers to a unit comprised of any two adjacent vertebrae, along with their associated intervertebral disc, facet joints, associated ligaments, tendons, muscles as well as neural elements.

Given that paradigm and recognizing the special anatomy of the first two cervical vertebrae, it can be understood that this paradigm can be utilized to comprehend pathologic states of the cervical spine. What can also be appreciated is how the device disclosed herein can be beneficial from both a diagnostic as well as therapeutic perspective. This can be further enhanced by a review of spinal instrumentation that has been utilized in the cervical spine.

Instrumentation for enhancement of cervical spine fusion surgery has evolved dramatically over the past three decades. Interestingly enough, instrumentation for the treatment of the cervical spine was introduced by Hadra in 1891, at which time he wired the spinous processes of C6 to C7; however, although he did not supplement this with fusion graft, this procedure was reported to be extremely successful. At a later time, he (Hadra) introduced modifications of this technique for use in the treatment of Pott's disease.

Spinal fusion proper (again for the treatment of Pott's disease) was introduced by Hibbs in 1911, and in the century that has passed since then, this procedure has established itself as one of the most commonly performed elective surgeries in the United States, as well as throughout the world. Although Hibbs procedure was initially introduced for treatment of the lumbar spine, eventually fusion was introduced for the cervical spine as well.

By 1942, the combination of fusion with posterior spinal instrumentation evolved. That year, Rogers introduced the technique of passing wires through holes drilled in the target spinous processes, and supplementing this with bone graft from the iliac crest. This technique was further modified by Whitehill, Benzel, and others.

Bohlman introduced a technique by which not only were the spinous processes wired, but elongated bone grafts from the iliac crest were wired to the lateral masses. Facet fixation was first introduced by Callahan in 1977, proposing that holes be drilled through the facets and wires passed into them ultimately stabilizing the construct. This was largely utilized in the lumbar spine, although some cases of cervical facet fusion were reported.

Cahill, in 1983, introduced a variation of Callahan's teachings which actually combined earlier techniques with facet wiring. He passed wires around the spinous process of the caudal vertebra of the target motion segment, pursuant of the classic technique as described by Hadra. The other ends of these wires were passed through holes drilled through the lateral masses, as described by Callahan.

In his landmark work starting in the 1950's, Harrington proposed a system of hooks which were passed under the edges of the laminae and then connected to long rods. This system was primarily introduced to correct scoliotic curvatures, but was responsible for the introduction of sublaminar hooks, which are now commonly used in a variety of systems used in all segments of the spine, including the cervical spine. The inventive process disclosed herein utilizes a sublaminar component similar to the hook method taught by Harrington.

Another method for posterior stabilization was introduced by surgeons at the University of Halifax in the mid 1980's, teaching that a pair of curved metal plates could be passed around the superior edges of the laminae of the cranial vertebra of a target motion segment, with a pair of "mirror image" curved plates being disposed around the inferior edges of the laminae of the caudal vertebra. The trailing ends of these plates are configured to be secured to each other by screws, which also provided adequate compression of the plates against the bone. Although this technique, when reduced to practice, enjoyed a brief period of popularity, they are rarely if ever used at this point, and are essentially of historic interest only.

Lateral mass screws were introduced by Roy—Camille in the early 1980's, and have ostensibly become, in one form or the other, the posterior cervical stabilization method of choice in 2015. Various systems have been introduced which allow for occipito-cervical stabilization, cervicothoracic stabilization, and even occipito-cervico-thoracic systems. This surgery requires an extensive exposure and cannot be performed using a minimally invasive technique; such MIS techniques have become increasingly desirable in today's healthcare environment for many reasons, particularly the reduced complications, shorter periods of hospitalization, and reduced need for postoperative pain management. Furthermore, there is a need for extremely precise location of the screws in order for them to be accurate, effective, as well as to minimize the chances of significant injury to the nerve roots or vertebral artery. The latter is a rare but extremely serious complication and has been known to result in vertebral artery dissection, stroke and even infarct of the spinal cord.

Accordingly, and for all the foregoing reasons, a substantial need exists for a device which can stabilize the cervical spine utilizing a minimally invasive procedure, and without violating the cortical bone or causing substantial injury to the periosteum. This is important, as many recent studies have demonstrated that injury of the bone, or annulus fibrosis can accelerate the degenerative process. Such a device would, by inference and implication, have to be fully reversible not only in terms of implantation, but also terms of having no substantial impact upon the anatomy and function of the target motion segment. This device, as provided herein, would be unique, useful, novel and non-obvious.

BRIEF DESCRIPTION OF THE INVENTION

The invention relates to the general field of spinal surgery, and specifically to a device and method for use by which a unique, useful, novel and non-obvious stabilizing clamp is secured bilaterally to the posterior bony surfaces of at least two adjacent cervical vertebrae, and once positioned, connecting elements are secured to the cranial and caudal clamps bilaterally, thus eliminating any motion of the target motion segment.

This brief description of the invention is intended to only provide an overview of the subject matter disclosed herein in accordance with one or more illustrative embodiments. It is anticipated that these illustrative embodiments will ultimately be in accordance with claims that will be disclosed with a Non-Provisional Application which will ultimately be submitted pursuant to this application. This brief description is provided to introduce an illustrative selection of concepts in a simplified form that are further described below in the detailed description. This brief description is not intended to identify key features or essential features of the subject matter, no is intended to be used as an aid in determining the scope of the subject matter. The subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention, and are therefore not to be considered limiting of its scope, for the scope of the invention encompasses other equally effective embodiments. The drawings are not necessarily to scale; emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings, in which:

FIG. 33 portrays the coupling of two laminar anchors in the alternative embodiment in FIG. 31.

FIG. 36 B demonstrates a multilevel embodiment of the alternative configuration provided in FIG. 36 A.

FIG. 39 B demonstrates an assembled multilevel construct of the same.

SUMMARY OF THE INVENTION

Figure 1:
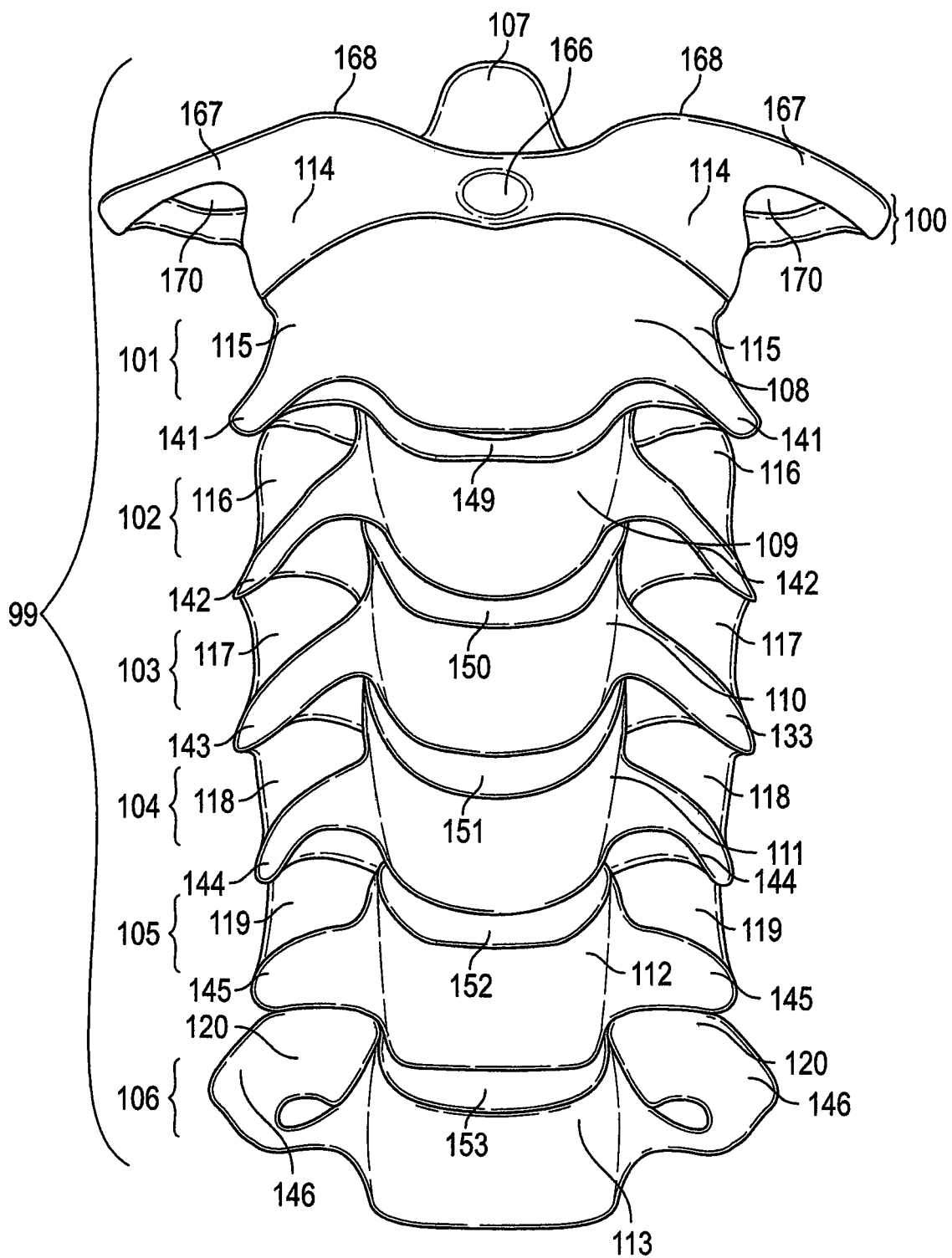
FIG. 1 shows an anterior view of the osseous cervical spine.

This written description uses examples to disclose the invention, including the best mode and also to enable any person skilled in the art to practice the invention, including making and using any devices or systems and performing any incorporated methods. The patentable scope of the invention is currently defined by the description of the invention and will be further defined by claims.

The principal object of the invention is to provide a unique, useful, novel and nonobvious device and method for use by which the device stabilizes the posterior aspect of a target cervical spinal motion segment, immobilizing the segment. This device shall hereinafter be known as the Cervical Minimally Invasive System (CMIS), as it is designed to be implanted using a minimally invasive surgical technique.

In the preferred embodiment, the CMIS shall be fabricated from surgical grade titanium. Alternatively, this CMIS can be fabricated from surgical grade stainless steel, or of alloys of any metal, including but not limited to cobalt, nickel, chromium, molybdenum, or of other materials including Nitinol, carbon fiber, polyesters or polyamides, ceramic, PEEK, organic materials such as bone, or any other material known to or proven to be acceptable to the art.

The preferred embodiment is comprised of anchors which are sequentially secured to the lateral laminae of one or more cervical target motion segments; connecting elements then couple these anchors to each other, stabilizing the construct and eliminating any micromotion. In the preferred embodiment and all alternative embodiments, these constructs would typically be secured bilaterally. Additionally, in all embodiments, the craniocaudal dimensions of the target motion segments can be adjusted by applying distraction or compression along the connecting elements.

In the preferred embodiment, these laminar anchors secure to the inferior or caudal aspect of the lateral lamina. As reviewed in the "Detailed Description of the Drawings" section below, these laminar anchors are composed of a sublaminar jaw and a dorsal jaw. The sublaminar jaw is provided with a thin plate—like leading end, which is designed to be insinuated beneath a target lamina, dorsal to the ligamentum flavum, and occupying minimal space so as to not threaten the spinal cord or other intra-canalicular neurologic structures. The dorsal jaw is brought against the posterior aspect of the target lamina. These jaws are irreversibly coupled to an axle which is positioned at the trailing end of the anchor, orthogonal to the long axis of the anchor; as an indirect result of this coupling to the axle, the jaws are effectively coupled to each other. This axle is part of the actuator that draws the jaws towards each other thus securing to the lamina. Similarly, if removal is desired, the jaws can be released, and the anchor removed from the bone.

These jaws are substantially hemi-ovoid in configuration, as viewed from the side; furthermore, the leading end of each jaw may be provided with a limited array of small, non-biting teeth which are configured to not penetrate the cortical bone, but merely provide increased friction against the target bony surface. Once the jaws are in position, a securing screw contained within the articulating mechanism at the trailing end of the anchor is tightened. This serves as the actuator compelling the two jaws towards each other. The anchors are then coupled to each other with a connecting element. In the preferred embodiment, the securing screw which causes the jaws to be drawn together is provided with a leading end, which passes through the anterior jaw, a shaft that bridges both jaws, and a trailing end which is actuated by the surgeon. The trailing most end is provided with a vertical extension which is then continuous with a horizontal bar.

In the preferred embodiment, the connecting element is a rod-like embodiment in which the leading end is provided with a flattened area which in turn has a central elongated aperture. The leading end is continuous with a central shaft-like portion, which, in turn, is continuous with a trailing end which is provided with a saddle that is secured to the dorsal jaw. In the preferred and other embodiments, the leading end of the connecting element is disposed over this horizontal bar on the trailing end of the screw of the cranial anchor. The configuration of the connecting element, principally the elongated configuration of the central aperture at the leading end of the connecting element allows for either distraction or compression of the target motion segment.

IMPLANTATION OF THE INVENTION

The invention can be implanted through a minimally-invasive posterior approach, utilizing intraoperative fluoroscopy or some other intra-operative imaging technique I computer navigation in order to guide this surgical approach. Meticulous attention to these images is required in order to be certain that the correct target levels are identified and stabilized.

After achieving adequate anesthesia (general I regional I local) a limited incision is accomplished over the lateral target lamina. The site of the incision can be randomly chosen; alternatively, it can be dictated by a unique template system described in FIGS. 9 AlB and 10. The incision itself can be achieved with the use of a standard scalpel; alternatively, a unique, useful, novel and non-obvious skin incision device.

A unique, double-edged dissection device is then utilized to divide the muscles using along the natural planes. Upon identifying the caudal aspects of the target laminae, additional sub-periosteal dissection is completed along the site on the lamina where the posterior jaw of the laminar anchor is going to be fastened. This is illustrated below in FIGS. 13 A-E.

It is common in patients suffering from degenerative disease to demonstrate loss of intervertebral height. The relevance of this observation to this invention is that this loss of height typically results in increased "shingling," of the laminae, which will reduce the access to the caudal edge of the lamina.

This can be ameliorated by distracting the target motion segment. As this is a posterior approach, this is best addressed by distracting the two spinous processes away from each other. This can be achieved with the use of a standard laminar spreader.

Figure 14:
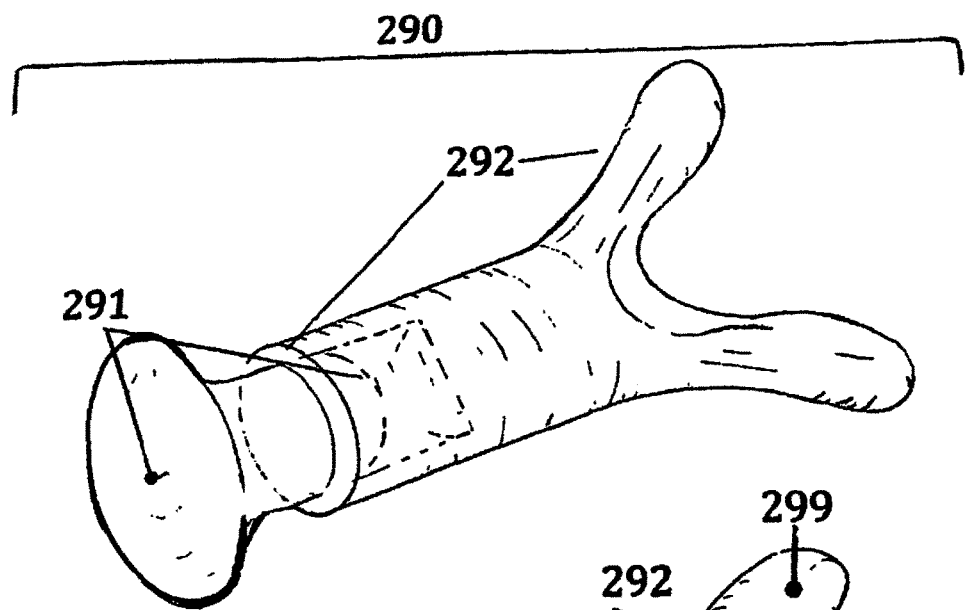
FIGS. 14 A/B examine elevational and exploded views of the device for distracting the vertebrae comprising the target motion segment from each other.
Figure 14:
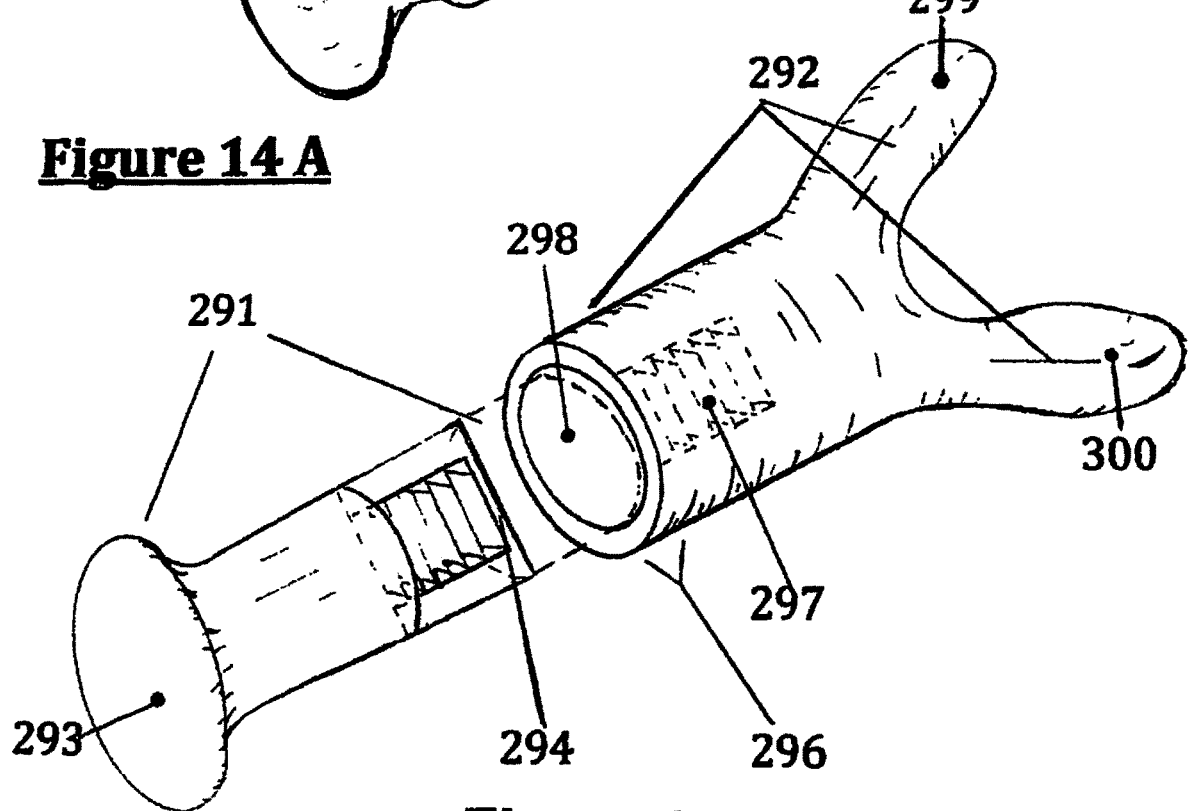

Alternatively, a spinal motion segment distractor is provided as part of the system of devices to implant the invention. This device is interpositioned between the spinous processes and then expanded, creating a more optimal operative field. This is demonstrated in FIGS. 14 A/B, as well as 15 and 16 A-D.

Although an MIS approach is being utilized, optimal exposure is still desirable. To this end, an MIS retractor specifically designed for a cervical MIS procedure has been provided. The reader is again referred to FIGS. 17 A-HI.

A foot-plated dissector then creates a plane between the ligamentum flavum and the underside of the lamina. An implantation instrument is introduced, the leading end of which reversibly couples with the laminar anchor. This instrument initially guides the cranial laminar anchor onto the target lamina, tightening the securing screw thus securing the anchor to the lamina. This procedure is repeated at the caudal level, and the leading end of the connecting element is then passed over the horizontal bar at the trailing end of the screw of the cranial anchor. The screw is rotated approximately one-quarter turn, locking the connecting element in place. In virtually every instance, the cervical spine would be stabilized bilaterally. The invention is designed to stabilize one or more target cervical motion segments, with levels being added using the same technique to couple the additional levels.

ALTERNATIVE EMBODIMENTS

One can envision multiple alternative embodiments of the invention; the most obvious of these are disclosed herein. Those skilled in and familiar with the art may envision and offer other embodiments; such embodiments are also, by reference, included within the spirit and scope of this invention.

In the preferred embodiment, the connecting element is secured to the dorsal aspect of the proposed caudal anchor at the time of manufacture. In the first set of alternative embodiments, there are variations in the manner by which the connecting element is coupled to the laminar anchors. One challenge that the system must overcome is to create seamless coupling of the anchors from level to level, accommodating the slight variations in the angles and heights of the coupling points created by the slight differences in the vertebrae from level to level.

In one such alternative embodiment, the trailing end of the connecting element is substantially identical to the leading end so that there is an elongated aperture provided to the trailing end as well. This can be disposed over the horizontal bar of the caudal laminar anchor in a manner similar to the cranial anchor; both horizontal bars then lock down the leading and trailing ends of the connecting element. Distraction or compression-in any such embodiment can be accomplished owing to the elongated apertures at the ends of the connecting element. In such an embodiment, the rod can either be "pre-loaded," onto one of the anchors at the time of implant; optionally, the connecting element can be a completely free and separated element which is added to the construct.

A further variation of this embodiment also utilizes the connecting element with apertures on both ends, without the horizontal bars.

Accordingly, the ends of the connecting element in this embodiment are positioned under the heads of the securing screws of both anchors. As the screws are actuated against the target laminae, the connecting element is simultaneously secured in place.

An embodiment can be conceived in which an extension arises from the dorsal surface of [preferably] the caudal anchor; this is continuous with a sphere/hemisphere which is irreversibly coupled with the leading end of a cradle. The geometry of this coupling confers polyaxial movement on the cradle, which will critically dictate the ability of this cradle to accommodate slight variances in the alignment of the laminar anchors from level to level.

A rod is positioned within the cradle which is provided with a leading end, an extended shaft, and a trailing end. The leading end is substantially identical to that in the preferred embodiment, having a flattened area with a central aperture. This is continuous with the solid central shaft which then connects to the trailing end, which is slightly enlarged so that it cannot be advanced past the cradle. In the primary I non-deployed position, the connecting element is positioned such that the majority of the rod has not been disposed through the cradle. A securing screw is positioned within the cradle to maintain the rod in its initial position as well as to lock the rod in final position once deployed.

Once both anchors are secured to their respective laminae, an anchor implantation instrument engages the trailing end of the rod, pushing the rod until the leading end is captured by the counterpart implantation instrument stabilizing the [cranial] anchor. The aperture in the leading end of the rod is then secured to the trailing end of the screw by disposing the aperture over the horizontal bar, locking the construct in place. A variation of this embodiment simply provides cradles to both cradles and a rod that stabilizes the construct.

Other, more complex embodiments can also be envisioned. In one such embodiment, the illustrated below, there is a modification of the laminar anchors which includes a C-clamp embodiment which is which is irreversibly coupled to and continuous with the dorsal aspect of the dorsal jaw of the anchor. This clamp is tightened by a threaded bolt or similar mechanism, securing a rod within it. The leading end of this rod is provided with a round aperture that is disposed over a threaded dorsal extension which, in turn, arises from the trailing end of the securing screw at the [presumably cranial] adjacent level. This embodiment can be extended for multiple levels by repeating the segmental coupling mechanism described herein.

An alternative of this embodiment utilizes a single rod embodiment to couple to laminar anchors at each level, anticipating that a clamp similar to that described in the paragraph above would be used at each level.

In another alternative embodiment, the rod is provided with a spherical trailing end which is encased within a collared socket, providing the rod with a limited range of motion and thus allowing the rod to accommodate for misalignment between the two adjacent vertebrae which are to be stabilized. This is ideally positioned at the cranial end of the caudal anchor, with a receiving cradle provided to the caudal end of the cranial anchor. In the primary, non-deployed position, the rod is directed posteriorly; once both anchors are secured to the laminae, the rod is rotated into the cradle and then secured in place with a locking bolt I nut.

Another alternative embodiment discloses a threaded post arising from a point along the dorsal aspect of each laminar anchor. The anchors are then coupled to each other by the use of a connecting rod or plate-like element which can be adjusted in the craniocaudal direction. This adjustment permits the length of the rod or plate to be slightly adjusted prior to being locked into position.

Yet another embodiment of the connecting element can be anticipated in which an extension arises from each anchor and is directed either caudally or cranially, but only of a sufficient length to span part of the motion segment. In this embodiment, these incomplete bridging connectors are then coupled in the midportion between the two anchors. In such a scheme, anchors which are serving as middle anchors in a multilevel construct would be provided with coupling arms which would directed in both cranial and caudal directions.

In a variation of the foregoing, the anchors are each provided with both a rod-like extension as well as a receiving component to couple with the rod-like extension from another level. It would be anticipated that in this embodiment, said rod-like extension would be directed cranially, with the receiving component on the caudal aspect of the anchor. However, an arrangement in which the extension is directed caudally with the appropriate repositioning of the receiving port is also within the spirit and scope of this application. It is obvious that a uniform application of like embodiments would be necessary in order to achieve the desired stabilization. Such an embodiment may be more difficult to secure in place because this embodiment does not account for variations from level to level.

Still other embodiments achieving the same goals and objectives can be conceived and are within the spirit and scope of the invention. In one such embodiment, leading and trailing elements of a connecting element are each provided with a shaft terminating in an open-ended configuration. These shafts are then conjoined in the middle by a coupling element which accommodates differences in position between the vertebrae. The open-ended configurations are passed around the shafts of the screws prior to locking the anchors in place, after which the ends of the connecting element are secured between the dorsal surface of the anchor and the head of the screw.

In another variation, anchors are provided which are configured to be secured to cranial aspect of the lamina as well as the caudal. In such an embodiment, the arrangement and order of placement of these anchors relates to the surgical objectives in terms of the final craniocaudal dimension. Therefore, if the goal of surgery is distraction of the target motion segment[s], an anchor is secured to the caudal aspect of the cranial lamina, whilst the other anchor is secured to the cranial aspect of the caudal lamina. Such a configuration would favor distraction.

Conversely, if the surgeon mandates compression, then placing an anchor on the cranial aspect of the cranial lamina while securing the other anchor to the caudal aspect of the caudal lamina would be the favorable configuration. In both of these configurations, the coupling of these anchors is achieved by any number of the connecting elements illuminated in the foregoing disclosure.

A combination of the embodiments disclosed above can be considered. For instance, one configuration would be a connecting element which is provided with an aperture at one end and an open-ended embodiment at the other. Such an embodiment disposes the securing screw of one anchor through the aperture, which is then locked; the open-ended configuration is positioned under the trailing end of the screw of the adjacent anchor prior to complete tightening of the screws.

It is, of course, understood that combinations of those various embodiments presented herein are conceivable and likely to be envisioned I anticipated by those skilled in the art. All such embodiments and variations, and derivations therefrom are all included within the spirit and scope of the invention.

DETAILED DESCRIPTION OF THE DRAWINGS

The invention will be best understood if the reader is provided with a fundamental understanding of the pertinent osseous anatomy, and the relationships of various landmarks of the osseous anatomy to key soft tissue structures of the spine. These images are representations of the bony cervical spine, as the object of the invention is to secure to the target vertebra. This, however, recognizes that critical neural and soft tissue structures have not been included in these drawings and that despite their exclusion, these structures must be accounted for within the process of implantation of the invention. Although these soft tissue structures (with the exception of the intervertebral discs) are not illustrated herein, the images will, nevertheless, sufficiently demonstrate the relationships of critical soft tissues such as the spinal cord and nerves to the bony anatomy. When relevant, these structures will be referred to by name in these initial images.

The landmarks demonstrated on these images are crucial in implanting the CMIS. It is important to recognize that the cervical spine is the most common site for anatomic anomalies within the spinal column. Such anomalies must be identified and taken into account when surgery using the CMIS is planned. It is imperative to recognize that in certain instances such anomalies, once identified, could represent a relative I absolute contraindication to the use of the CMIS. Also, these images do not include musculotendinous, vascular, or neurologic structures, all of which could be critical in terms of the indications or contraindications of the use of this device.

Therefore, turning to the anterior view of the osseous cervical spine 99 in FIG. 1, the seven bones, or vertebrae, named I numbered by convention as C1-C7 can be seen. For the illustrative purposes of this application, these will bear the numbers 100-106 corresponding to C1 100-C7 106. The unique anatomy of the C1-C2 100-101 complex can be, in part, appreciated in this view, and in association with the other views can be more completely understood. It is noted that unlike the other cervical vertebrae, C1 does not have an expanded anterior vertebral body. Moreover, an extension from the C2 vertebra, the Odontoid Process 107 (also known as the Dens), can be seen extending above the top of the anterior arch 166 of C1 100. The mechanism created by this unusual anatomic arrangement is best understood in the lateral and posterior views, and is more completely elucidated in FIGS. 2 and 3 below. In addition, one also notes the bilateral transverse processes of C1 167, which provided with the foramina transversaria of C1 170, through which the vertebral artery is transmitted. The course of this important vascular structure is again best seen in FIG. 3. The transverse processes 167 are then continuous with the superior facets 168, which are better seen in the posterior view I FIG. 3 below, and which articulate with the Condyles of the Occipital bone to create the Craniocervical junction (not demonstrated). This view demonstrates other features of the cervical spine, including the bilateral lateral masses of C1 114 through C7 120, and the bilateral transverse processes of C2 141, C3 142, C4 143, C5 144, C6 145 and C7 146. These transverse processes are provided with grooves which are best seen in the transaxial view in FIG. 4, these grooves configured to transmit the nerve roots exiting the central nervous system and being directed to the upper extremities. Another prominent feature which is best seen in this perspective are the anterior aspects of the intervertebral disc joints, with C2-3 (there is no C1-C2 disc joint) being enumerated as 149 and the C6-C7 space being enumerated as 153. The disc joints are obviously soft tissues structures but are included in these views because of the visual continuity they provide, and because these structures are critically important as these are a major site of degenerative disease.

Figure 2:
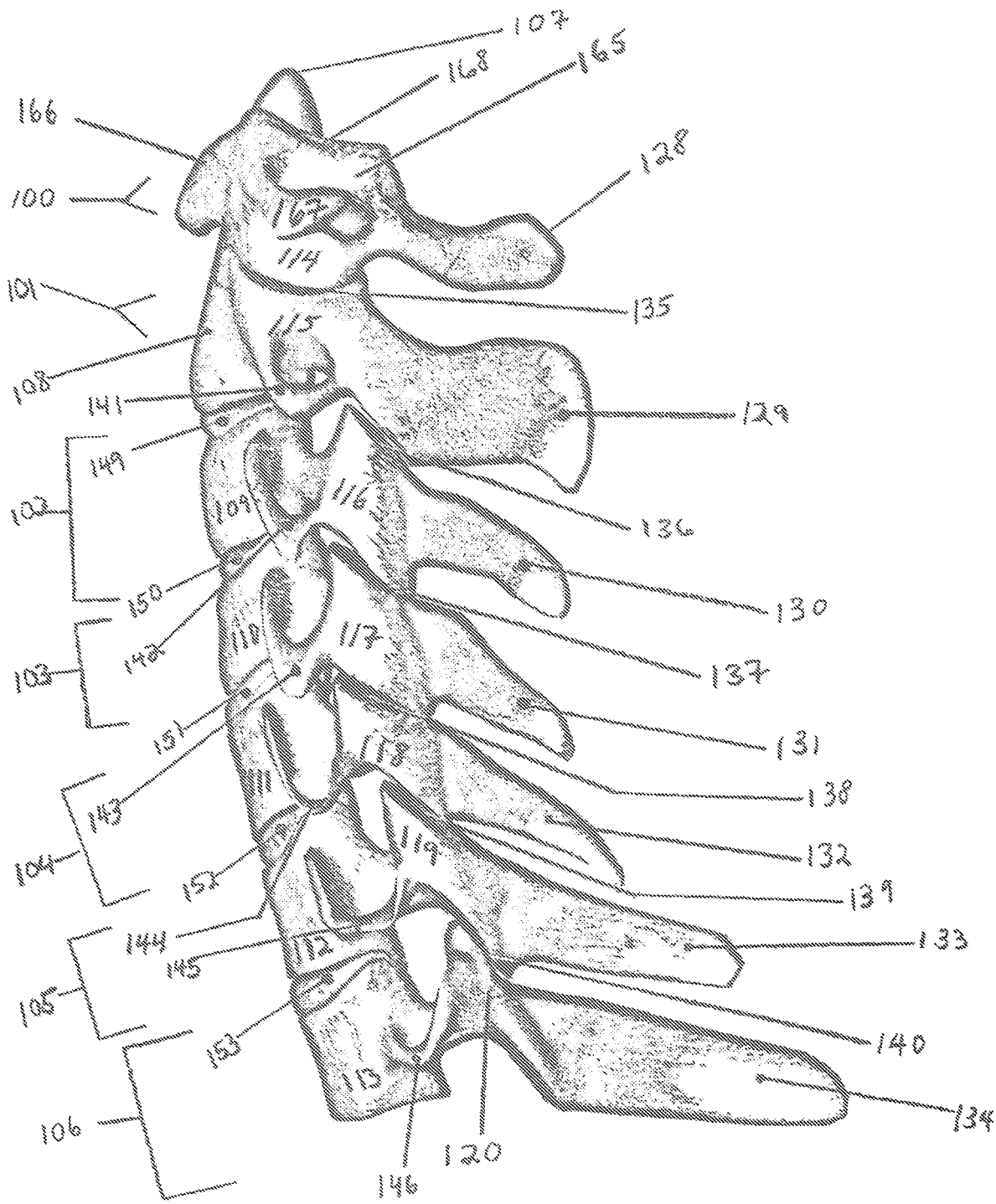
FIG. 2 is a right lateral view of the osseous cervical spine.

FIG. 2 is a right lateral view of the skeletonized cervical spine demonstrating additional features of the anatomy. It is to be recalled that this image is only demonstrating the right sided structures in the instances where bilaterality is present. In particular, one notes the curvature of the spine; this illustration shows an idealized curve, referred to as cervical lordosis, in which the cervical spine arches anteriorly between C1 and C7 with the point of maximum eccentricity at C4-5. Loss of this normal curvature, or, even worse, reversal of the curvature with the spine bending posteriorly—a condition known as "kyphosis," are components of pathologies that commonly affect the spine, and surgeons often will attempt to restore this curvature and in that way restore the "balance," of the cervical spine. Also seen well in this view is the expanded anterior vertebral body, which is present in all but the first cervical vertebra C1 100. This vertebra is more poetically known as the Atlas honoring the protagonist of the Greek Myth who holds up the world; in an analogous fashion, C1 holds up the "globe" of the head. In the embryonic stage, the C1 vertebral body is separated from the remainder of its bony ring and migrates caudally to join the top of C2 101 to become the Odontoid Process 107. The C2 101 is also, and actually more commonly known as the Axis, or the point around which the Atlas, and its "passenger," the head, pivot; the Odontoid Process 107 principally constitutes that bony pivot point. This provides the healthy individual with the rotational ability of the head on the neck. The vertebral bodies 108-113 can be seen, as well as the spinous process 128-134. It is further noted that the at each level, the facet joints 135-140 represent the posterior articulation of the vertebrae with each other; it should be recognized that the superior facets of C1 168 articulate with the occipital condyles, thus contributing to the occipital-cervical junction, also referred to widely as the craniocervical junction (not illustrated.) It is further understood that the inferior aspect of the C7 106 contributes to the cervicothoracic junction (also not illustrated). Additionally, the transverse processes 141-146 are seen projecting anterolaterally at C2-C7. In discussing FIG. 1 above, it has been mentioned that these transverse processes transmit the cervical nerve roots from the spinal cord, which is found in the central canal created by the anatomic arrangement of the vertebrae.

Figure 3:
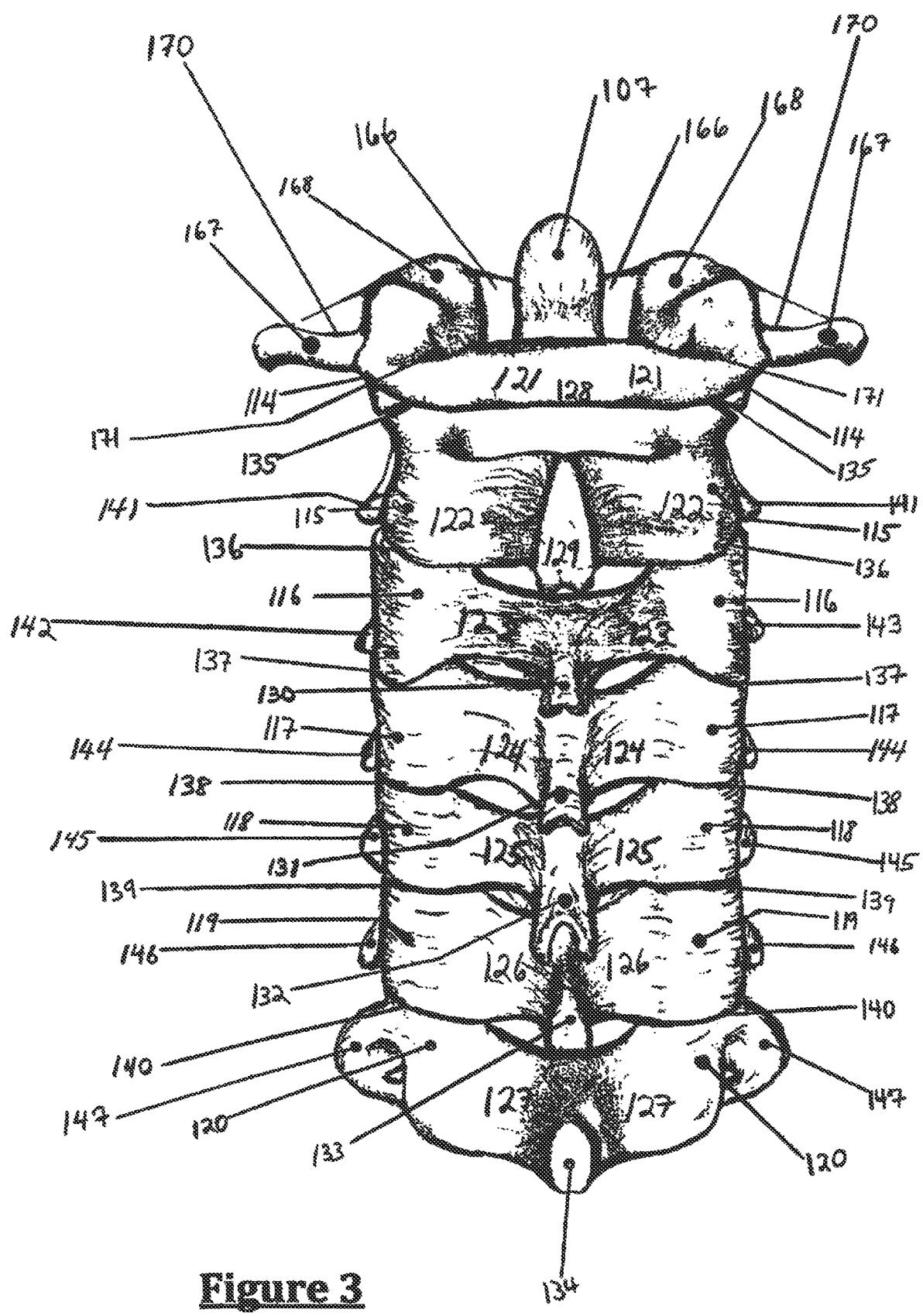
FIG. 3 show a posterior view of the osseous cervical vertebra.

Further details are seen in FIG. 3, which is a posterior view of the osseous cervical spine 99. This Figure is important to note, as the pertinent anatomy for implantation of the CMIS is noted on this image. The first cervical vertebra, C1 100 and the second cervical vertebra C2 101, as illustrated above, are unique in their anatomic configuration. This has already been viewed from an anterior as well as a lateral perspective and discussed thereto, and the uniquely situated anatomy can be further appreciated from this perspective. However, in this image, one can appreciate more completely the relationship of the Odontoid Process 107 to the posterior aspect of the anterior arch 166 of C1 100. Furthermore, one can better appreciate the configuration of the bilateral superior facet joints 168 of C1 100, and the position of the foramina transversaria 170 within the transverse processes 167. of C1. The vertebral arteries, critical to the circulation which irrigates the brainstem and cerebellum, pass through these foramina. Upon doing so, the arteries are directed posteriorly and then pass through a groove 171 along the superior edge of the C1 lamina 121 bilaterally before passing through the dura and onto their critical intracranial functions. The large spinous process 129 and laminae 122 of C2 are important landmarks for determining issues such as placement of incisions during cervical surgery. The remainder of the cervical vertebrae C3-C7 102-106 are largely similar in morphology in this view, including the spinous processes 130-134, laminae 123-127, the lateral masses 114-120, and the bilateral facet joints 135-140. One recognizes that the laminae 123-127 continue from the base of the spinous processes 130-134, at which point the laminae 123-127 are quite steep in the A-P dimension, but become more horizontal in their lateral aspects, just prior to continuing laterally and transitioning into the lateral masses 114-120. At the transition point, it is noted, that the lateral masses 114-120 overhang each other (referred to as "shingling," refer to FIGS. 14-16) which would make it most difficult to insert the laminar anchor. Therefore, in implanting the CMIS, the transition points of the laminae 123-127, such as the bilateral lateral C4 124 and CS 125 laminae are ideal for attachment of the CMIS 1.

Figure 4:
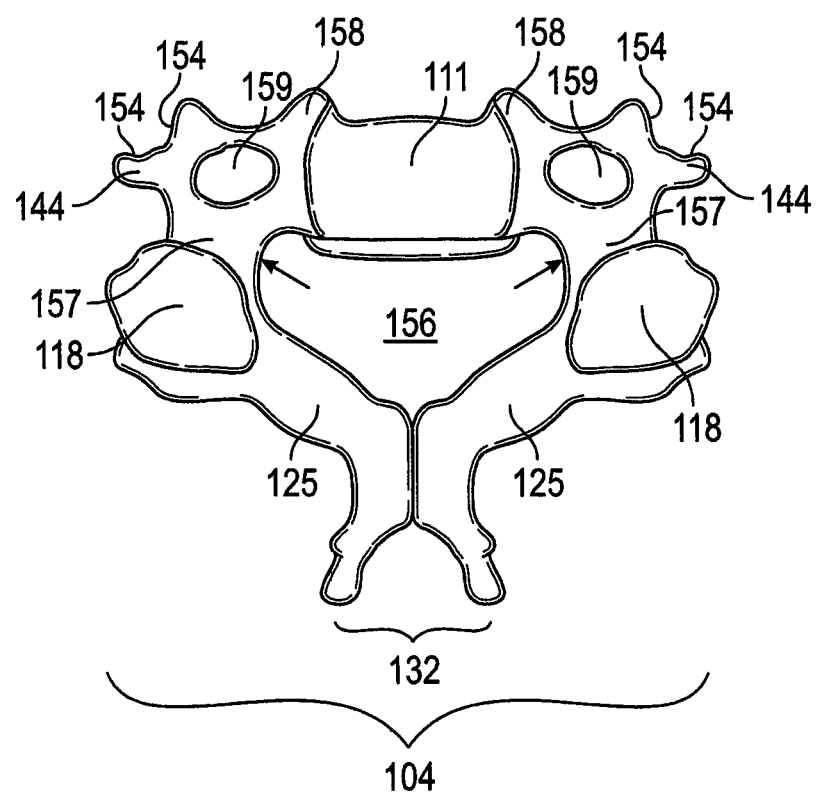
FIG. 4 reveals a transaxial (top) view of a typical cervical vertebra.

FIG. 4, a transaxial view of a "typical" cervical vertebra (this would be very similar from C3 to C6), as viewed from the top perspective, allows the reader to further appreciate the relevant bony morphology as well its relationship to critical soft tissue structures. The C5 vertebra 104 is illustrated in FIG. 4, but the landmarks described are understood to reflect the anatomy of any of the C3-C6 vertebrae, and with little modification, C7 as well. Again, for orientation purposes, the patient's front is at the top of the page, and the back is at the bottom. The patient's right side would be located on the viewer's right side. The expanded vertebral body 111 can be recognized conceptually as the anterior stabilizing component. On the lateral aspects of the vertebral body 111 are seen the uncinate processes 158, which serve to strengthen the articulation with the vertebra located superiorly to this one. Still further lateral are found the transverse processes 154, which on this view can be noted to be more complex than one might anticipate based on the other views. The neural foramina, as denoted by the bilateral open arrows, are canals which transmit the cervical nerve roots. These arise from the [all important] spinal cord and proceed anterolaterally from the central canal 156 along the groove in the transverse processes 154 to exit into the soft tissues adjacent to the spine, ultimately contributing to the brachial plexus. Also noted is the Foramen Transversarium 159, which transmits the Vertebral artery. The positions of the Vertebral Artery and the nerve roots, in particular, subject a patient to significant risk with placement of lateral mass screws. The pedicle 157, which is in reality a component of the transverse process complex, serves to connect the anterior structures to the posterior arch, thus creating the central canal 156. The posterior arch is comprised of the lateral masses 118 which create the superior and inferior facet joints for the vertebra being examined. Additionally, the laminae 125 and the midline spinous process 132 complete the posterior arch. The central canal 156 contains the spinal cord 175 (not shown in this view), responsible for the transmission of all information to and from the brain, and whose integrity is mandatory for locomotion and many essential functions, is the most critical structure which must be considered with the implantation of any surgical instrumentation into this area of the spine. Additionally, injuries to the vertebral artery or nerve roots must also be avoided as they carry with them substantial deleterious consequences. This view is particularly helpful in showing that the laminae 125 arise from the base of the spinous process 132, and initially assume a rather steep angle in the A-P plane as they move laterally. They then become more horizontal as the continue laterally to become the lateral masses 118. The ideal place for implantation of the laminar anchor is at the transition point, as this is lateral from the spinal cord 175. Such positioning is slightly medial to the lateral masses, where shingling would exclude the possibility of implantation. This ideal position is just slightly less than halfway between the midline and the lateral most edge of the spine, as seen in the posterior view.

This review isn't merely an academic exercise. Rather, it permits one to more completely understand the main and other objectives of the invention and view the invention and its objectives in the proper perspective. Having completed the review, the anatomic terms defined therein will be utilized for the balance of the disclosure.

DETAILED DESCRIPTION OF THE DRAWINGS DEMONSTRATING THE INVENTION

The invention is best understood by studying the following detailed descriptions in conjunction with the context of the accompanying images, wherein like reference numbers refer to like structures, in accordance with common practice. Also in accordance with common practice, the structures illustrated are not necessarily drawn to scale, nor can inferences of scale be developed with respect to such drawings. The embodiments presented and illustrations herein are general representations of the invention, and are not nor can they be construed to be restrictive.

Figure 5:
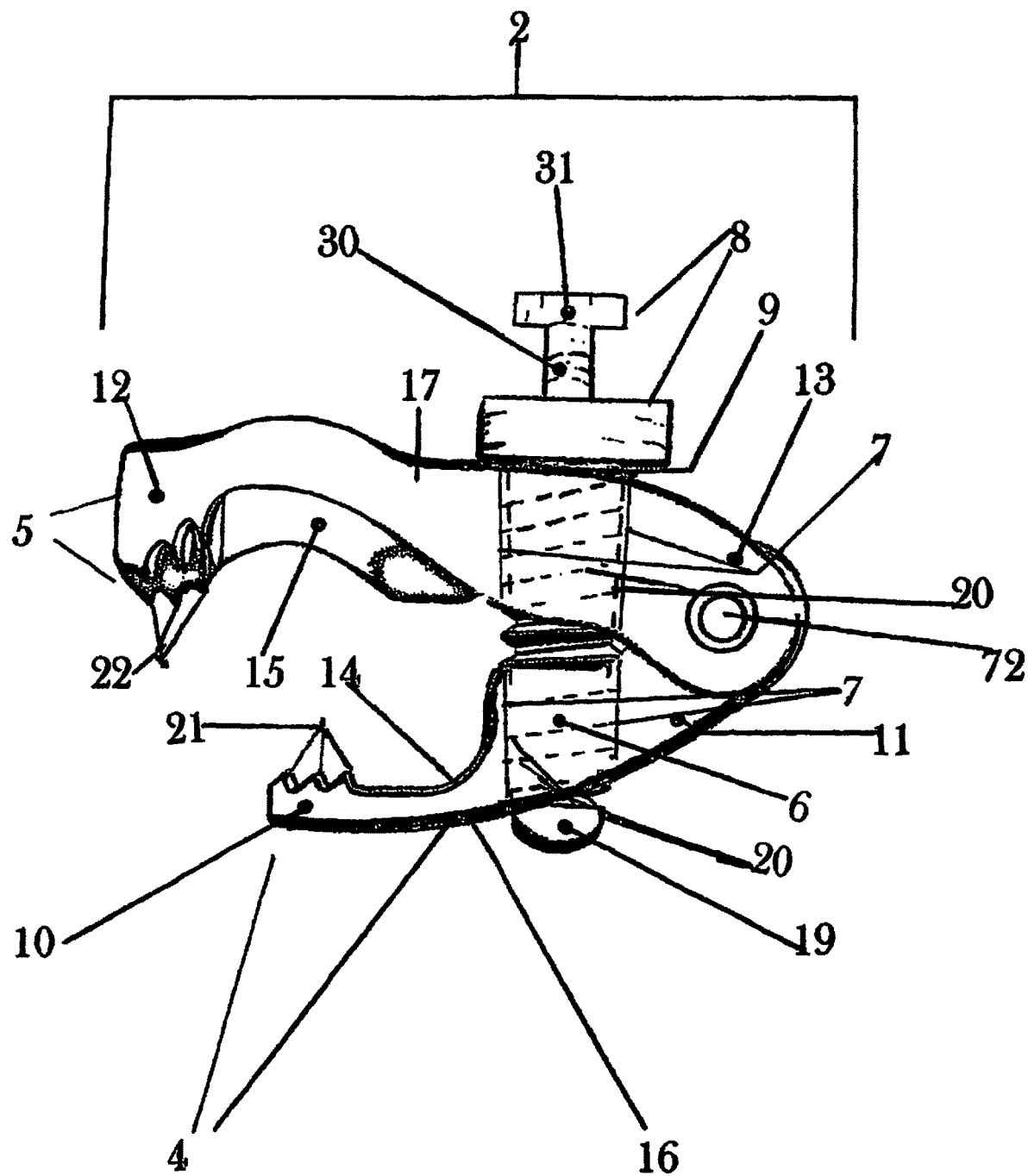
FIG. 5 is a lateral view of an isolated laminar anchor.

Therefore, in turning attention to FIG. 5, which demonstrates a lateral perspective of the preferred embodiment of the Laminar anchor 2, which consists of a minimum of two primary components: an anterior or sublaminar jaw component 4 and a posterior or dorsal jaw component 5. Each jaw is provided with a free end 10, 12, which, in the preferred embodiment, are positioned at the superior I cranial end of the anchor 2; additionally, the two jaws are coupled at the articulating ends 11, 13 located at the inferior I caudal aspect of the anchor 2. This coupling is accomplished in part by the complementary geometry of the articulating ends, which allows the articulating ends 11, 13 to mate with each other. Furthermore, an articulating axle 18 secures this irreversible coupling of two jaws 4, 5. Each jaw is further characterized by a side which is brought against the surface of the lamina, namely the laminar side 14, 15 of the sublaminar jaw 4, and dorsal laminar jaw 5. In addition, the free side of the sublaminar jaw 4 faces the spinal canal proper and therefore is known as the canalicular side 16, while the dorsal laminar jaw 5 is provided with the muscular side 17. Small teeth 21,22 are provided to the laminar sides 14, 15 along their free ends 10, 12. These teeth have blunted, rounded leading ends specifically designed to not penetrate the surface of the bone, but rather are designed to simply increase the surface area and create friction, thus providing greater hold. A tightening screw 6 serves as the actuator to secure the jaws 4, 5 to a target lamina. In the preferred embodiment, the screw 6 is disposed from the muscular side 17 of the articulating end 13 of the posterior jaw 5, transmitting through tract 7 in the articulating ends 11, 13 of the jaws 4, 5, through the coupling of the two jaws 4, 5 and into the articulating end 11 of the anterior jaw 4. The leading most end 19 of the screw can be seen along the canalicular side of the sublaminar jaw 4. The head 8 of this screw 6 is positioned within a threaded groove 9 at the dorsal aspect of the tract 7, with threading 20 of course being present throughout the tract 7. Another feature noted at the head, or trailing end 8 of the screw 6 is a monolithic dorsal extension 30 from the most posterior aspect of the screw. This dorsal extension 30 then terminates in a bar, known as the locking bar 31, which is continuous and monolithic with the dorsal extension 30. These structures serve to lock the connecting element 3 in place.

Figure 6:
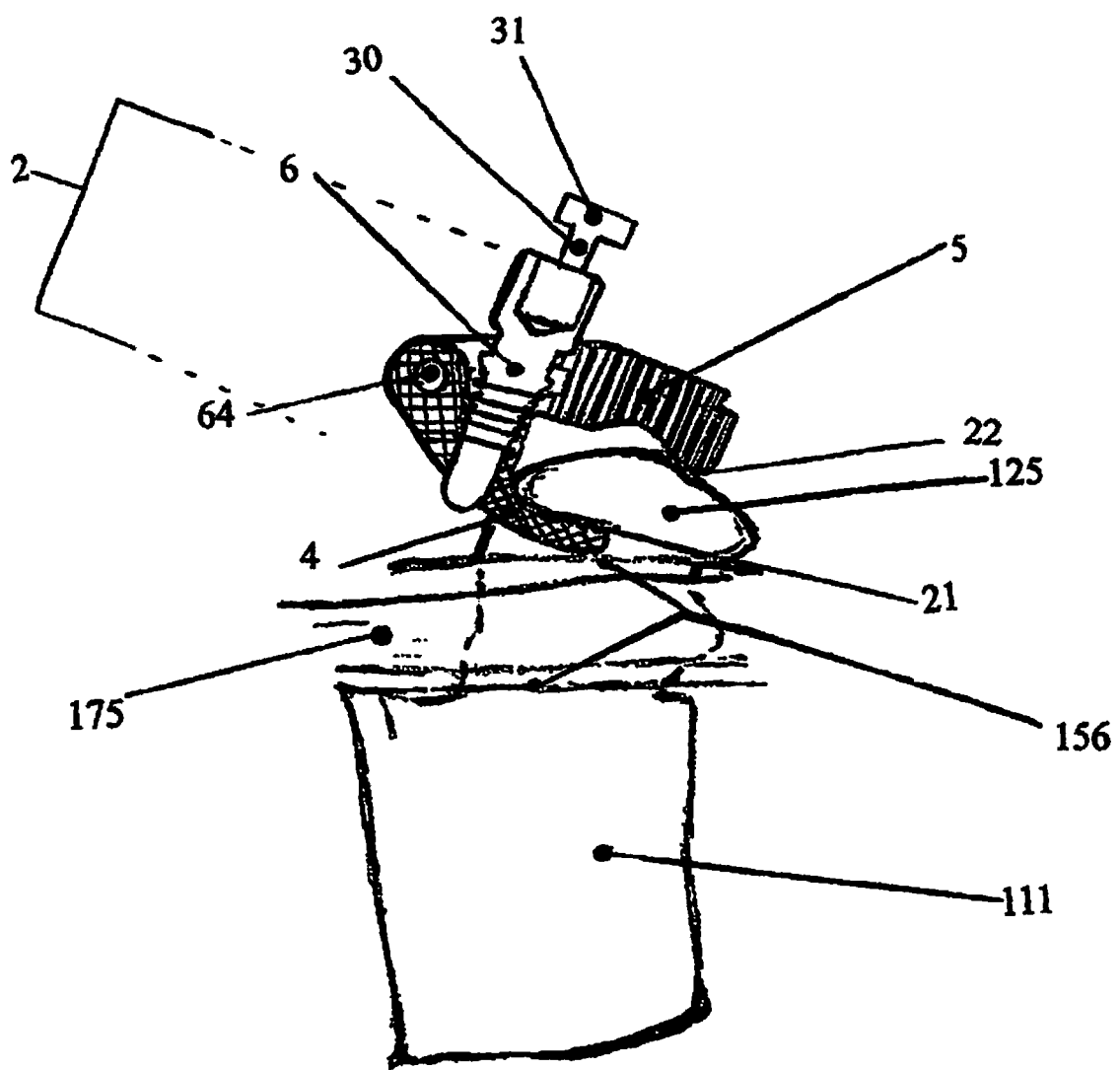
FIG. 6 demonstrates a cut-away/hemisected view of the spine with the laminar anchor in place on the left C5 lamina

The anchor 2 is secured to the target lamina as shown in FIG. 6, a hemisected, non-midline sagittal view. The anterior 4 (stippled) and posterior 5 (striped) jaws are secured against an exemplary target lamina 125 of the C5 vertebra. It is critical to recognize that the thin dimensions of the anterior jaw 4, in combination with its somewhat angled position relative to the orientation of the lamina 125, infinitely reduces the chances of any incursion into the spinal canal 156 by the sublaminar jaw 4. This is further reduced by the technique utilized, and one can see that the spinal cord 175 [the most critical structure in this area under consideration], should not be intruded upon or disturbed in any manner. Upon placement of the anchor against the lamina, the screw 6 is tightened, compelling the jaws 4, 5 towards each other, securing the anchor 2 onto the lamina 125. This provides the system with the required strength of attachment. Again it is noted that the teeth 21, 22 on jaws 4, 5 are just brought against the surfaces of the bone, but are not penetrating the cortical bone per se. Also noted anteriorly is the vertebral body 111 of C5 104 vertebra. It is recognized that in addition to the preferred embodiments described herein, other, similar embodiments will be obvious, especially to those skilled in the art. Such embodiments would include embodiments in which the anchor 2 would be secured to the superior rather than the inferior aspect of any lamina, which would then change the configuration of the jaw components 4, 5. All such embodiments would, of course, be within the spirit and scope of this application.

Figure 7:
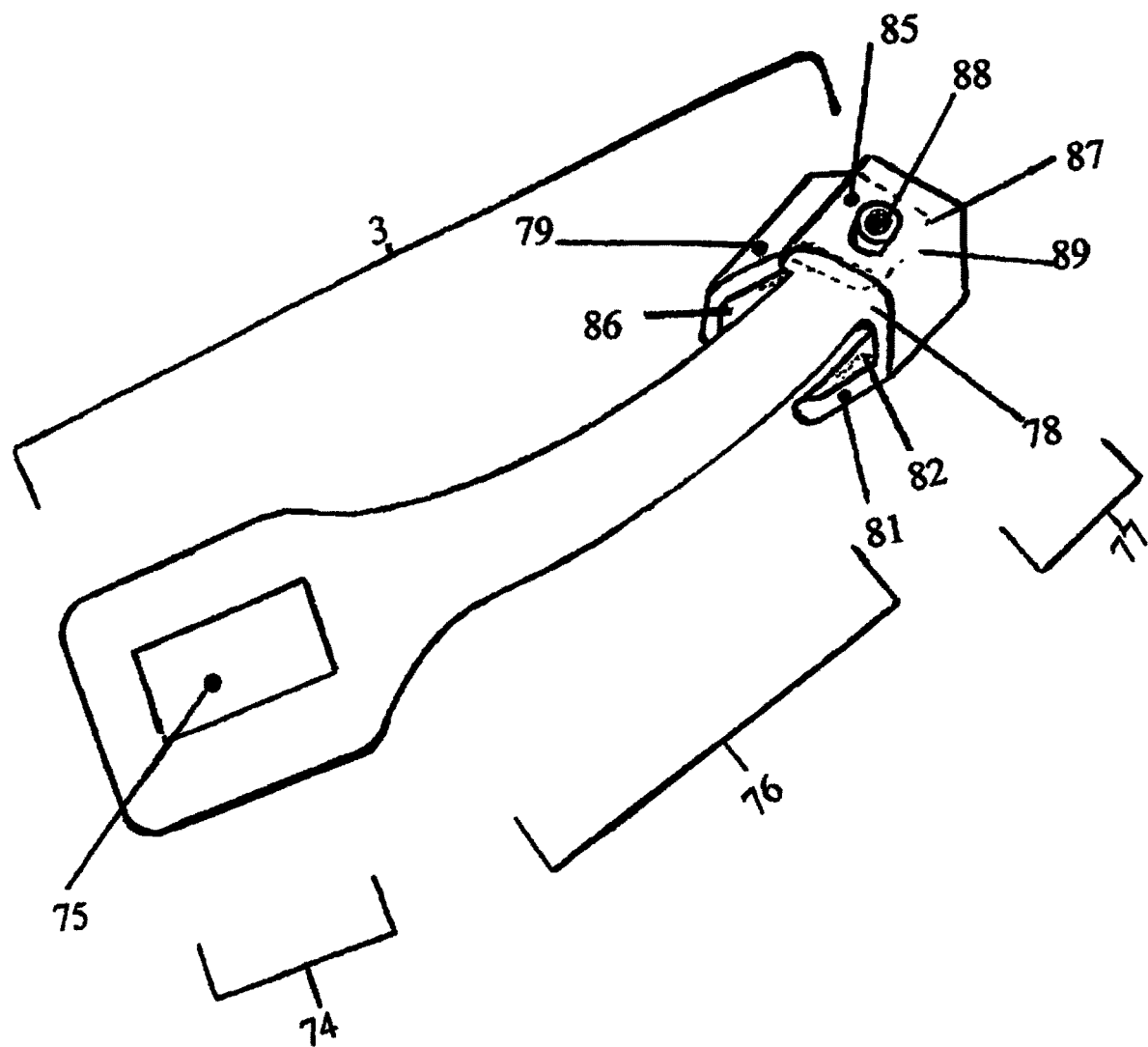
FIG. 7 shows an elevational view of the connecting element that couples one laminar anchor to another.

An elevational perspective of the connecting element 3 which couples the anchors is seen in FIG. 7. Here it can be seen that in the preferred embodiment, this element 3 is monolithic and comprised of a cranial end 74, a shaft-like central portion 76, and a trailing end 77. The element 3 is coupled with the posterior jaw of the caudal anchor through a locking mechanism in the trailing end 77. This is accomplished by providing a housing mechanism 78 which is continuous and monolithic with the trailing most end of the connecting element 3. This mechanism 78, and in turn the connecting element itself, can be brought against the muscular aspect of the dorsal jaw. Furthermore, this mechanism 78 gives rise to and is monolithic with a clamping arm 81 which extends anteriorly and has an internal surface 82 configured to appose the side of the dorsal jaw. A movable component 79 is provided with a horizontal component 85 that is slidably coupled with the housing mechanism 78, specifically by passing through a substantially rectangular aperture 84 which is then continuous with a chamber 87 which has been provided to the dorsalmost aspect of the housing mechanism 78. This horizontal component 85 is then continuous and monolithic with a clamping arm 83, again with an internal surface 86 configured to be brought against the anchor which extends anteriorly along the opposite side of the dorsal jaw from the fixed clamp 81. These two clamping arms 81, 83 are displaced towards each other, and the dorsal jaw is secured between them, coupling the connecting element 3 to the anchor. On the dorsalmost aspect of the housing mechanism 78 is a tract 89 that accepts a securing screw. 88, which will lock the connecting element 3 onto the desired position on the jaw 5 of the anchor 2. This would be determined by the distance between the cranial and caudal anchors and coupling the connecting element 3 to the cranial anchor. This is accomplished by the configuration of the leading end 74, which demonstrates a unique area which is flattened, in the preferred embodiment is substantially rectangular but can be of any configuration and is provided with an aperture 75. The coupling is accomplished by disposing the aperture 75 over the locking bar 31 and rotating the screw; hence, the leading end 74 of the connecting element 3 will be secured simultaneously while the jaws 4, 5 are secured to the lamina.

In an optional variation, this connecting element can be divided into two halves throughout its length, so as to be configured to function as an actuator which can expand or contract the dimensions of the aperture at the leading end of this connecting element. Alternatively, in any of the embodiments, the connecting element may also be constructed of a cranial and caudal segment coupled by a separate element which can modulate the craniocaudal length of the connecting element, thus accounting for variances in this dimension. These will be illustrated below.

Figure 8:
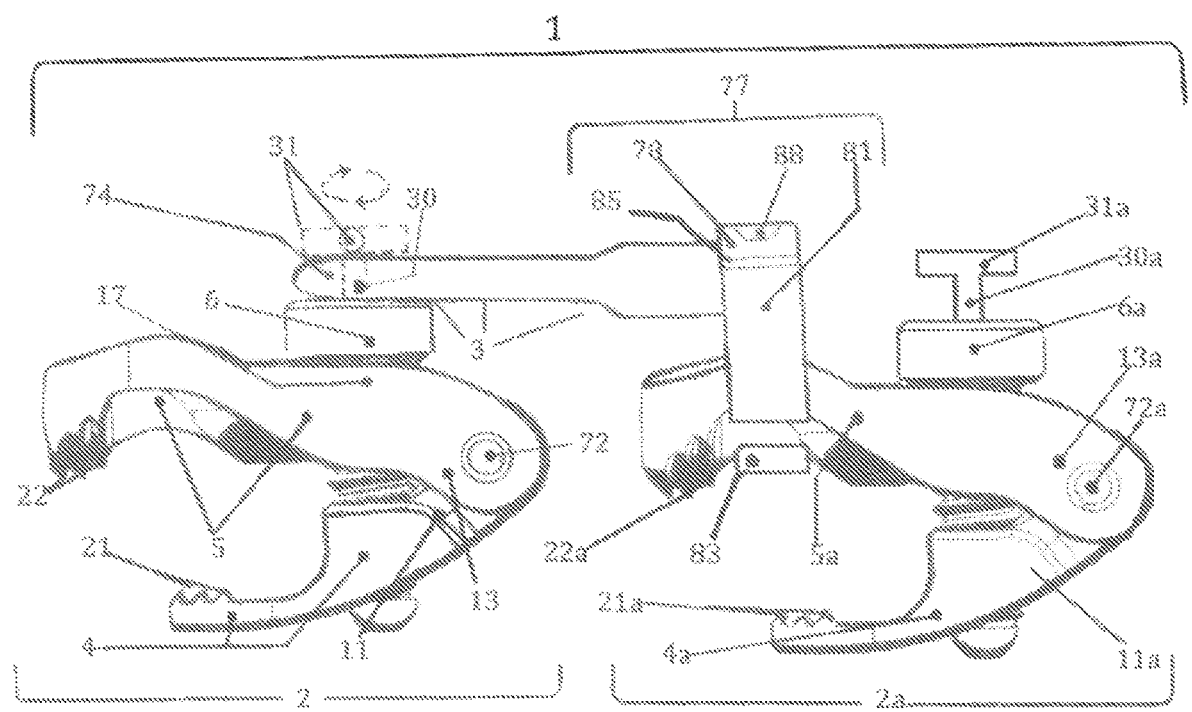
FIG. 8 is a lateral view of the preferred embodiment of the CMIS in which the rod-like connecting element couples a cranial laminar anchor to a caudal anchor.

FIG. 8 is a lateral perspective of the fully-assembled preferred embodiment of the CMIS 1. On the viewer's left is the cranial laminar anchor 2, coupled by the connecting element 3 to the caudal laminar anchor 2a. Each of these anchors 2, 2a are characterized by an anterior jaw 4, 4a which is insinuated beneath the caudal end of a target lamina. The anterior 4, 4a and posterior S, Sa jaws are coupled by the axles 18, 18a; with tightening of the screws 6, 6a, each pair of jaws (4, S I 4a, Sa) are compelled towards each other, thus securing the laminae between the jaws. The aperture 7S (implied, not shown) in the leading end 74 of the connecting element 3 is then disposed over the horizontal bar 31 of the trailing end of the screw 6. The jaws 4, 4a, S, Sa have already been secured against the bone; however, a single additional quarter turn of the screw 6 is needed to position the horizontal bar 31 (seen on-end as solid circle and as stippled outline in primary position) to secure the leading end 74 of the connecting element 3 in place. This is indicated by the curved arrows seen above the horizontal bar 31. The caudal end 77 of the connecting element 3 is coupled to the posterior jaw Sa of the caudal anchor 2a by the clamping arms 81, 83. This is accomplished by the housing mechanism 78 described in FIG. 7, which encourages the clamping arm 83 of to be displaced towards the clamping arm 81 until these are firmly secured against the posterior jaw Sa of the caudal anchor 2a. The securing screw 88 of the housing mechanism 78 is then deployed, locking the construct in place. An alternative embodiment can be envisioned in which clamping of the connecting element to the caudal anchor 2 is accomplished with the use of a clamping configuration. In another alternative embodiment, the connecting element 3 is a component of the caudal anchor. In such a configuration, the leading end 74 must be negotiated into position by being disposed over the horizontal bar 31 prior to actuation of the bar and thereby locking the connecting element 3 in place. In the preferred and alternative embodiments disclosed herein, the final embodiments will appear to be substantially quite similar if not identical, although the assembly of these various embodiments differ; they all stabilize the target motion segment by securing the laminar anchors 2, 2a, 2b to the target laminae and then connecting the anchors by the connecting element 3. Alternative embodiments are specified and illustrated below, but it is recognized that these are not exclusive and that those skilled in the art may envision other embodiments which accomplish these goals and objects, as obvious variations beyond those specified may be envisioned. All such embodiments are within the spirit and scope of this inventive method and devices, and within the spirit and scope of this application.

The CMIS is implanted utilizing a Minimally Invasive Surgical (MIS) approach, which is accomplished by combining intraoperative imaging and anatomic understanding to relate surface landmarks to subsurface structures. This results in a precise surgical incision directly over the point on the lamina to which the anchor will be secured, which is the point where the lamina transitions from a steeper portion to the more horizontal portion, as described in FIGS. 3 and 4 above. This point is approximately 40-45% of the distance between the midline and the later almost edge of the target vertebra. In order to insinuate the anterior jaw of the anchor into its ideal location, the exposure must not be too lateral, or the later almost aspect of the spine will prevent implantation. Rather, this jaw must be introduced through the lateral aspect of the interlaminar space. The position of the incision can be predicted by the use of a unique, useful, novel and nonobvious guide template 80, the preferred embodiment of which is demonstrated in FIG. 9 A. This template 80 is ideally a group of three sterile, clear, colorless plastic disposable sheets 90,200 which are placed on the surgical field (the back of the neck of the prone patient) after the sterile prep and drape of the area has been completed. Each of these sheets have been impregnated with visibly dark lines which are made of radiopaque material. The first of these components, the midline template 90, is a long, thin sheet in which the radiopaque line is merely a straight I interrupted line 201 used to indicate the midline. The surgeon uses fluoroscopy to identify the midline, then aligns the fluoroscopic image of the template 90 to the spinous processes. Once the surgeon has achieved this, the skin reference points indicating midline are readily seen, given that the midline markers are visible both grossly and fluoroscopically. Then the second component 200 of the template 80 is brought into the field. This pair sheets is provided with the outlines 92, 93 of the lateral edges of the spine, as well as a corresponding set of apertures 94 along the medial edge, presumably identifying the ideal sites for placing the localizing needles.

Figure 9A:
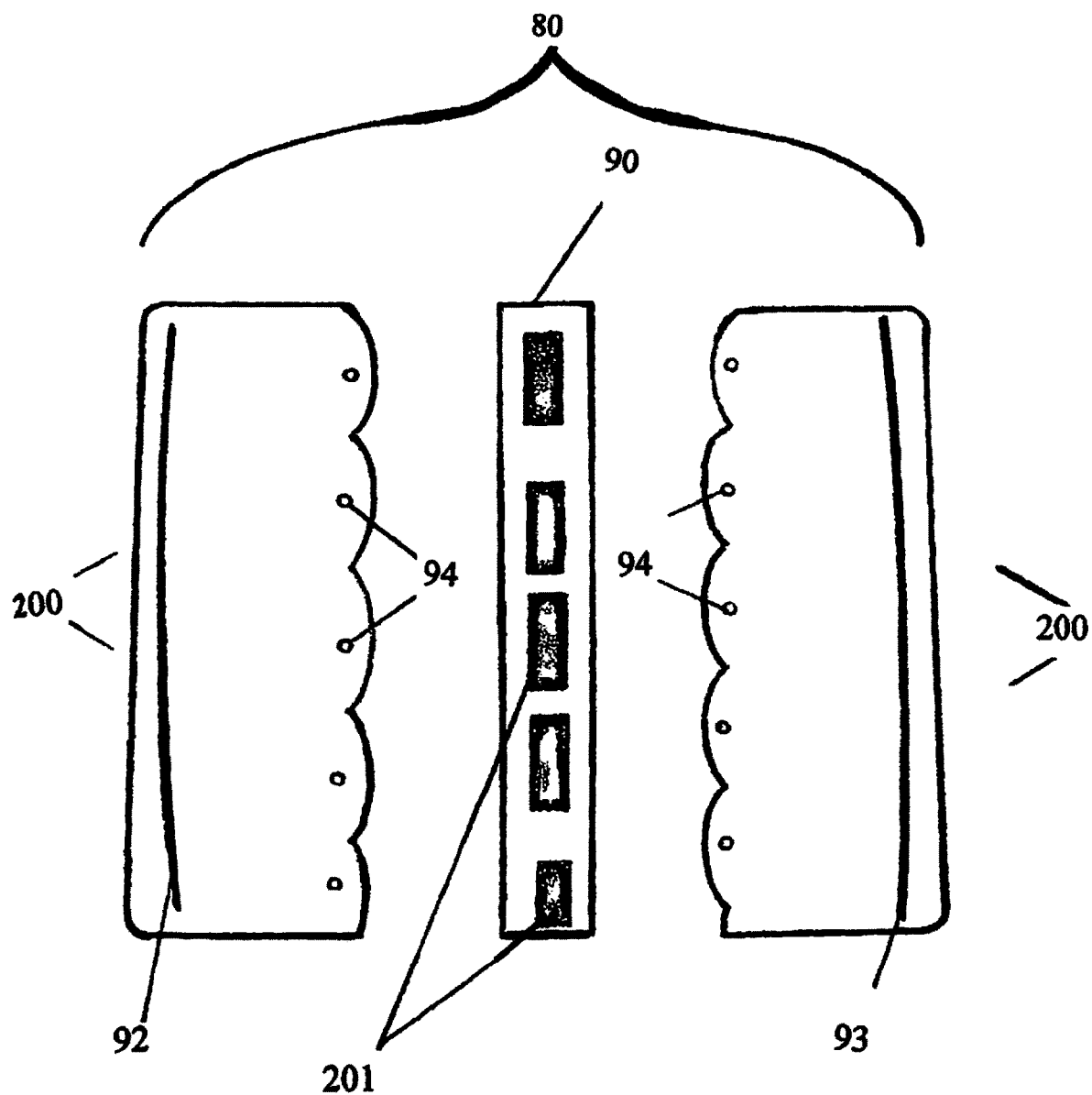
FIGS. 9 A/B demonstrate the preferred and alternative templates which assist the surgeon in determining the site of the incision.
Figure 9B:
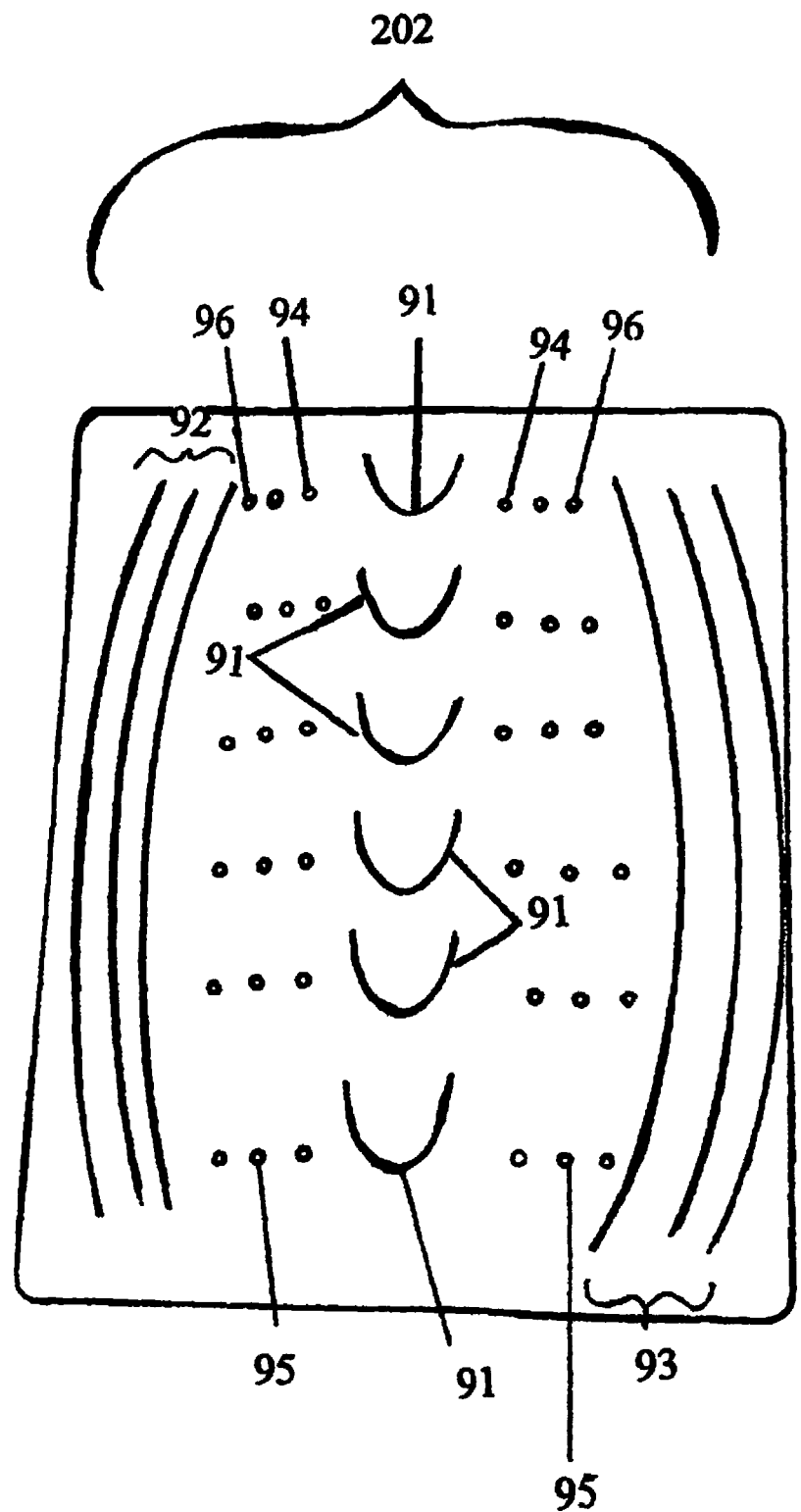

In FIG. 9 B, demonstrating an alternative embodiment of the template, a single sheet serves as the template 202. Again, a visibly dark, radiopaque substance has been used to create outlines of key anatomic landmarks of the cervical spine as seen in the P-A fluoroscopic projection. Specifically, the template includes images corresponding to the spinous processes 91, which establish the critical midline landmark, as well as a series of lines indicating the lateral-most edge of the spinal column 92 (left) and 93 (right). A series of lines is provided to adjust for the varying sizes of the lateral aspect of the neck seen in different patients. In addition, there are a series of apertures 94, 95, 96 which correspond to the different positions of the lines 92, 93 moving from left to right, which serves to dictate the position and trajectories of guide needles, and ultimately the sites for the incisions. The illustration using 3 lines I 3 sets of apertures on each side is purely exemplary, and any number of such features can be used. For simplicity, the number of lines should equal the number of apertures, but such an embodiment is not the exclusive anticipated format. Of course, any and all such embodiments would be within the spirit and scope of the invention.

Figure 10:
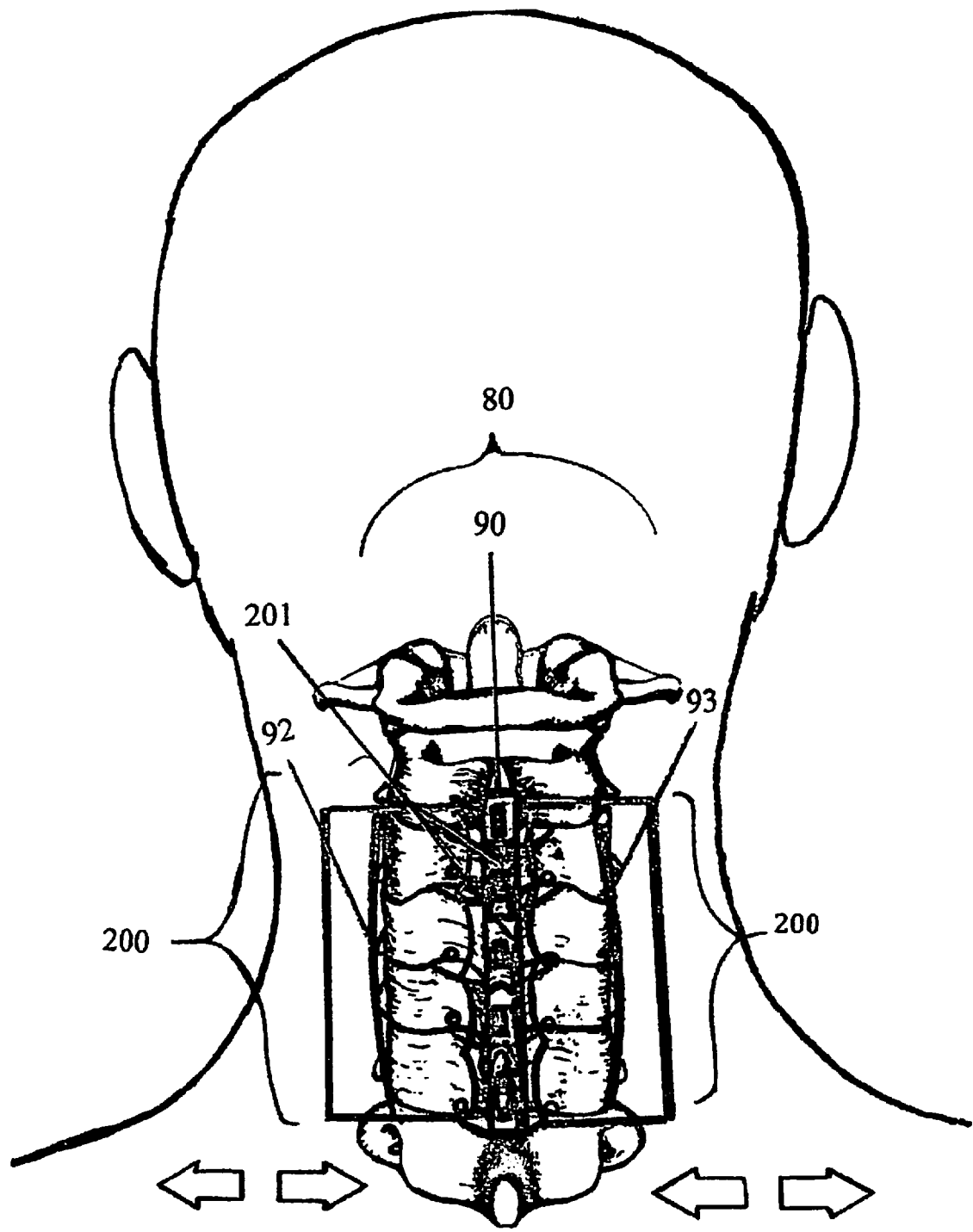
FIG. 10 portrays a posterior perspective showing the preferred method for selecting the incision site.

FIG. 10 is a view of the head and neck of the prone patient with the preferred embodiment of the template 80 in place superimposed upon the bony anatomy of the cervical spine. This represents a fluoroscopic image in the P-A projection, and establishes the midline by aligning the midline template 90 to the midportion of the spinous processes. Additionally, the identifying lines 92, 93 on the lateral templates 200, are precisely aligned with the lateral edges of the spine by moving the templates 200 laterally or medially—as demonstrated by the open arrows. Such a system would allow the surgeon to be able to achieve the ideal implantation through an optimal minimum incision. As the size of the spine varies between individuals, the position of the lateral edge of the spine with respect to the midline will also change. This relationship is critical in determining the site(s) of the incisions, as previously disclosed. In the alternative embodiment, the lateral edges of the spine are demarcated not by a single line but rather a series of radiopaque lines which account for the variability of sizes, providing the surgeon with a number possible positions of the lateral spinal edge and its relationship to the midline. The surgeon will ideally match the actual radiographic appearance of the midline and lateral edges to the closest appearance on the template, and then utilize the apertures that relate to the alignment of the lateral edge; therefore, if the intermediate line is that one most closely associated with the lateral spinal edge, then the intermediate aperture 95 would be the most appropriate aperture to accept the localizing needle 97. Because patients with anomalous body morphology may not conform with the sites predicted by the apertures, the surgeon would be obliged to be certain in scrutinizing the images and placing the incisions slightly less than halfway between the midline and lateral edge, which will always result in excellent positioning. The ideal incision would be made in a horizontal, or mediolateral plane, consistent with Langer's lines. This would result in the most acceptable cosmetic effect as well as the best functional outcome. However, vertical incisions would also certainly be acceptable and in keeping with the spirit and scope of this inventive method.

Figure 11:
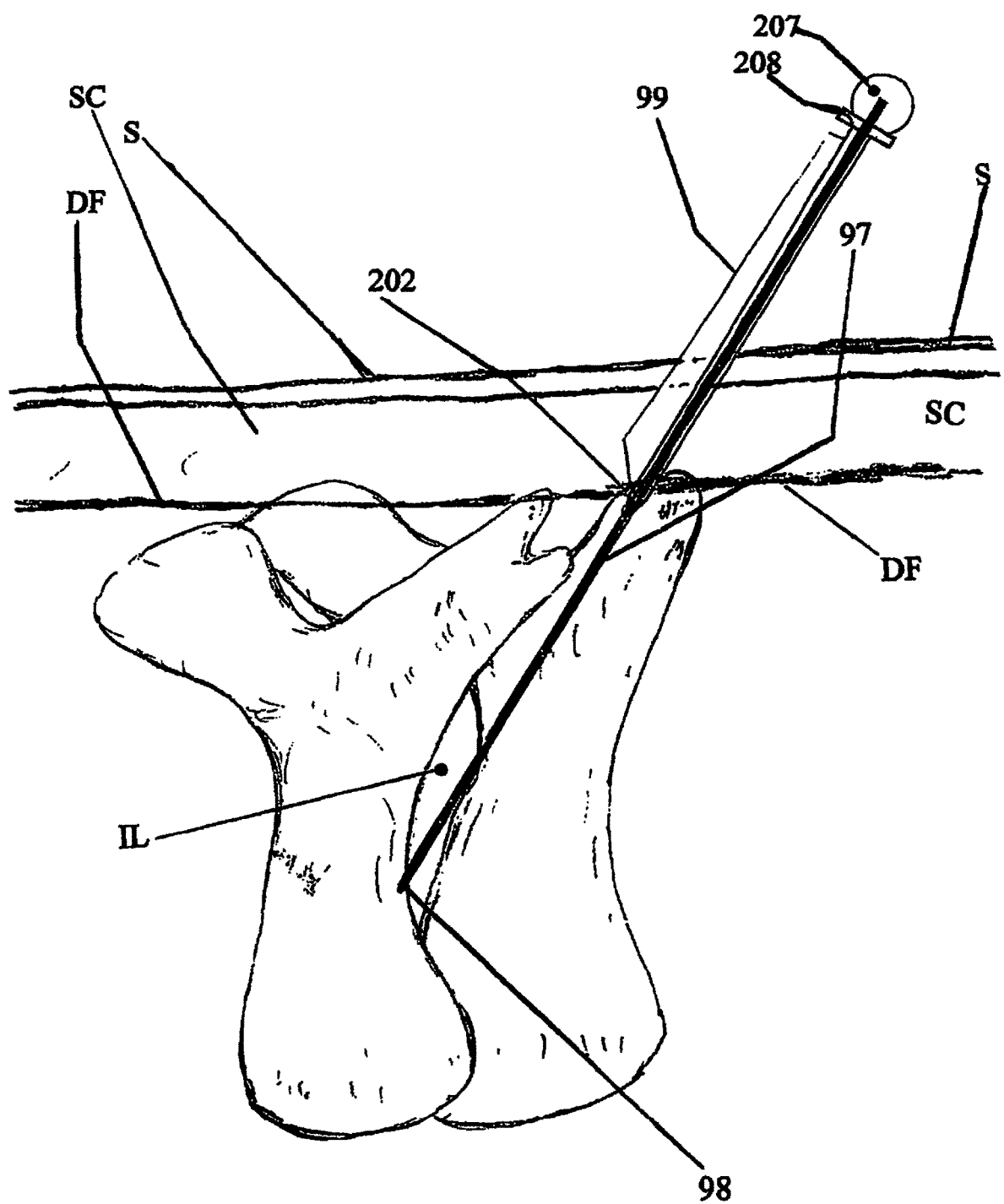
FIG. 11 illustrates a localizing needle against the posterior lamina.

Once the proper the aperture has been identified, a guide needle 97 is passed therethrough, and another fluoroscopic image confirms placement, as demonstrated in this lateral elevational view. In this image, the needle 97 has been positioned the left lamina of C5 125 for illustrative purposes. The needle 97 has been provided with a blunt leading end 98; the advantage of the blunt leading end 98 is that if the needle is imperfectly placed and introduced into the interlaminar space IL, it would be unlikely that the blunted leading end could easily penetrate the ligamentum flavum which lies dorsal to the dura, the overlying membrane of the spinal cord. This blunt needle, obviously, would not be able to penetrate the skins, subcutaneous tissues SC or the dorsal fascia DF. Hence, a sharp-tipped needle 99 of a slightly larger caliber is initially introduced, and passed deep to the dorsal fascia DF. This needle is shorter, so as to [again] not penetrate through the interlaminar space. Ideally, the sharper introducer needle 99 is positioned closely fitted to the outside of the blunt localizing needle 97, with the leading end 202 of the outer sharp needle 99 just extending below the fascia DF and the inner blunt needle 97 extending to the bone, with the leading end 98 having been brought against the inferior or caudal aspect of the C5 lamina 125, at the lateral edge of the interlaminar space IL. In one embodiment, the localizing needle 97 is fabricated from [a radiolucent] hard plastic, except for the leading end 98, which would be composed of [radiopaque] metal, such as stainless steel. Making only the tip radiopaque would make intraoperative imaging visualization of the leading end significantly easier. Both of these needles 97, 99 are demonstrated in FIG. 11. Also demonstrated is the trailing end 207 of the blunt needle 97, as well as the trailing end 208 of the sharp needle 99. The trailing end 207 of the blunt needle 97 is reversibly coupled to the needle 97, such that the trailing end 207 can be removed. This would then allow the outer sharper needle to be removed from the surgical field, thus allowing the skin penetrating device 203 to be disposed over the blunt needle 97.

After placement of the localizing blunt needle 97, a limited horizontal or vertical incision is centered over the needle. The incision can be achieved using a standard surgical blade; alternatively, the use of a unique, useful, novel and nonobvious device is proposed which is purpose-specific for achieving this goal, and is portrayed in the frontal view in FIG. 12 A. This skin entry device 203 is provided with a leading end 204, a complex central area and a trailing end, and is utilized in conjunction with the blunt needle. The leading end 204 is a central projection which has been provided with an aperture 209 which is continuous with a channel 205 dimensioned to accommodate the blunt needle, over which this central channel 205 is disposed, placing the incision in an ideal position. The circular leading most end 209 which forms the entry into the channel 205 is quite sharpened, as this surface will make the initial incision. Sharpened edges 210 then extend bilaterally along the sides of the projection which forms the leading end 204, these sharpened edges extending the incision bilaterally from the puncture created by the introducing needle 99. This incision is then further expanded by the sharpened sides 211 of medial and lateral wings 206 which extend bilaterally from the central channel 205. This creates the ideal sized incision, with an equal cut created on both sides of the needle tract. The thumb rest 212 and the handle 213 are seen in the frontal view.

Figure 12:
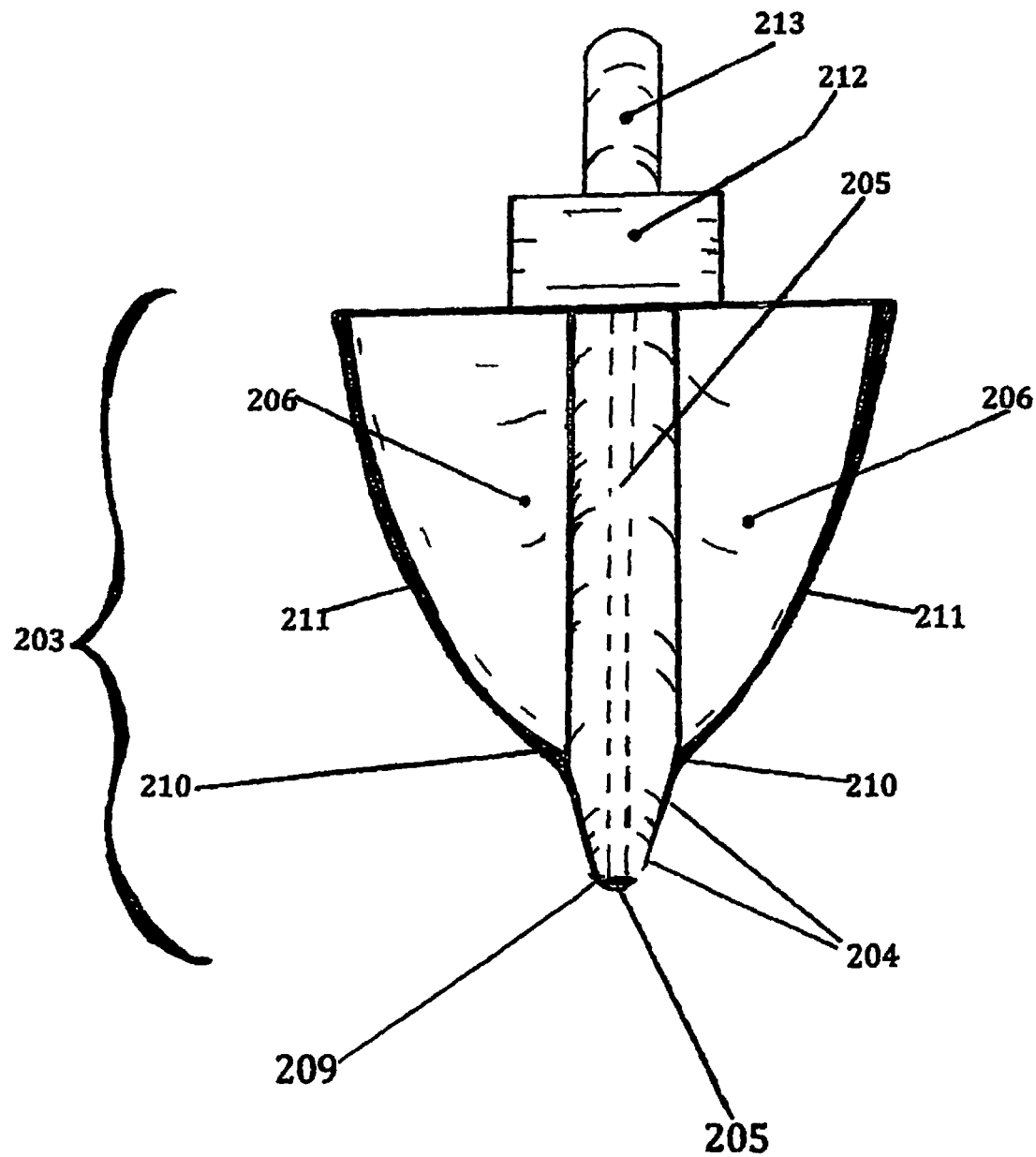
FIGS. 12 A/B/C includes frontal, lateral and elevational views of the instrument used to create the skin incision.
Figure 12B:
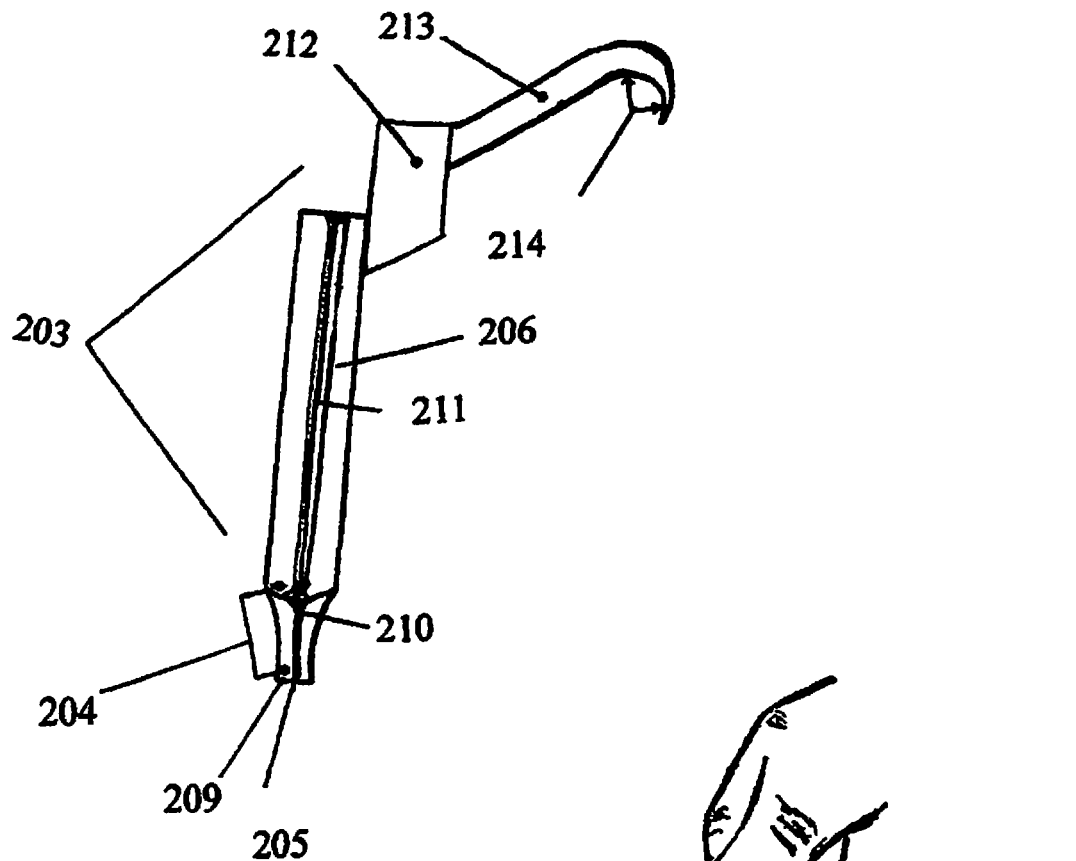
Figure 12C:
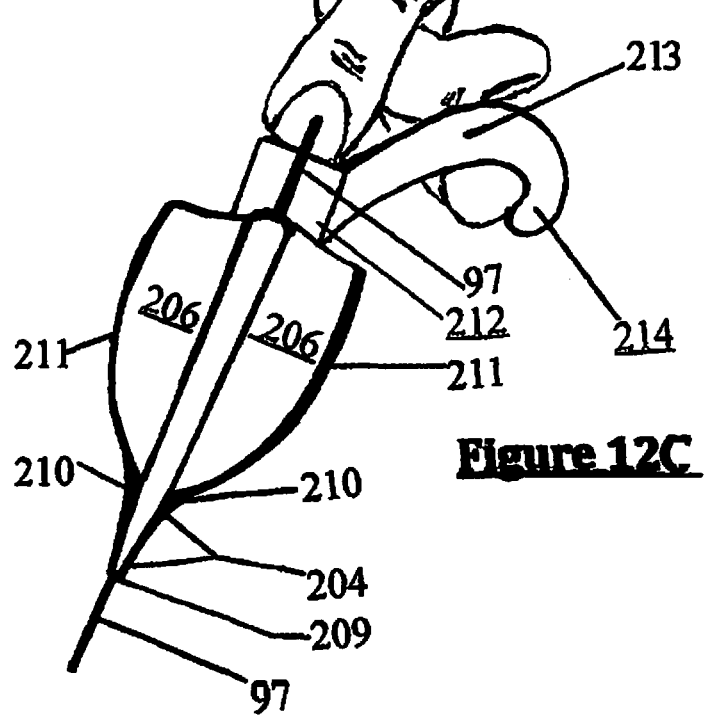

FIG. 12 B, a lateral view demonstrates certain aspects of the device 203, including details of the handle 213 and how this configuration results in the actuation of the device 213. One can see the leading end 204 with its sharpened leading edge 209, the sharp sides 210 of the leading end 204 as well as the sharpened edge 211 of the ipsilateral wing 206. Furthermore, one also appreciates the thumb rest 212, and the handle 213. At the trailing end of the handle 213 is found the index curve 214, which further stabilizes the device 203 during insertion.

Actuation of the skin entry device can be appreciated in the elevational view in FIG. 12 C, which shows the device being disposed over the localizing needle 97. The leading end 204 would be in position so that the circular rim 209 would create an incision centered around the needle track, extended by the sharpened sides 210 of the leading end 204, which is further extended by the sharpened sides 211 of the wings 206 of the device 203. In order to insert the device 203, the surgeon's thumb is placed on the thumbrest 212, with a stabilizing finger inside the curve. The surgeon then pushes down with the thumb and the device will pursue the needle track down to and just through the level of the dorsal fascia, exposing the dorsal cervical musculature and preparing the operative field for the next step. In one embodiment, it can be imagined that the entire device is fully disposable; in another embodiment the lateral wings 206 with the associated sharpened, blade-like edges are disposable, while the central portion is a permanent, reusable embodiment.

The surgeon must then open the posterior cervical musculature and free them from the target laminae, hence exposing the bony target areas. This can be accomplished in a variety of ways, and disclosed herein is the use of a unique, useful, novel and non-obvious device which is a purpose-specific muscle-splitting I dissecting device. Said device 215 is illustrated in images 13 A-E, and is initially demonstrated in the non-deployed position in the elevational view 13 A. The device 215 is comprised of two substantially elongated principal components, a cranially-directed component 216 and a caudally-directed component 217. Each of these are, in turn, provided with a leading end 218, 222, a shaft 219, 223 and trailing end 220, 224 with the two components irreversibly coupled at an intersection with an Axle 221; this is positioned orthogonal to the long axis of the two components 216, 217. This intersection creates a scissoring, pivot point mechanism around which the two components 216, 217 can rotate. In one embodiment, this coupling is spring-loaded to maintain the device in the non-deployed position.

Better seen in FIG. 13B, an elevational view of the device 215 in the deployed position, the leading ends 218, 222 are footplates which arise at a bias from the shafts 219, 223. This bias is angled away from the shaft 219 I trailing end 220 of the cranial component 216. In the functional position within the operative field, this would be angled anteriorly (away from the surgeon). The leadingmost edge 226 of the foot plated leading end 218 is narrowed to a sharpened edge, which is useful in splitting the muscle layers and dissecting the muscular attachments from the bone. The shaft connects the leading end 218 with the trailing end 220. The axle 221 couples the cranial element 216 to the caudal element 217 in an intersecting fashion, creating a lever I moment arm when the components 216, 217 are actuated. The trailing ends 220, 224 are provided with finger I thumb grips 228,229 to assist the surgeon in actuating the instrument 215.

Figure 13:
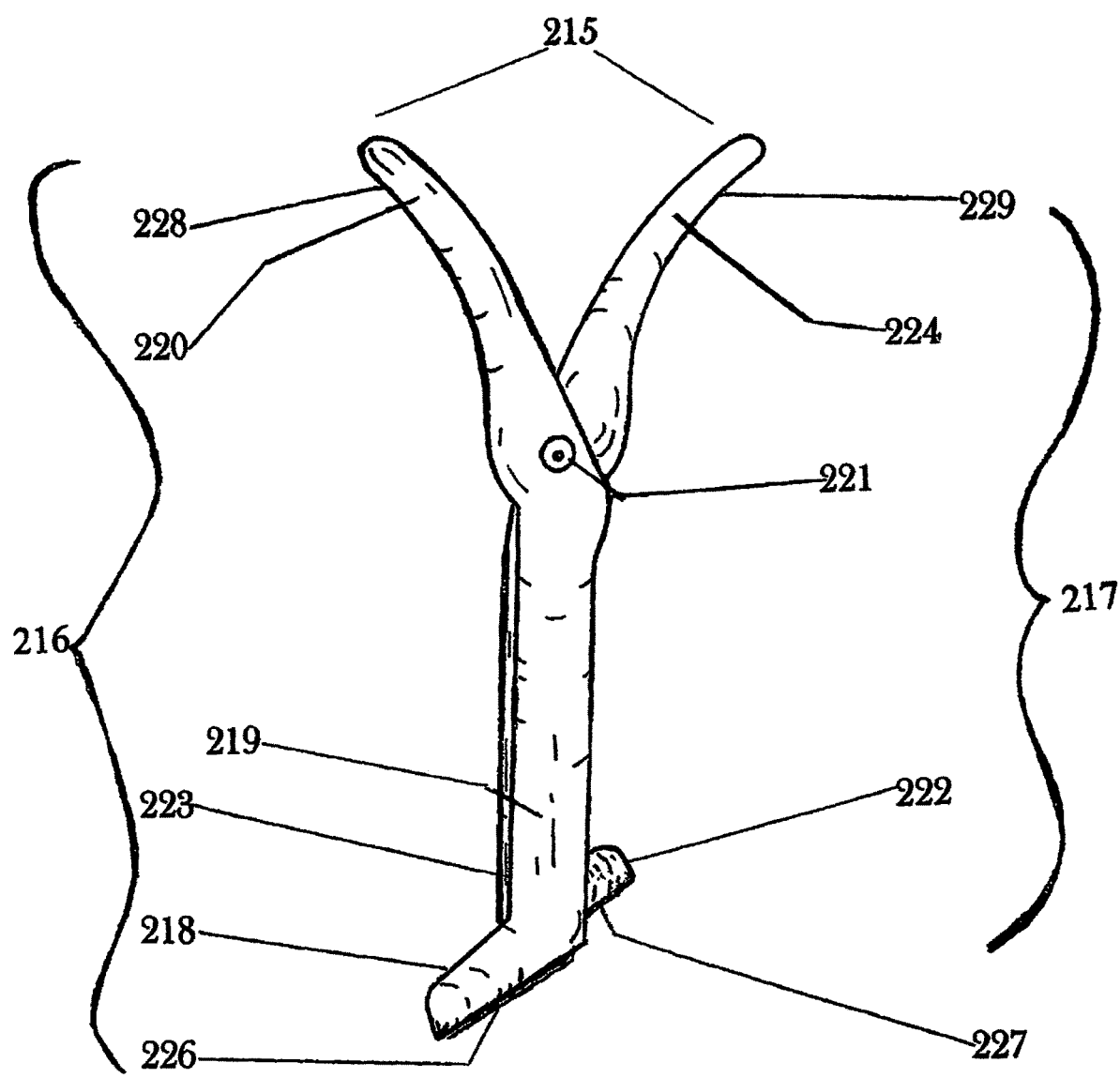
FIGS. 13 A-E demonstrates various views of the instrument which dissects the posterior cervical musculature.
Figure 13:
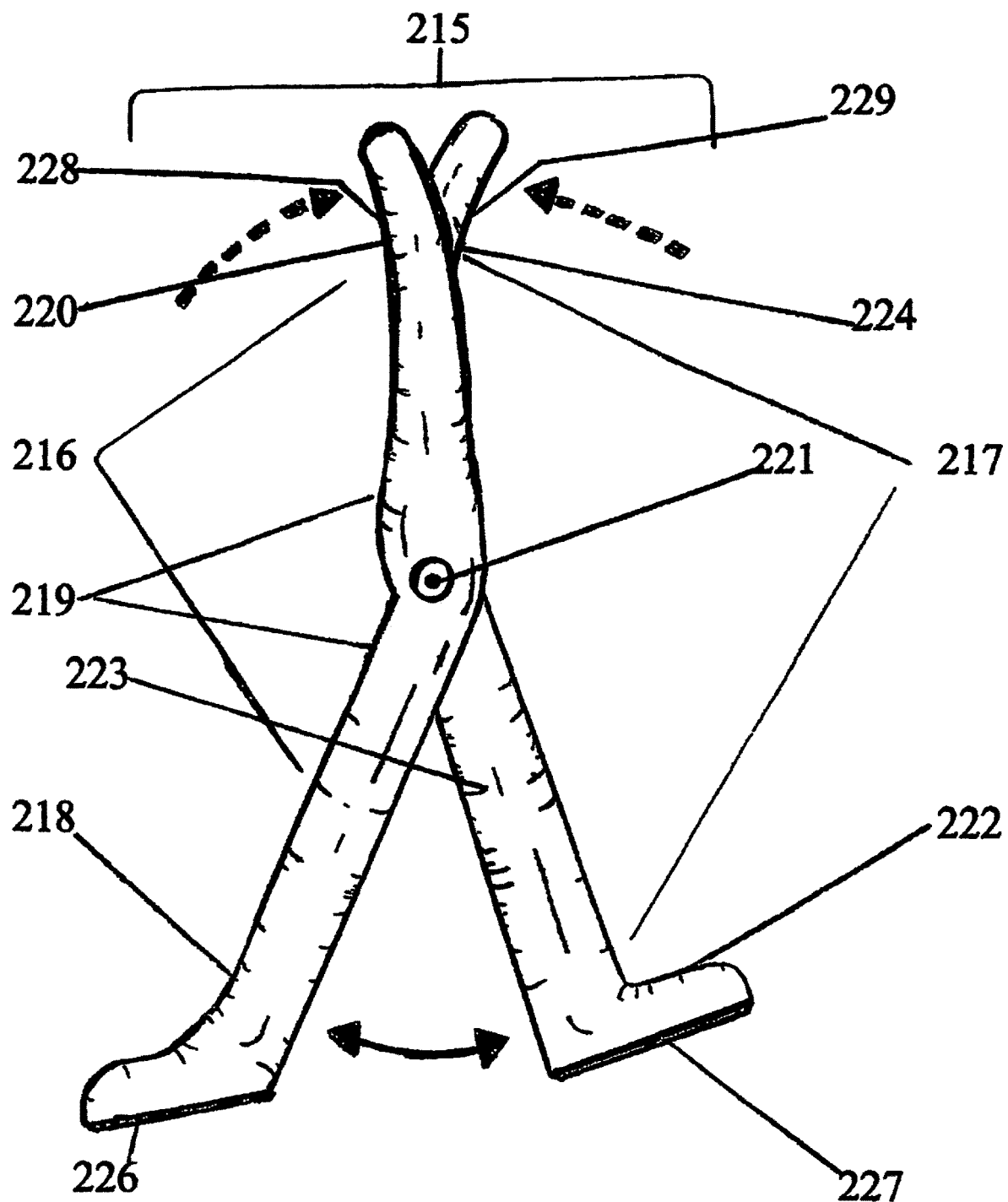
Figure 13:
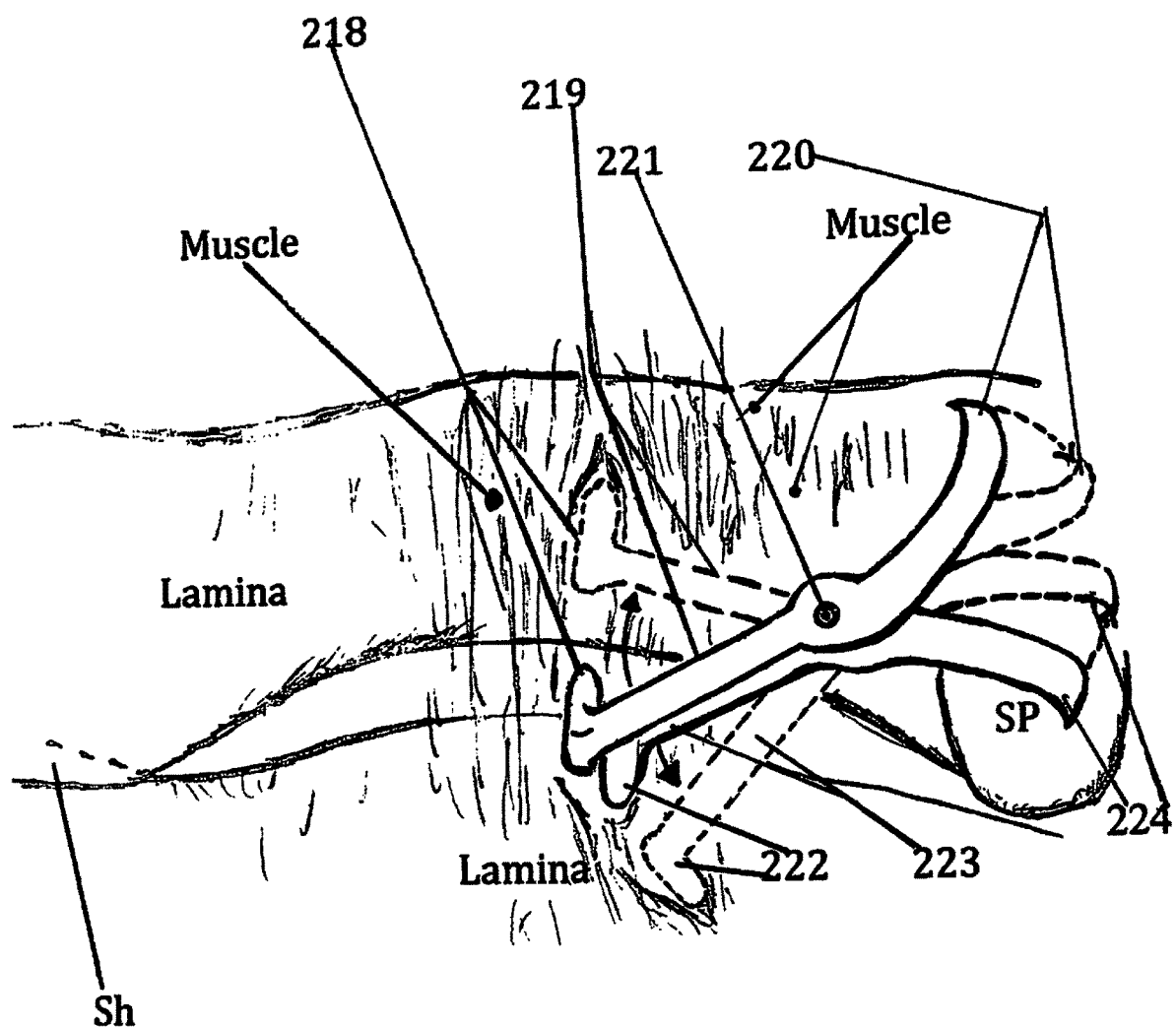
Figure 13:
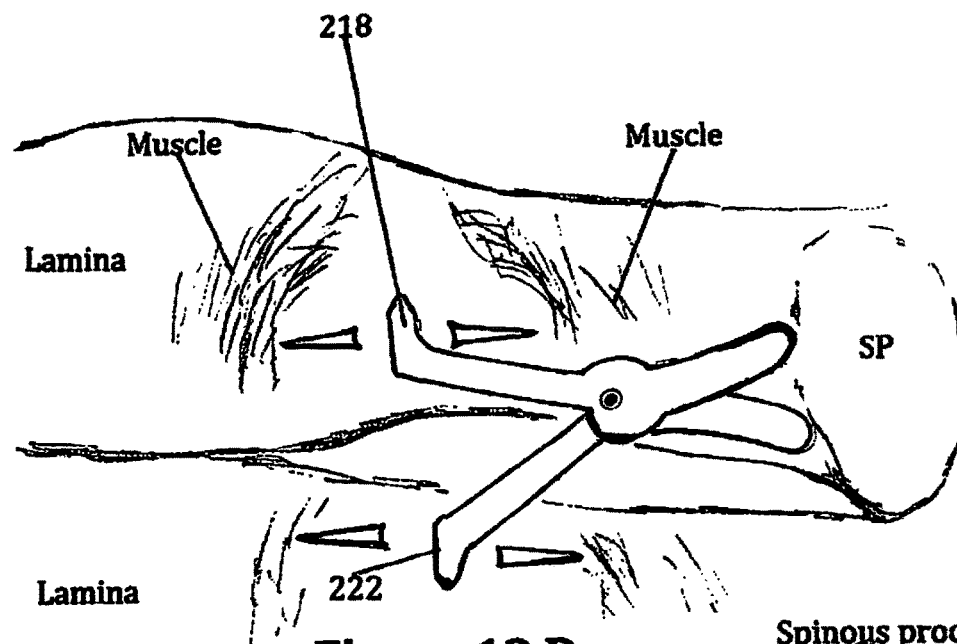
Figure 13:
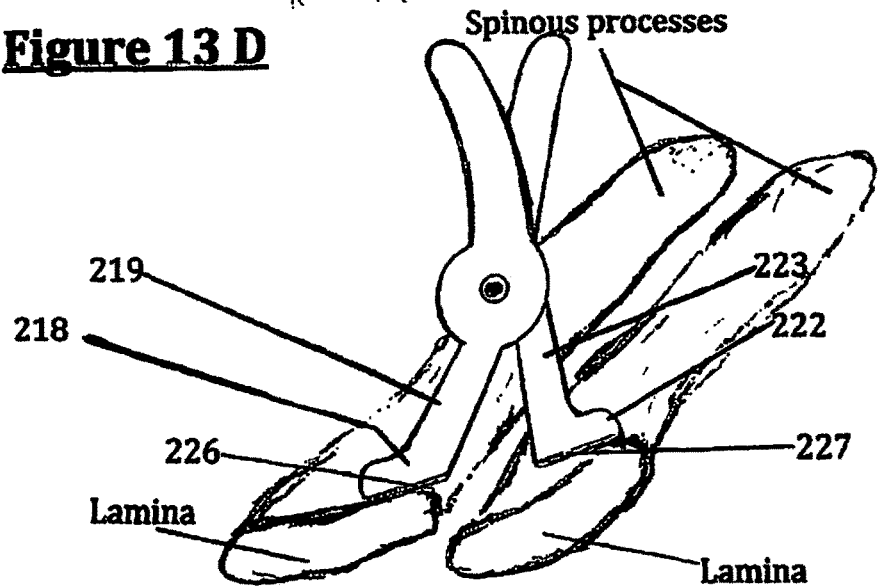

The caudal component 217 is better seen in FIG. 13B, and is comprised of a leading end 222, a shaft 223 and a trailing end 224. As in the cranial component 216, the leading end 222 of the caudal component 217 is a footplate which arises at a bias from the junction with the shaft 223, but in this instance, the bias is configured such that the foot plate is angled posteriorly (towards the surgeon). As the two components 216, 217 of the device 215 are of substantially the same length, when the device 215 is in the non-deployed position, the two leading ends 218, 222 substantially align with one another. Although the biases of these two footplates are polar opposites with respect to the shafts 219, 223, the angles the footplates describe are substantially complementary, so these footplates 218, 222 can be partially superimposed upon each other as viewed from the lateral perspective in the non-deployed position, suggested in FIG. 13 A. This configuration will facilitate the initial insertion into the muscle fibers. The leadingmost edge 227 of this foot plate 222 is again provided with a sharpened edge 227. The trailing end is also provided with grips 229. It is also noted that the two shafts 219, 223 are slightly divergent at a point beyond the axle 221, such that the trailing ends 220, 224 are divergent in the non-deployed position, as seen in the lateral perspective.

It can be seen in FIG. 13 B that the device is actuated by manipulating the trailing ends 220, 224 towards each other assumedly with digital pressure on the finger I thumb grips 228, 229. This causes both components 216, 217 to pivot around the axis, compelling the leading ends 218, 219 away from each other—as indicated by the solid arrows. Other embodiments of the leading and trailing ends creating a moment arm around an axle can be envisioned, and of course are within the spirit and scope of the invention.

In FIG. 13 C, a posterior view of the surgical field, the posterior cervical muscle fibers are seen oriented in a craniocaudal direction. This view demonstrates the actuation of the device 215. As such, the leading ends 218, 222 of the non-deployed device 215 are seen as solid lines being insinuated between these muscle fibers "Muscle." Deploying this (indicated by the "ghosted," images created by the interrupted lines) by manual pressure on the trailing ends 220, 224 causes the shafts 219, 223 and leading ends 218, 222 to become divergent, dissecting the fibers along anatomic planes. This spreads the tissues rather than cutting them, minimizing bleeding and damage to tissues, while exposing the target bony surfaces of the upper and lower lamina. The spinous process SP demarcates the midline. The "Shingling," of the later almost laminae is depicted Sh.

FIG. 13 D, a posterior view showing the deployed device 215, is the best vantage point for appreciating how the side-to-side sweeping action of the leading ends 218, 222 (indicated by the open arrows) results in dissecting the muscle I periosteum free from the attachments to the dorsal lamina, which has been labeled in this illustration. This step is critical inasmuch that the laminar anchors cannot be readily secured to the lamina if significant soft tissue remains. The advantage of the angles of the leading ends 218, 222 with respect to the shafts 219, 223 is best seen, however, in the side view provided by FIG. 13 E, in which it can be seen that these angles substantially emulate the angles of the laminae as these structures are angled posteriorly along their craniocaudal axis. The leading ends 218, 222 can therefore prepare adjacent laminae for receiving the anchors.

At this point, evaluation may show that the interlaminar space may be greatly reduced by the "shingling" of one lamina overlying another. This may significantly retard the ability to implant the CMIS in an atraumatic fashion; the surgeon may choose to distract the target motion segment, reducing the shingling effect and more clearly demonstrating the [target] caudal edge of the vertebrae.

This can, of course, be accomplished by a number of different mechanisms, including standard laminar distractors. However, a unique, useful, novel and nonobvious vertebral distractor is also disclosed in this application. This device 290 is comprised of a cranial segment 291 and a caudal segment 292, as demonstrated in an elevational view FIG. 14 A, and further illustrated in an exploded view FIG. 14 B. Each segment is provided with a leading end and a trailing end; the leading end 293 of the cranial segment 291 is an expanded configuration designed to be brought against the base of the caudal aspect of the cranial spinous process. The trailing end 294 of the cranial segment 291 is substantially piston-like designed to be disposed within a channel 298 in the leading end 296 of the caudal segment 292; this trailing end 294 is provided with corrugations 295 designed to be brought against corrugations 297 within that channel 298. This is suggested by the dotted lines indicating this coupling. These [corrugations] create a ratcheting mechanism, which is designed to maintain the position of the distraction device 290 during positioning between the vertebrae. The trailing end of the caudal segment 292 is provided with two projections 299, 300 which are configured to be brought against the base of the caudal spinous process. The projections 299, 300 of the trailing end are curved I directed slightly posteriorly to better engage the target areas of the caudal vertebra upon final position. The exploded view in FIG. 14 B better demonstrates the ratcheting mechanism created by the corrugations.

Figure 15:
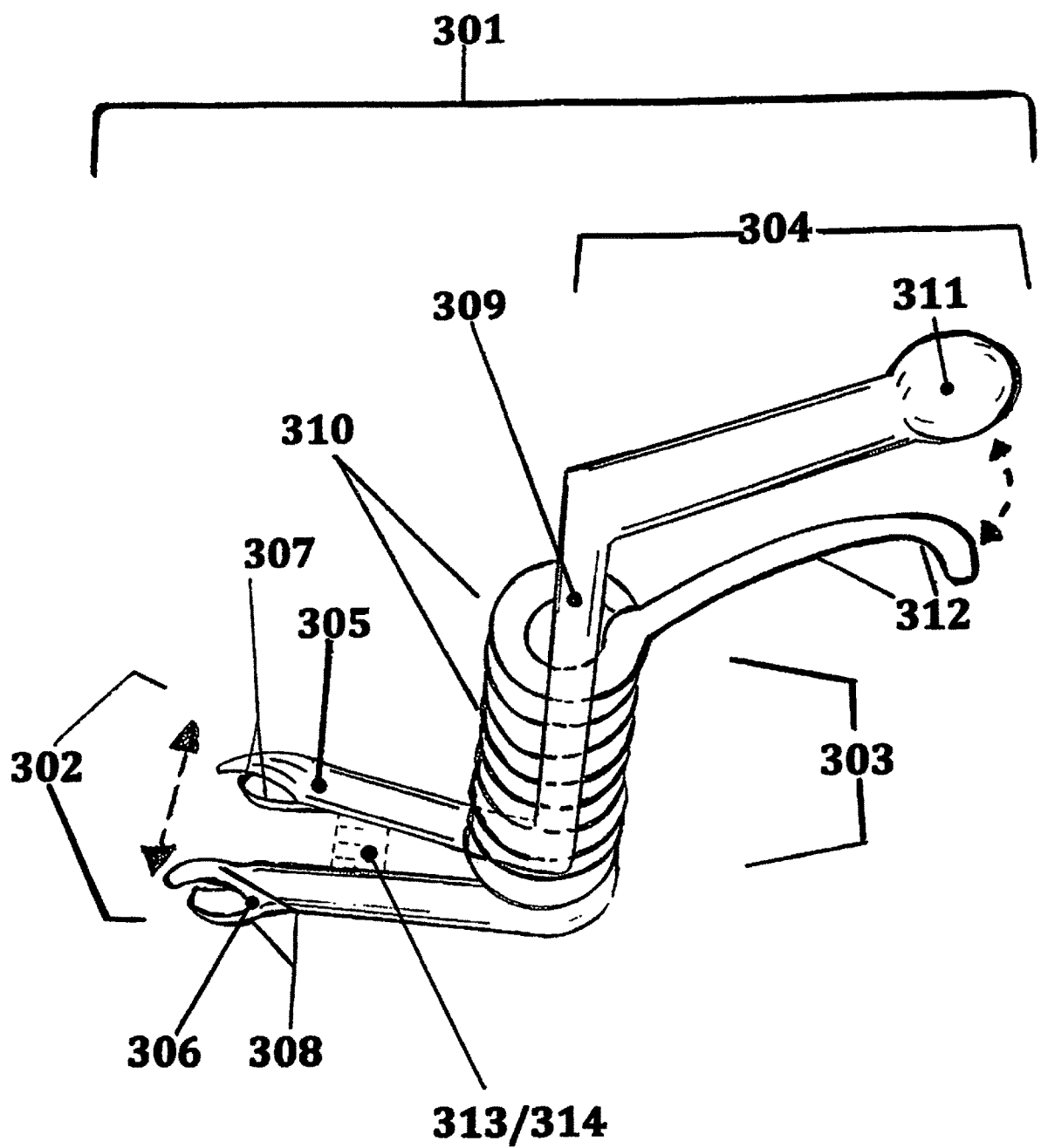
FIG. 15 is an elevational view of the instrument which inserts the distracting device in FIGS. 14 A & B into position.

FIG. 15 is an elevational view of the instrument 301 that positions the distractor device 290. This is designed so that the distractor 290 can positioned from a lateral approach during an MIS procedure.

Viewed from the elevational perspective in FIG. 15, the instrument 301 has a substantially sigmoid shape, and includes a leading end 302, central shaft portion 303, and a trailing end 304. The actuator of the instrument 301 is the trailing end 304, comprised of an active 312 arm and immobile 311 arm. The active arm 312 is continuous with a rotatable outer portion 310 of the central shaft 303, being then continuous with an active arm 306 of the leading end 302. Similarly, the immobile arm 311 of the trailing end 304 is continuous with an immobile central shaft 309, which is continuous with the immobile arm 305. The active aim 306 is provided with a plurality of so extensions 308 which reversibly couple with the cranial segment; the immobile arm 304 is also provided with a plurality of extensions 307, which stabilize the trailing end.

Compressing the active arm 312 of the trailing end 304 against the immobile arm 311 translates this actuation to the spiraling rotatable component 310 of the central shaft 303, which has a tensioned relationship with the immobile shaft 309. This causes the active arm 306 of the leading end 302 to be distracted from the immobile 305 (straight arrows) arms. The distractor 290 is loaded onto these arms 306, 305, and is deployed and positioned. Optionally, there may be a spring-loaded mechanism utilized. With deployment of distractor 290, there is distraction of the motion segment leading to enlargement of interspinous space.

Figure 16:
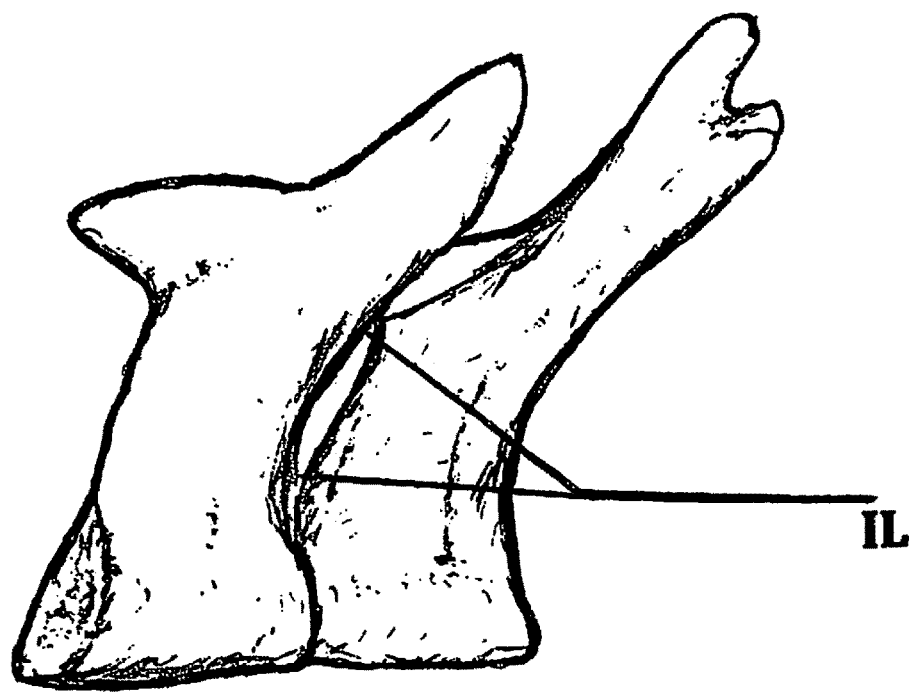
FIGS. 16 A-E show the pathology and the distractor device being placed and then expanded to achieve the desired effect.
Figure 16:
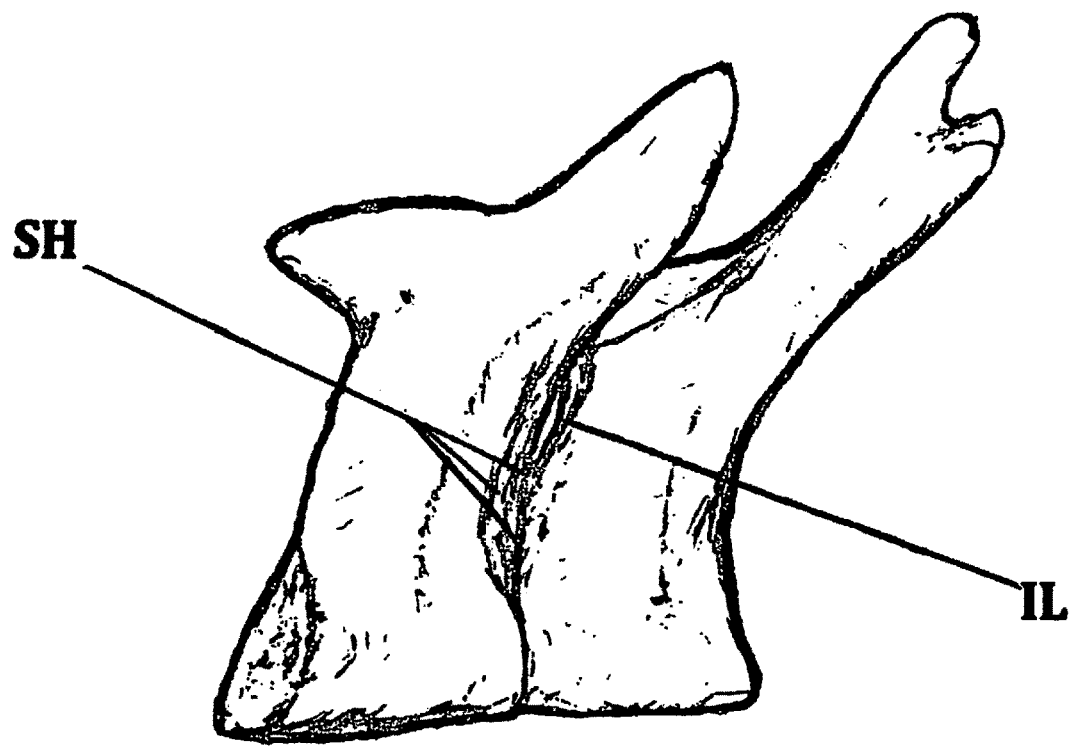
Figure 16:
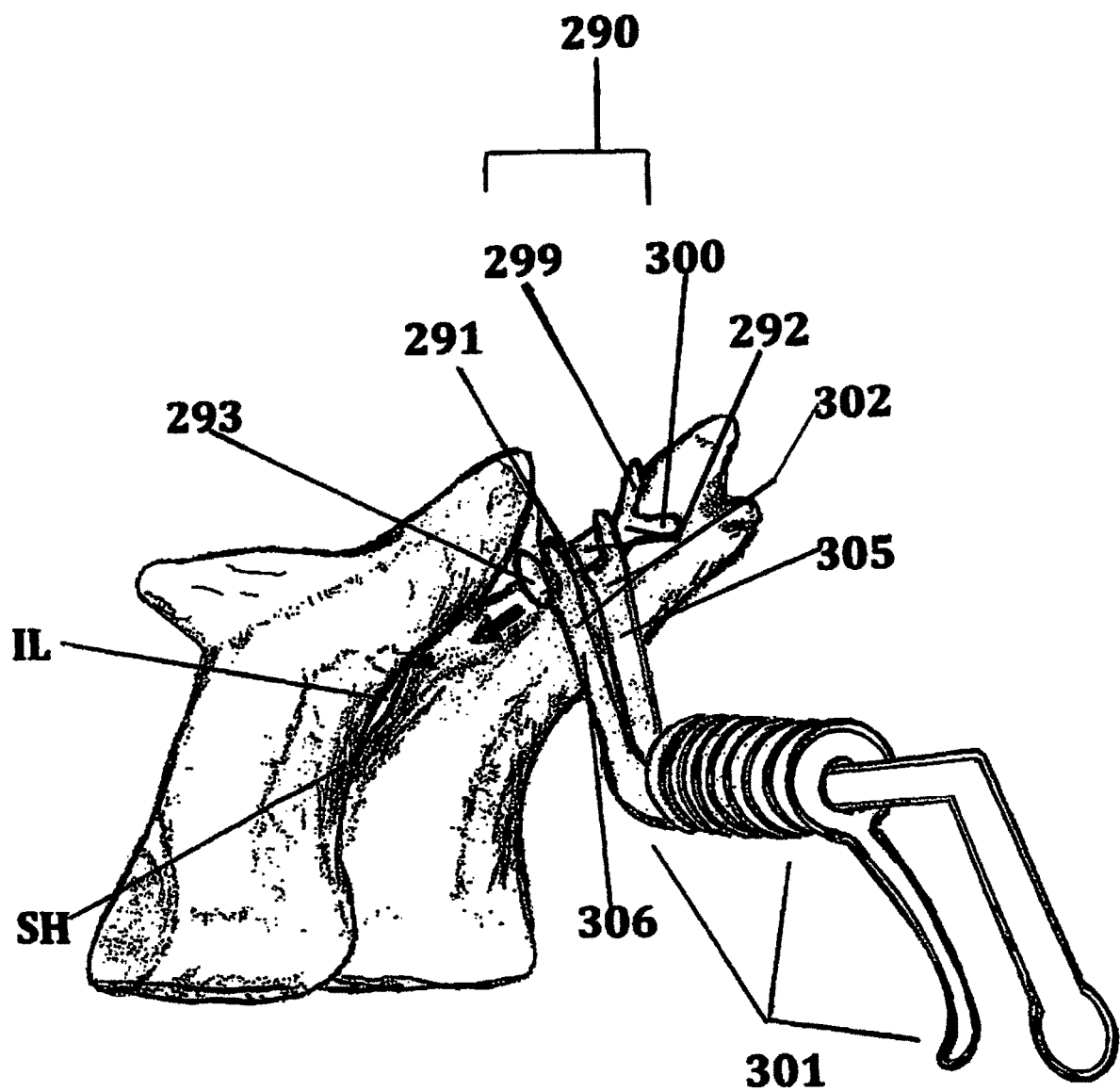
Figure 16:
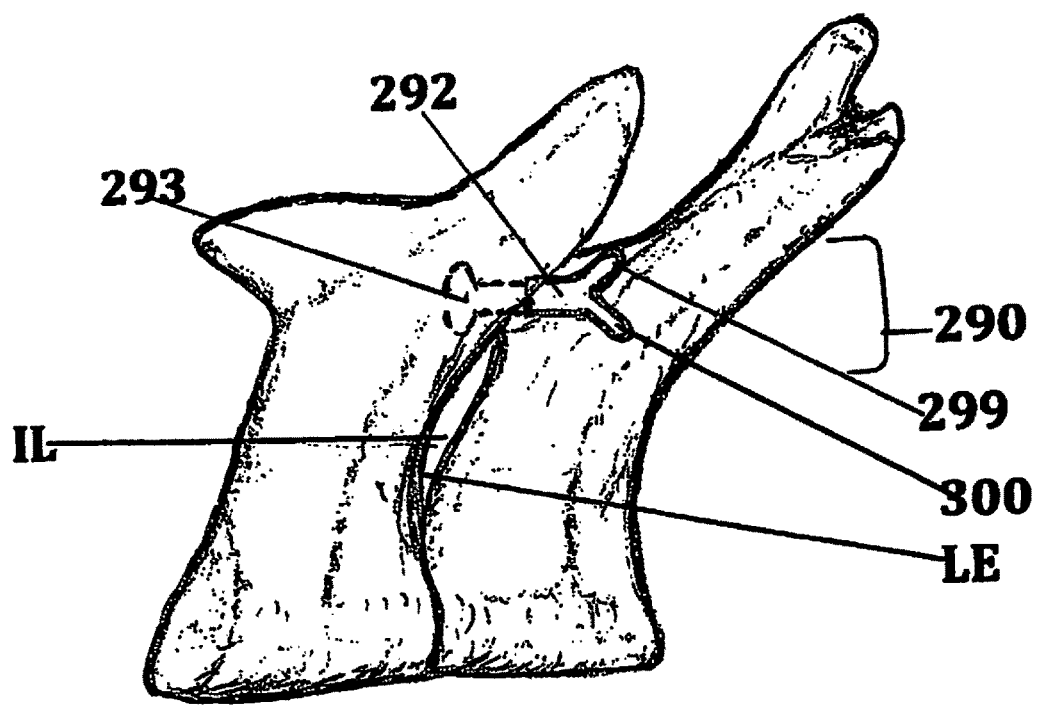
Figure 16:
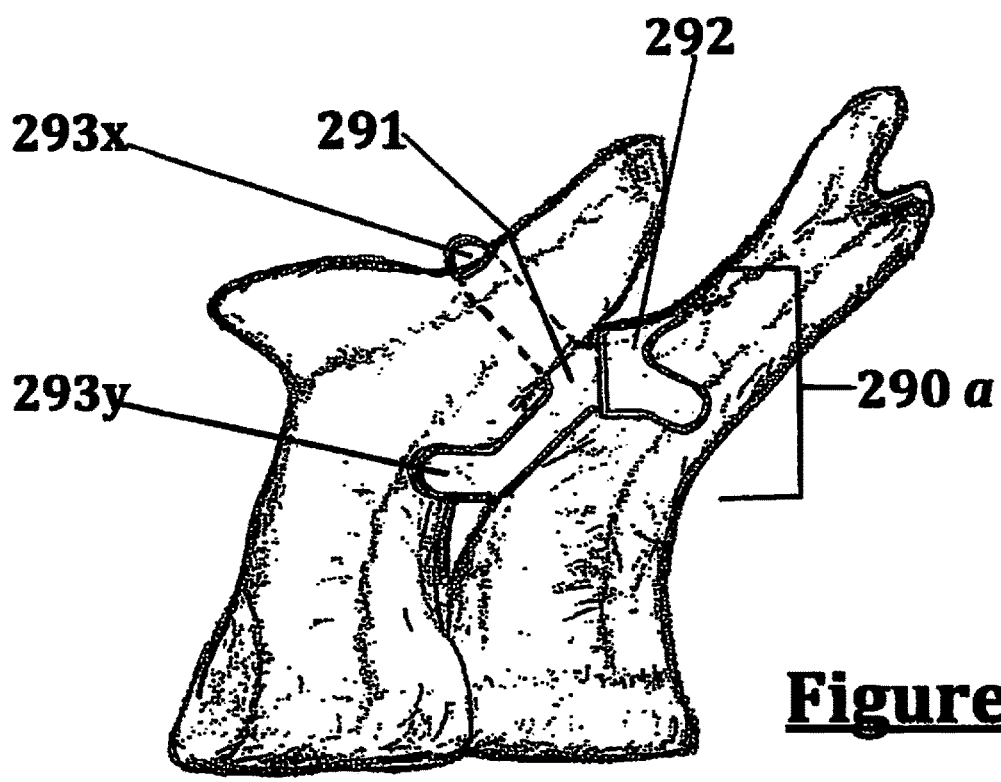

FIGS. 16 A I B are elevational views of normal (16 A) and pathological (16 B) posterior elements showing an exemplary motion segment. The most important feature is the [normal] interlaminar space IL, seen in FIG. 16 A, which clearly offers surgical access to the lateral aspect of the inferior edge of the cranial lamina. Using the same view, FIG. 16 B demonstrates the appearance of a diseased segment, with a greatly reduced interlaminar space IL resulting from the "shingling," effect SH; this greatly reduces access to the inferior laminar edge, hindering placement of the CMIS. The object of this device will be to distract the vertebrae of the motion segment, restoring I reopening the IL and making ideal placement feasible.

FIG. 16 C illustrates the application of the distractor 290 to an exemplary motion segment affected by "Shingling," SHand a reduced Interlaminar Space IL. The cranial segment 291 of the distractor 290 is stabilized with the mobile arm 306 of the instrument 301 while the immobile arm 305 stabilizes the caudal segment 292. The leading end 302 of the instrument 301 I distractor 290 complex is positioned by initially bringing its ventral surface against the cranial aspect of the caudal spinous process. The instrument 301 is passed from a lateral approach and rotated so as to dispose the instrument 301 I distractor 290 complex cranially along a curvilinear path (solid arrow) until the expanded leading end 293 of the cranial segment 291 is brought against the upper spinous process (stippled outline of open arrow) and caudal segment 292 is brought against the lower spinous process. Deployment of the instrument 301 compels the expanded leading end 293 to be firmly pressed against the cranial spinous process while the projections 299, 300 are brought against the lower spinous process.

Insertion and expansion of the device 290 results in distraction of the motion segment, as seen in FIG. 16 D. The leading end 293 is seen in relief (dotted lines) positioned against the posterior midsection of the cranial spinous process. The processes 299, 300 of the caudal segment 292 are seen positioned against the sides of the caudal spinous process. The interlaminar space IL is now several millimeters wider with exposure of the laminar edges LE, facilitating implantation of the CMIS. After the CMIS is in final position bilaterally, the distractor 290 is removed. FIG. 16 E shows an alternative embodiment of the device 290 a in which the cranial segment 291 is provided with a bifurcated end, demonstrating projections 293x I 293y that secure around the cranial spinous process. The caudal segment 292 is substantially identical to that seen in the standard embodiment.

Although this procedure utilizes "minimally invasive surgical" (MIS) techniques, it is desirable to have exposure of the limited area of the lamina to which the anchors will be secured. This exposure can be achieved with standard retractor systems, including cannula systems designed for MIS spinal procedures. These include art taught by Miles in multiple patents including U.S. Pat. No. 8,602,982, as well as that taught by DiPoto, Smith, Foley and others.

In attempting to achieve the needs and goals of such retraction, problems exist with much of the previous art. A major concern with the cannula systems taught by Foley and Smith in U.S. Pat. No. 5,954,635 and others is that the surgical access cannulas which are currently available are all substantially circular in configuration. However, the primary axis of this surgical procedure is in a craniocaudal direction; such cannulas engage a larger surgical field, particularly mediolaterally, than is necessary. MIS cannula access systems such as that taught by DiPoto, et al. in U.S. Pat. No. 7,766,930 are expandable, and can theoretically configure to the axis of the surgical field, but would be generally too large for use with the CMIS. The same is true for the art taught by Matthews, et al. in U.S. Pat. No. 6,206,826.

Another concern in retraction/gaining surgical exposure is the [steep] angle of the medial aspect of the lamina as it is continuous with the base of the spinous process. This can be fairly acute such that some retractor systems can be rotated by this angle.

The ideal retractor for this scenario is one that accommodates the medial laminar angle, selectively provides craniocaudal exposure, is initially positioned in the collapsed embodiment and then expanded just sufficiently to expose the target areas. Additionally, the ideal retractor is manufactured from a hard plastic or other substance which is substantially radiolucent, so as to not create artifacts on imaging. Ease of use is, of course, prerequisite.

To this end, disclosed herein is a unique, useful, novel and nonobvious retractor system 230. This is demonstrated in a lateral elevational view in FIG. 17 A, showing it is comprised of a medial blade 231 and a lateral blade 232; these are connected to a cranial articulating complex 233 and a caudal articulating complex 234. These are, in turn, comprised of [cranial] medial 238 and lateral 239 pivoting blades that are reversibly coupled to a central axial pin 237, as well as [caudal] medial 248 and lateral 249 pivoting blades again reversibly coupled with a central axial pin 255. Crucially, the medial blade 231 is a complex structure comprised of a major blade 235 and a minor blade 236 which can retract into the major blade 235; the advantage of this feature will be elucidated in FIG. 17 H below. Corrugations 262 contribute to a mechanism described below in FIGS. 17 F, 17 G which locks the retractor and blades in place once brought into position. Optionally, at the bases of the medial and lateral blades, a series of small foot plates 260, 283 that interface with the muscle and maintain the position of the retractor can be provided.

Figure 17:
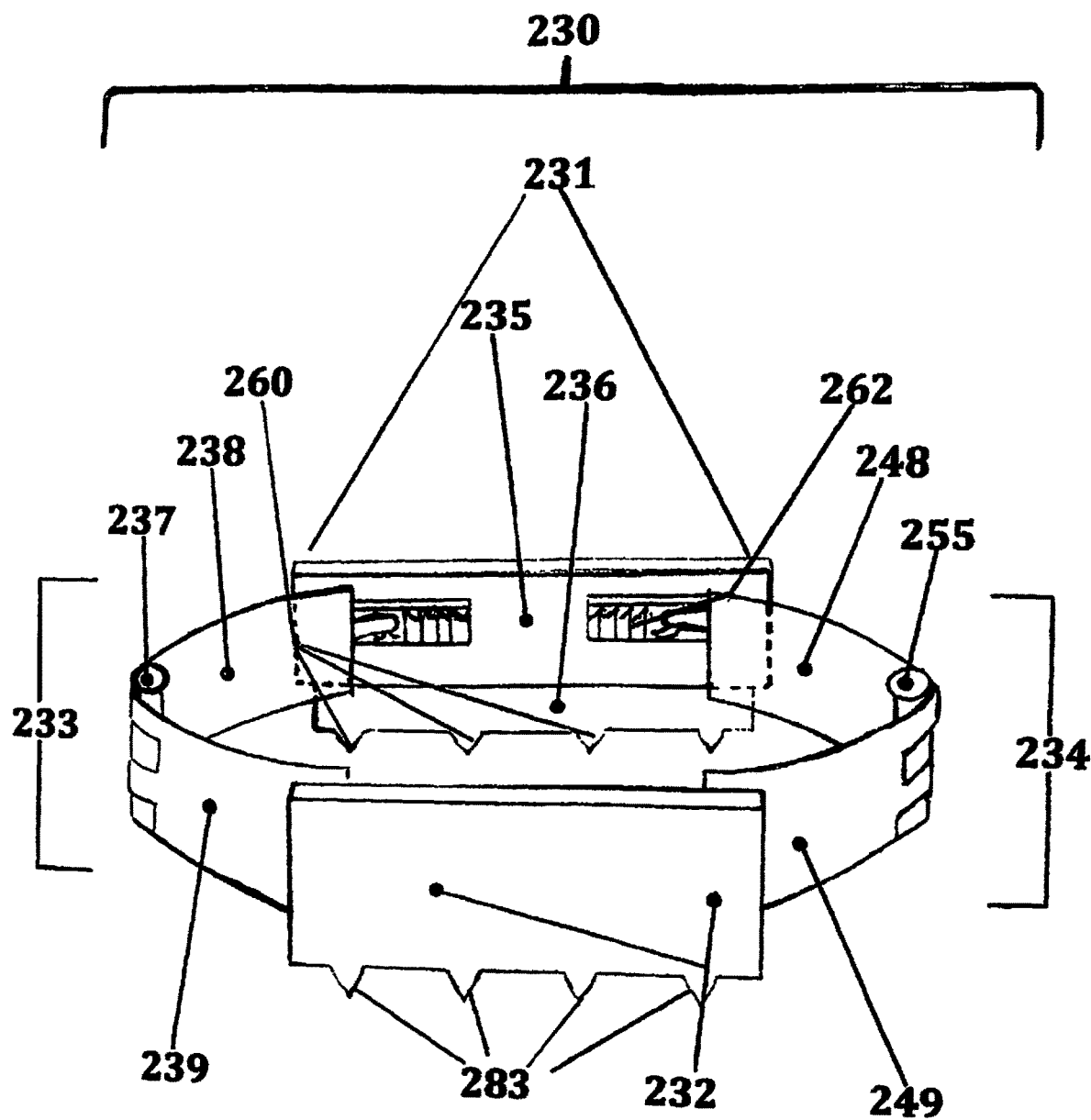
FIGS. 17 A-H display a retractor system uses to facilitate implantation of the CMIS.
Figure 17:
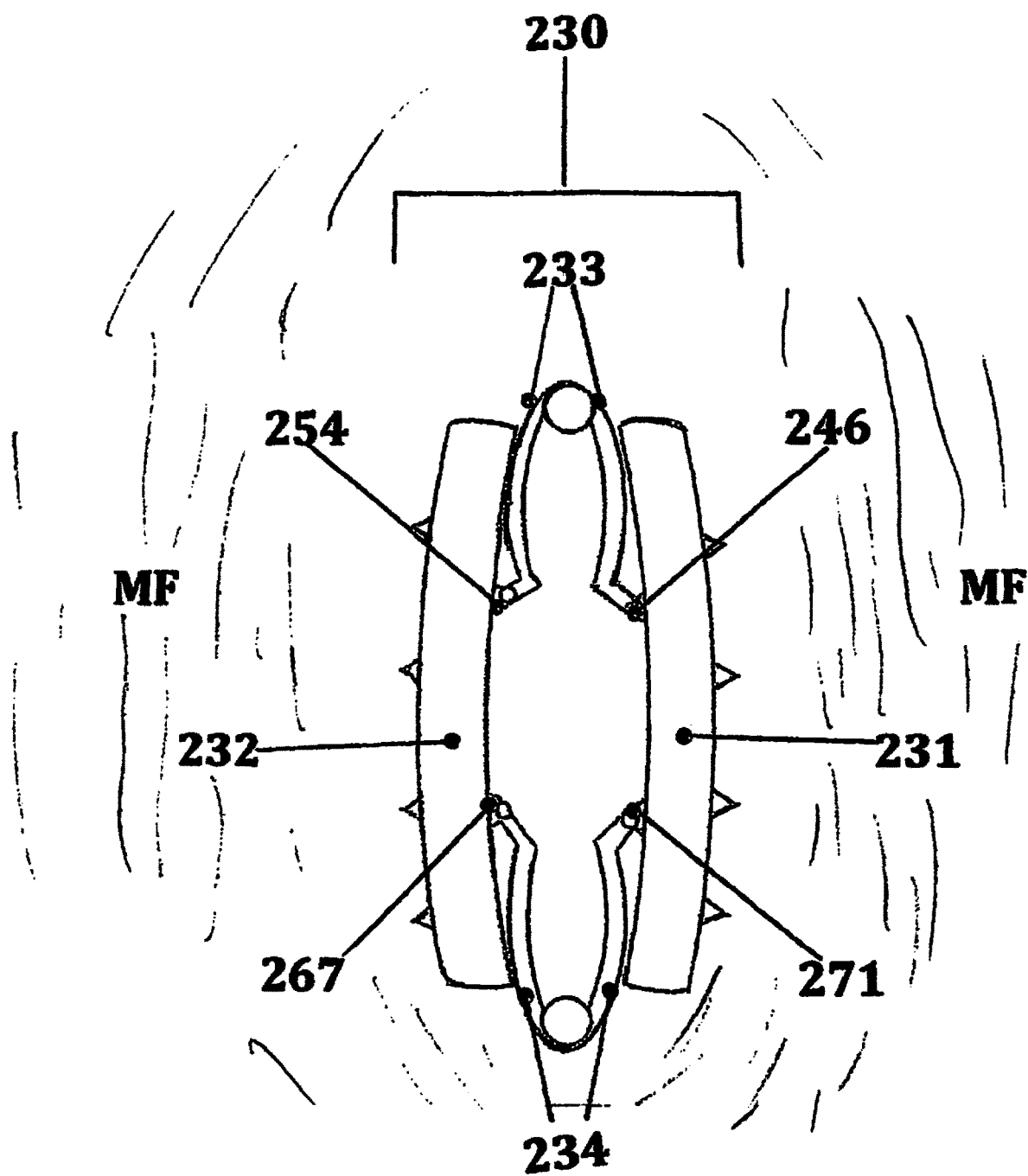
Figure 17:
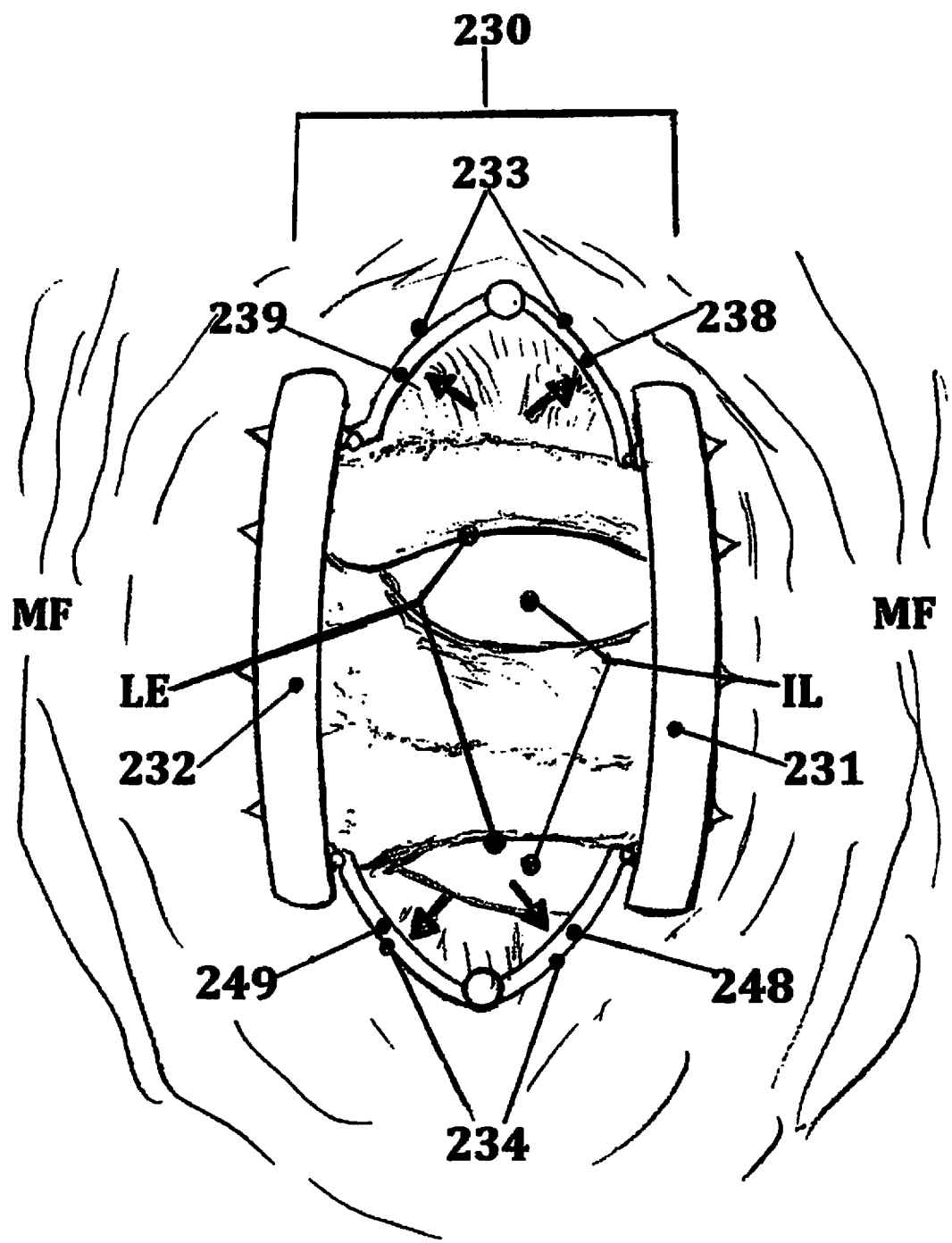
Figure 17:
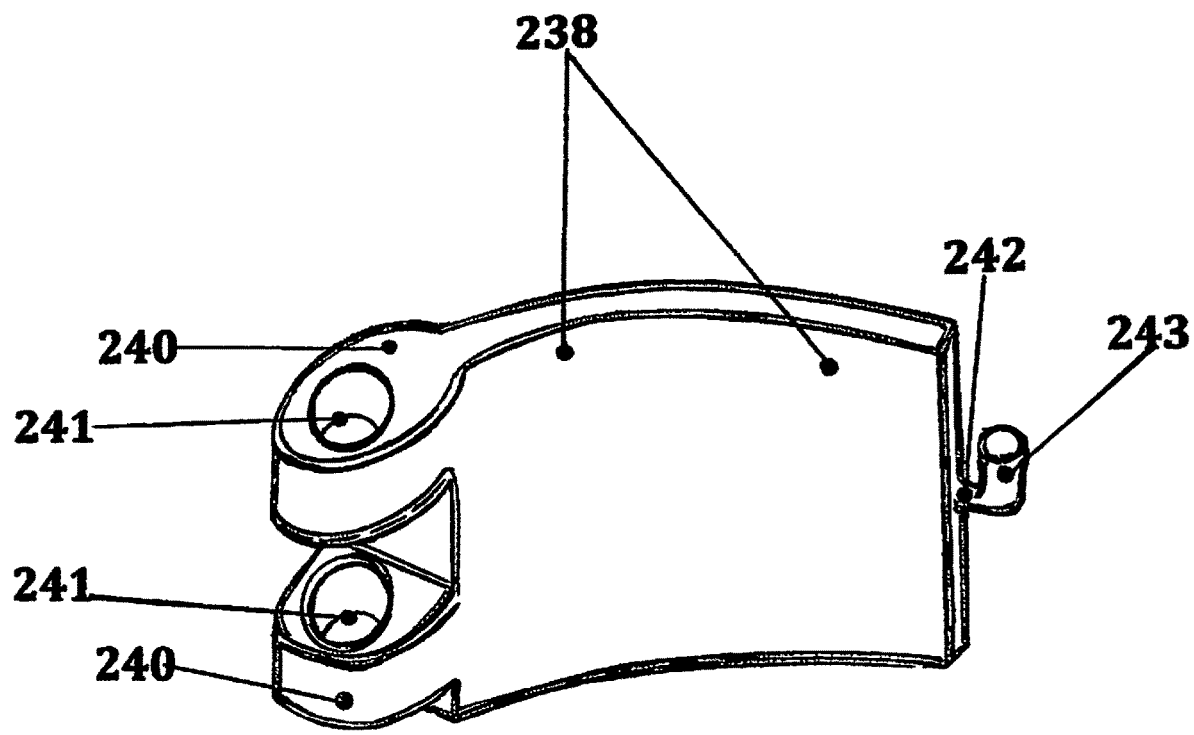
Figure 17E:
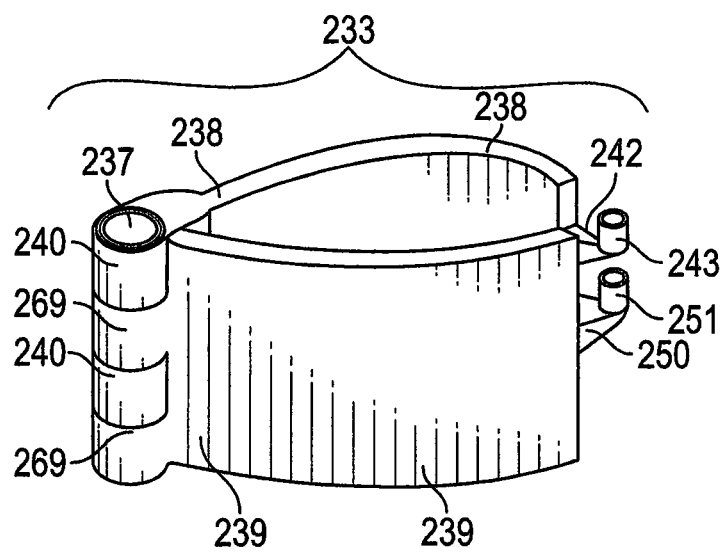
Figure 17F:
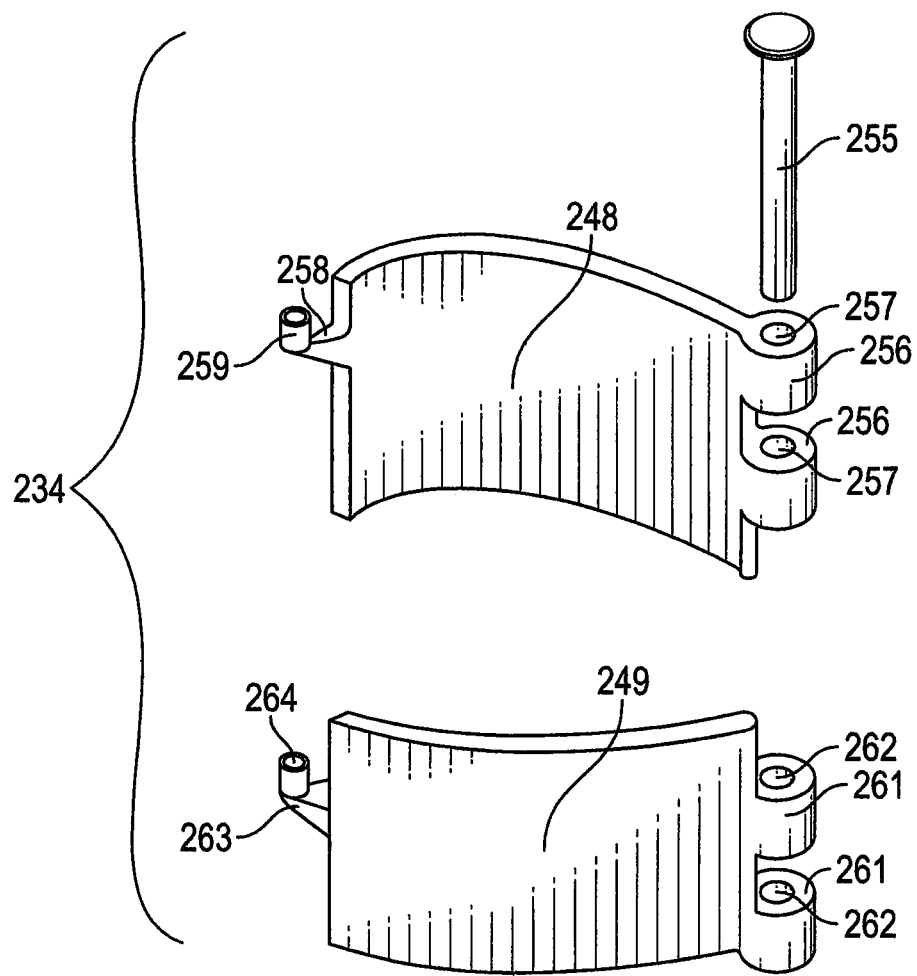
Figure 17G:
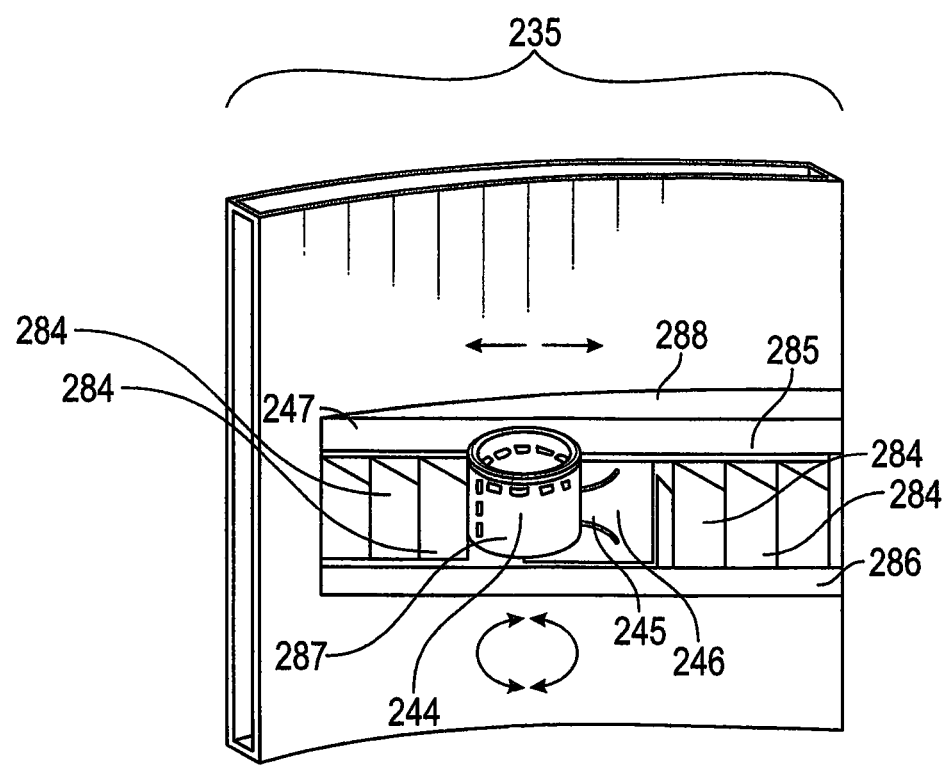
Figure 17:
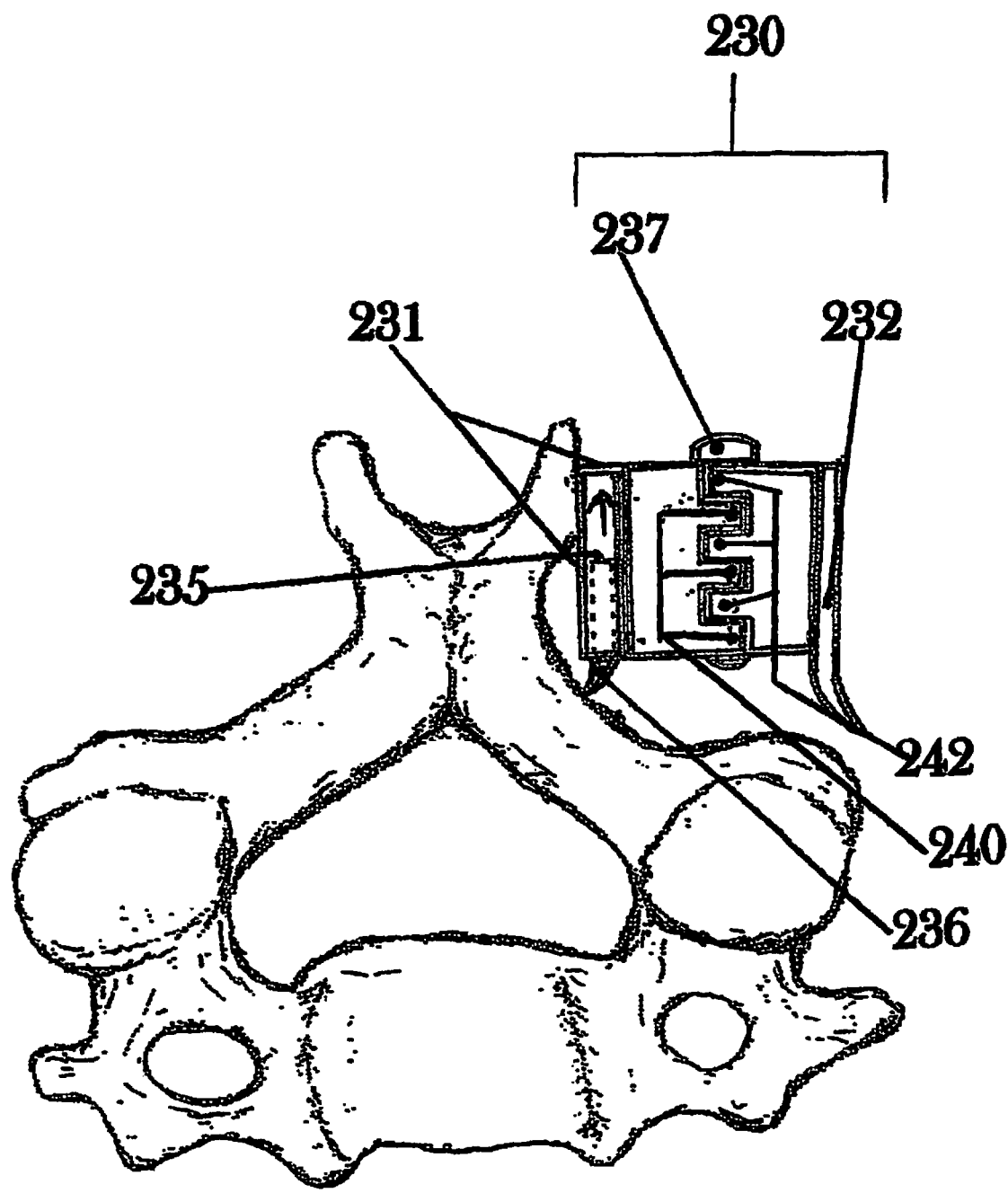

Deployment of this retractor is best appreciated by top views of the device in the primary (FIG. 17 B) and deployed positions (FIG. 17 C). As would be seen by the surgeon, the retractor 230 is initially positioned in the primary I ollapsed I non-deployed position such that the cranial 233 and caudal 234 articulating complexes are completely collapsed, carriages 246, 254, 267 and 271, are positioned close to the middle of the medial 231 and lateral 232 retractor blades which are approximating each other. This configuration allows the retractor 230 to be insinuated between the muscle fibers MF which have been split as per FIGS. 13A-E. The retractor 230 is then deployed I opened, maximizing the exposure as in FIG. 17 C by actuating the articulating complexes 233, 234, which cause the cranial 238, 239 and caudal 248, 249 pivoting blades to be repositioned (indicated by the solid arrows). This in turn, compels the medial 231 and lateral 232 blades to become divergent and create the necessary exposure. One notes interlaminar spaces IL and laminar edges LE in the field; since two caudal laminar edges are exposed, this would accommodate placement of a single level CMIS.

FIG. 17 D is an elevational view of the cranial medial blade 238, exemplary of the blades of the articulating complexes 233, 234, and further illuminating their function. Here it is noted that this monolithic structure is provided with a leading end, an expanded central blade-like segment and a trailing end. The leading end is provided with an extension 242 which is continuous with a rounded column 243 that reversibly couples with an extension from the medial blade, this coupling creating a mechanism rendering the retractor to be repositionable in the mediolateral plane. The blade maintains the position of retracted soft tissues. The trailing end is provided with rounded extensions 240 that have central apertures 241, accommodating the pin to assemble the cranial articulating complex 233.

The cranial articulating complex 233, illustrated in FIG. 17 E, is comprised of a central axial pin 237 which is reversibly, rotatably coupled to medial and lateral pivoting blades 238, 239 by passing the pin 237 through apertures in extensions 240, 269 at the trailing ends of the blades 238, 239. Extensions 242, 250 from the leading ends of these blades terminate in rounded columns 243, 251 that will be reversibly coupled with components of the medial and lateral blades 231, 232, this coupling being essential to the mobility of the retractor.

The caudal articulating complex 234 is a mirror image of the cranial complex; this is demonstrated in an exploded view in FIG. 17 F. Medial 248 and lateral 249 pivoting blades include a plurality of extensions 256 and 261, respectively, that are provided with apertures 257 and 262 through which the central axial pin 255 is disposed (as indicated by black arrows) to couple with these blades, allowing the blades to rotate around this pin. Furthermore, the retractor can be disassembled when no longer needed by removing this pin, which then releases the blades and permits rapid removal of the components. Extensions 258, 263 on the leading ends of blades 248, 249 are continuous with rounded columns 259,264 that couple with the medial and lateral blades.

A slidable, ratcheting mechanism is critical in the deployment of the retractor. An example of this mechanism is reviewed in FIG. 17 G, a lateral elevational view of the internal surface of the cranial half of the major blade 235. One notes a horizontally oriented tract 247 with a series of corrugations 284. This tract 247 is straight in this example, this geometry accomplished by a monolithic extension 288 from the blade surface. The slidable element is a [cranial] carriage 246 which is irreversibly coupled by superior 285 and inferior 286 edges to the tract 247. This feature promotes movement of the carriage 246 in a craniocaudal direction along the course of the tract 247, as indicated by the large open arrows. More critically, initially positioning such carriages in the middle of the tracts promotes maximal collapse of the retraction for insertion; translation of the carriages towards the ends of the tracts I blades occurs with deployment. The carriage 246 is also provided with corrugations (on its undersurface I not shown) which interface with corrugations 284 of the tract 247, creating a ratcheting mechanism which locks the carriage 246 in place upon positioning the retractor. An extension 245 arises from the carriage 246 and terminates in a cylinder 244 configured with a chamber 287 (shown in relief as demarcated by the interrupted line). This chamber 287 accommodates a column on the leading end of the cranial medial pivoting blade (also not shown) thus reversibly coupling with this blade. This coupling confers rotational movement of the column within this chamber 287, that freedom of this rotation illustrated by the circular solid arrows below the cylinder 244. This rotation accommodates the changing angles of the medial pivoting blade as the retractor is deployed. This entire mechanism accomplishes the objects of the invention including the ability of the retractor to be reconfigured and locking the retractor in place.

Another critical feature of this retractor 230 is the unique configuration of the medial blade 231, composed of a major blade 235, which is provided with a slotted chamber that permits a minor blade 236 to be slidably repositioned therein, as seen in a frontal I transaxial perspective in FIG. 17 H, which shows the application to an exemplary CS vertebra. This blade 236 may also be provided with one or more curved footplates 260. Multiple other embodiments can be envisioned, all of which would be considered within the spirit and scope of the invention.

This adjustable dimension facilitates intraoperative placement of the retractor. The medial element 231 is easily positioned by the vertical adjustability of the minor blade 236. The exact position of the retractor 230 is often variable is accordance with factors such as individual anatomy, surgeon preference, and other factors. A monolithic blade can be incorrectly sized, which can cause an imbalance in the retractor system used. Conversely, as demonstrated here, as the medial blade 231 is positioned, it can be appropriately adjusted in accordance with the angle of the lamina as it ascends towards the spinous process. The lateral element 232, as also seen in FIG. 17 H, does not require this level of adjustability, and is comprised of a single blade. The medial 231 and lateral 232 elements are respectively coupled with the medial 238 and lateral 239 pivoting blades, which in turn give rise to the intersecting extensions 240, 242 which are locked by the central axial pin 237.

Figure 18:
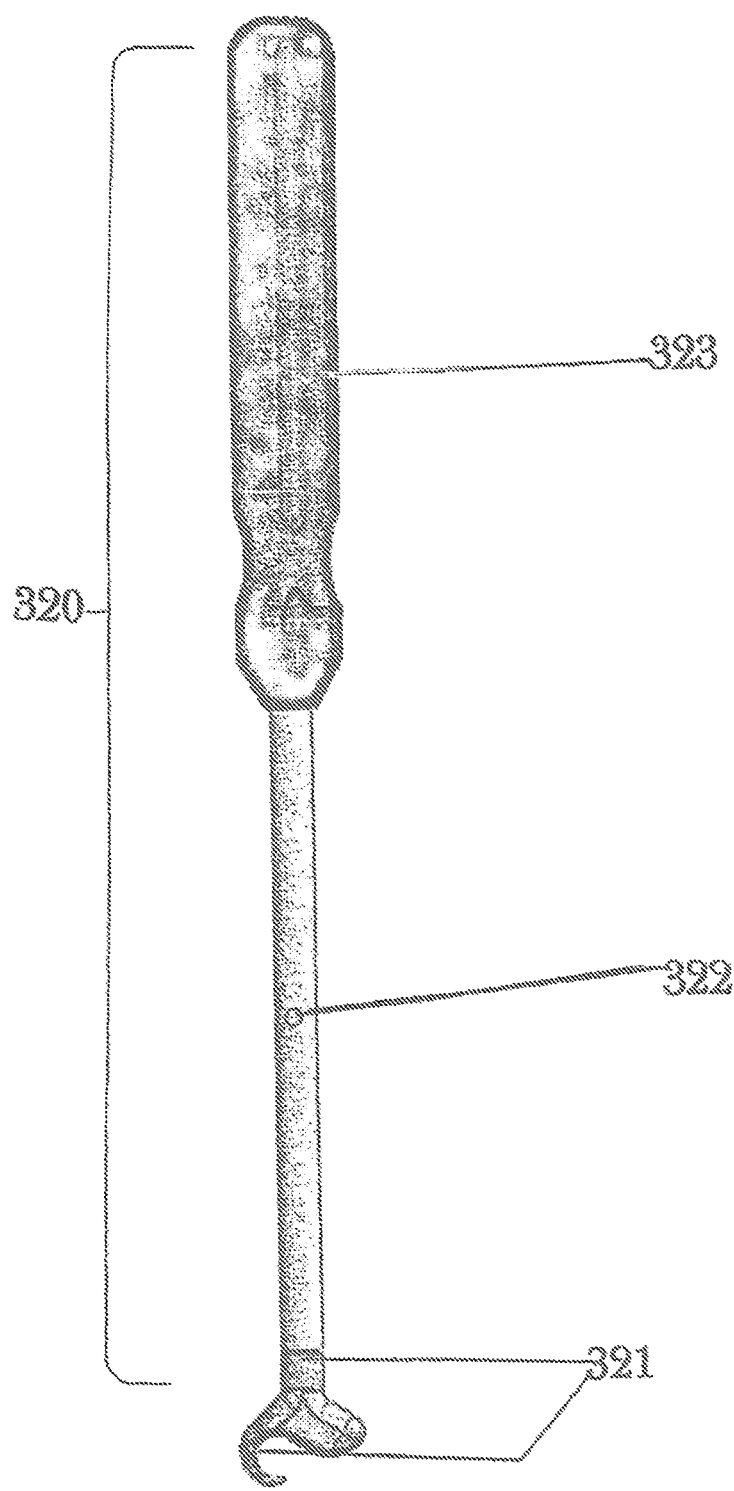
FIGS. 18 A/B depict a lateral view of an instrument to prepare the lamina to receive the anchor and a lateral cut-away view of the ligamentum flavum being dissected free.
Figure 18:
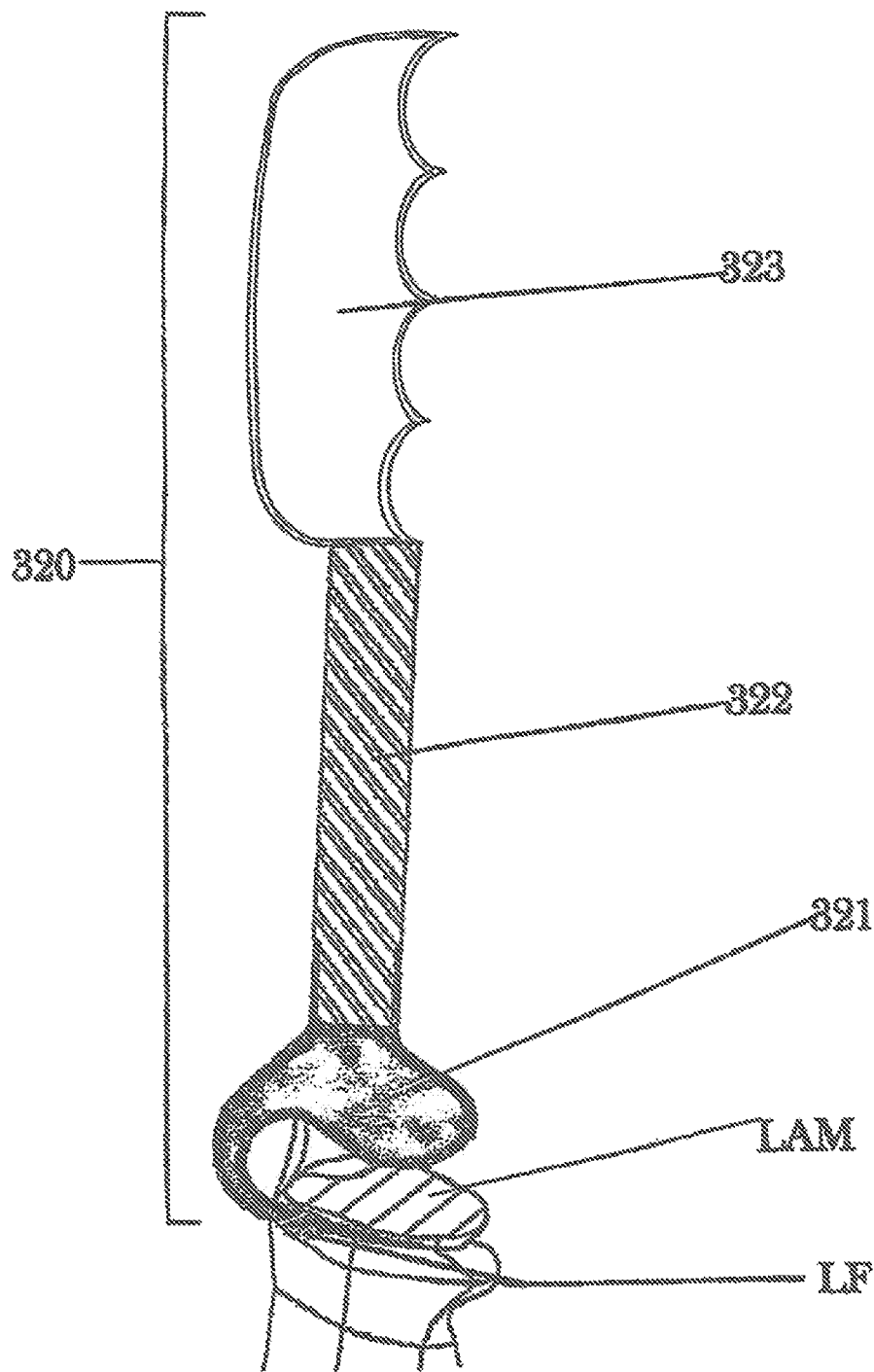

As a next step, the ligamentum flavum must be dissected from the underside of the lamina to receive the anterior jaw of the laminar anchor. A unique, useful, novel and nonobvious ligament release instrument 320, shown in FIG. 18 A, is provided to achieve this. This instrument is provided with a curved leading end 321 which can be insinuated safely under the lamina without concern of "plunging" into the canal and irritating the neural elements. The leading end is further protected by the prominent overhang which is brought against the dorsal lamina to further ensure that there is no "plunging," of the leadingmost end. The instrument 320 is continuous from the leading end 321 through the shaft 322 to the trailing end 323; the latter is a handle used by the surgeon to manipulate the instrument 320. FIG. 18 B is a hemisection of a representative lamina Lam showing the leading end 321 releasing the attachments of the ligamentum flavum LF. By gently rocking the handle 323, a reciprocal movement is transmitted to the leading end 321, allowing it to be brought against the lamina and then carried along the anterior face of the lamina, developing a plane between the lamina and ligamentum flavum LF.

Figure 19:
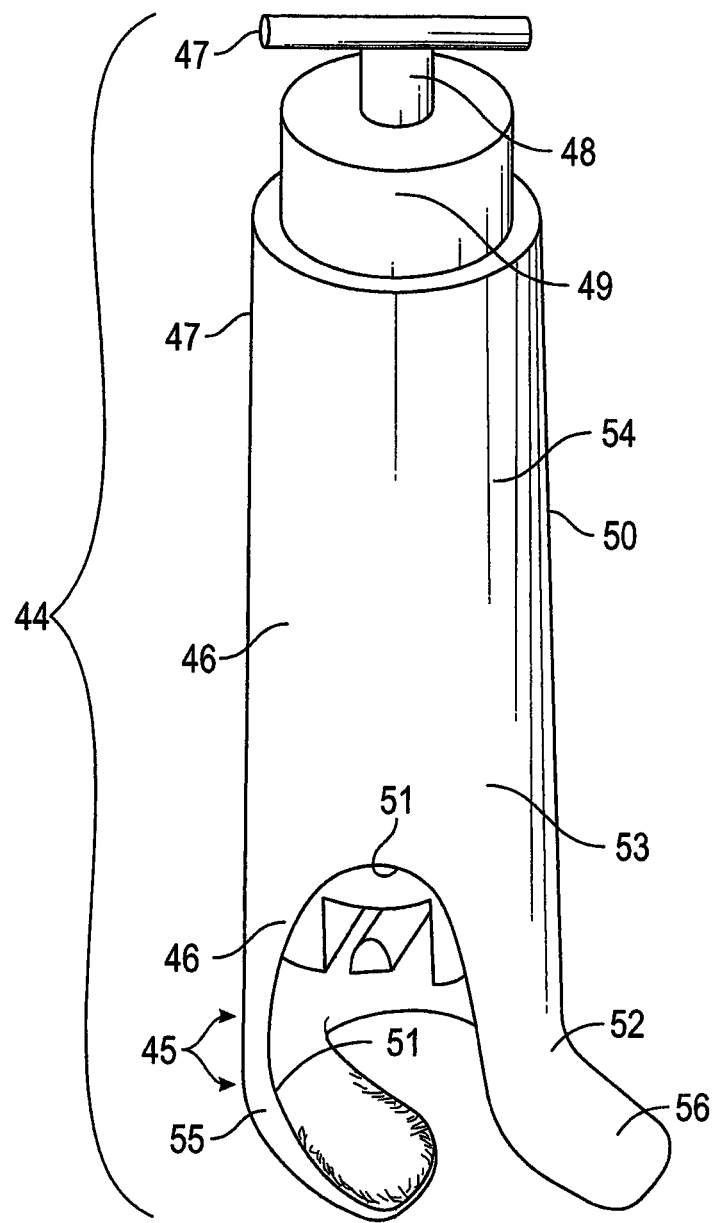
FIG. 19 is an elevational view of the implantation instrument.
Figure 20:
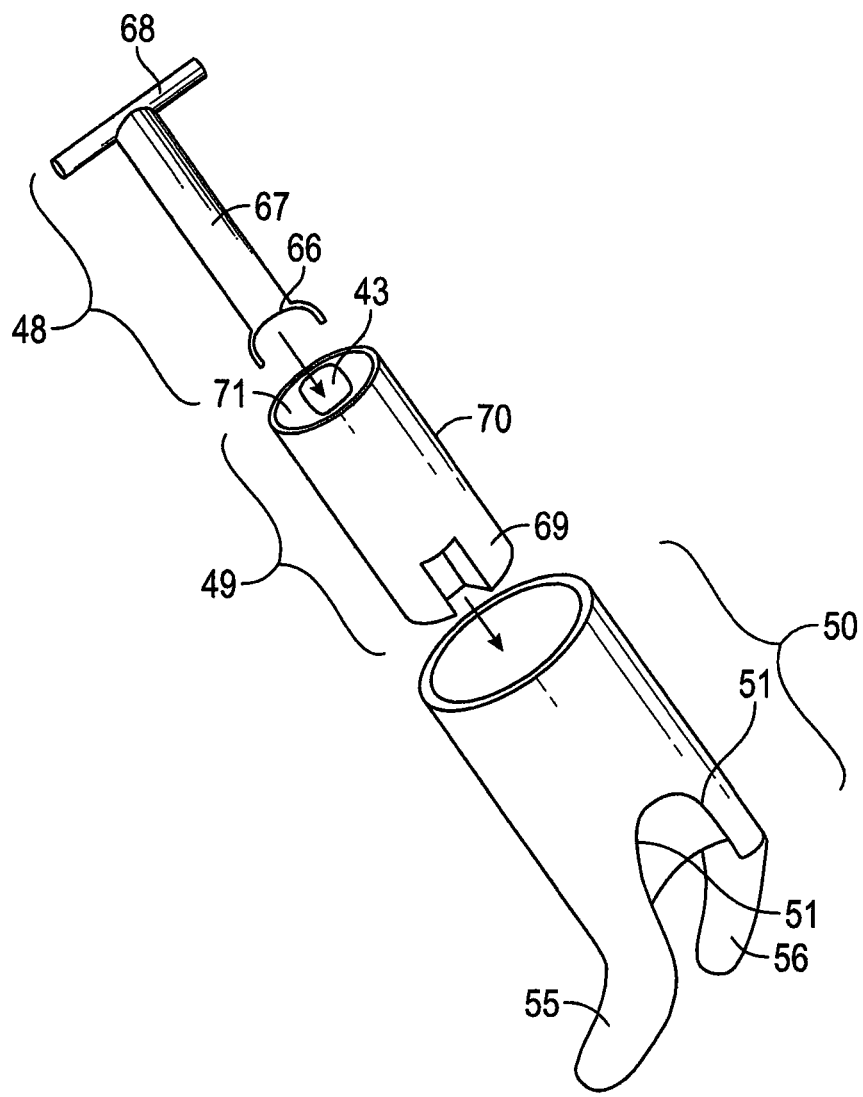
FIG. 20 shows an exploded view of the implantation instrument.

In the preferred and most alternative embodiments disclosed herein, this unique, useful, novel and nonobvious system for stabilizing the cervical spine is secured to the target motion segment by implanting bilateral laminar anchors and coupling these with a connecting element. To achieve these ends, a device known hereinafter as the implantation instrument 44 undertakes multiple functions, including directing the anchor into the ideal position against the lamina, tightening the securing screw, and coupling the connecting element to the anchor. This instrument is disclosed in FIG. 19, a posterior elevational view of the instrument 44, and FIG. 20, an elevational, exploded view. Although FIG. 19 reveals that this instrument 44 is provided with an overall leading end 45, central shaft 46 and trailing end 47, further scrutiny demonstrates that this is a complex instrument 44 provided with a central trocar 48, an inner cannula 49 and an external cannula 50. This external cannula 50 also has a leading end 52, a central shaft 53, and a trailing end 54, with the leading end 52 provided with two additional features critical to achieving the goals of the invention: firstly, a cutaway 51 through which the connecting element is disposed in order to couple with the anchor being implanted; secondly, medial 55 and lateral 56 grasping arms are present to achieve the primary task of the instrument 44, that is to stabilize the laminar anchor during implantation. To this end, the laminar anchor can be "pressure fit," between them, and held in place during implantation. In FIG. 19, it is noted that the interior surface of the medial grasping arm 55 is contoured to accommodate the posterior jaw of the laminar anchor. When the screw of the anchor is tightened, driving the jaws of the anchor towards one another, the overall profile of the anchor is reduced thus relaxing the pressure fit. Once the anchor is securely attached to the target lamina, the instrument 44 is removed leaving the anchor in its desired position. In the preferred embodiment, the grasping arms 55, 56 are configured to hold the anchor at a bias (as demonstrated in FIGS. 19 I 20) consistent with the angle of the lamina, thus making implantation more efficient. Other, more mechanically complex embodiments to hold the anchor in place can be contrived and anticipated by those knowledgeable in the art; all such embodiments would be within the spirit and scope of this invention.

The anchor is attached to the lamina by tightening the securing screw, which compels the jaws towards each other, grasping the lamina between them. In the preferred embodiment, this is accomplished by tightening the horizontal bar at the trailingmost end of the screw; it can also be accomplished by providing the perimeter of the trailing end of the screw with a configuration such as a hexagonal profile on top view which can be rotated by a wrench. Obviously, combinations of these techniques can also be envisioned. This function of the implantation instrument 44 is accomplished by the central trocar 48 pictured in FIG. 20, an exploded view of the implantation instrument 44, which shows the central trocar 48 is provided with a leading end 66 configured to engage the horizontal bar, a shaft 67, and a trailing end I handle 68. The leading end 66 is disposed through a central channel 43 of the inner cannula 49, as indicated by the small, closed arrow, positioning the leading end 66 to engage the horizontal bar. Once the anchor is positioned against the lamina, the trailing end 68 of the trocar 48 is actuated, turning the leading end 66 tightening the screw. This will cause the jaws to move towards each other and create a secure gasp on the target lamina A sequence of thresholds within the instrument will create a first and second sound; with the first audible sound, the horizontal bar will be oriented in a generally craniocaudal direction, and ideally positioned for engaging the leading end of the connecting element. With engagement of that leading end, the horizontal bar is rotated another approximately 90°, and a second audible indicator is heard assuring the system is locked. Indicating the position of the horizontal bar can also be achieved by external markers on the cannula. In fact, those knowledgeable in the art can anticipate other and different systems for accomplishing this goal; all such embodiments are incorporated within the spirit and scope of this invention.

The implantation instrument 44 also captures the leading end of the connecting element and secures it to the trailing end of the securing screw. This is achieved by the inner cannula 49, which is also provided with a leading end 69, a shaft component 70, and a trailing end 71, also seen in FIG. 20. This cannula 49 is positioned within the outer cannula 50 in the assembled instrument 44, as indicated by the larger open arrow, with the leading end 69 dorsal to the cutaway 51 of the external cannula 50. This leading end 69 is configured to capture the flattened leading end of the connecting element and reposition it so that the horizontal bar can be disposed through the aperture in the leading end, that bar then rotated to cinch the connecting element into place, as will be demonstrated in FIG. 22.

Figure 21:
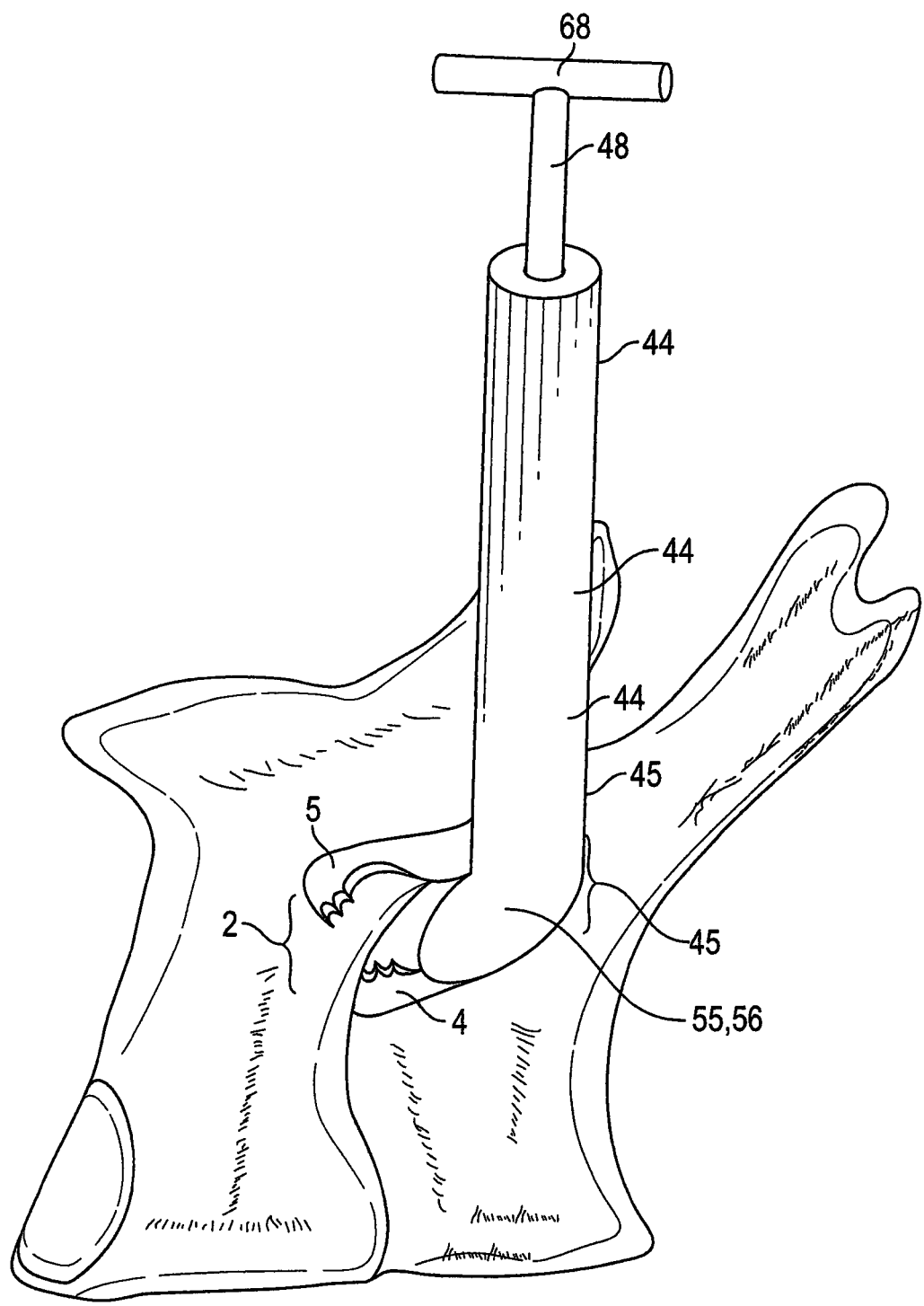
FIG. 21 illustrates the cranial laminar anchor being implanted.

FIG. 21 is a lateral elevational view of the left side of a posterior cervical motion segment demonstrating the implantation instrument 44 positioning a cranial laminar anchor 2. The anchor 2 is reversibly coupled with a slight anterior bias to the grasping arms 55, 56 of the leading end 45, aligning the anchor favorably with the bias of the target lamina, being introduced along its caudal aspect. The sublaminar jaw 4 is insinuated beneath the lamina, in preparation for securing the jaws 4, 5. The trailing end 68 of the central trocar 48 will be used to actuate the securing of the screw which locks the anchor 2 in position.

The caudal anchor 2a is then secured to the caudal lamina CDL LAM in the same fashion. The connecting element 3 (shown as an interrupted line outline) then couples the two anchors 2, 2a to form a right-sided CMIS 1 construct, as shown in a posterior view in FIG. 22 A. Upon passing the caudal anchor 2a into position, the securing screw 6a was tightened and the implantation instrument was removed. At that point, the housing mechanism 78 of the connecting element 3, which is slidably connected to the dorsal jaw 5a of the caudal anchor 2a, can be translated in a craniocaudal direction so as to accommodate passing the leading end 74 of the connecting element 3 through the cutaway 51 of the external cannula 50 of the implantation instrument 44 which has implanted the cranial anchor 2. Once the leading end 74 is in ideal position, the surgeon may adjust the cranipcaudal dimension by compression or distraction; then the securing screw 88 of the housing mechanism 78 of the connecting element 3 is locked, securing the connecting element 3 in position.

Figure 22:
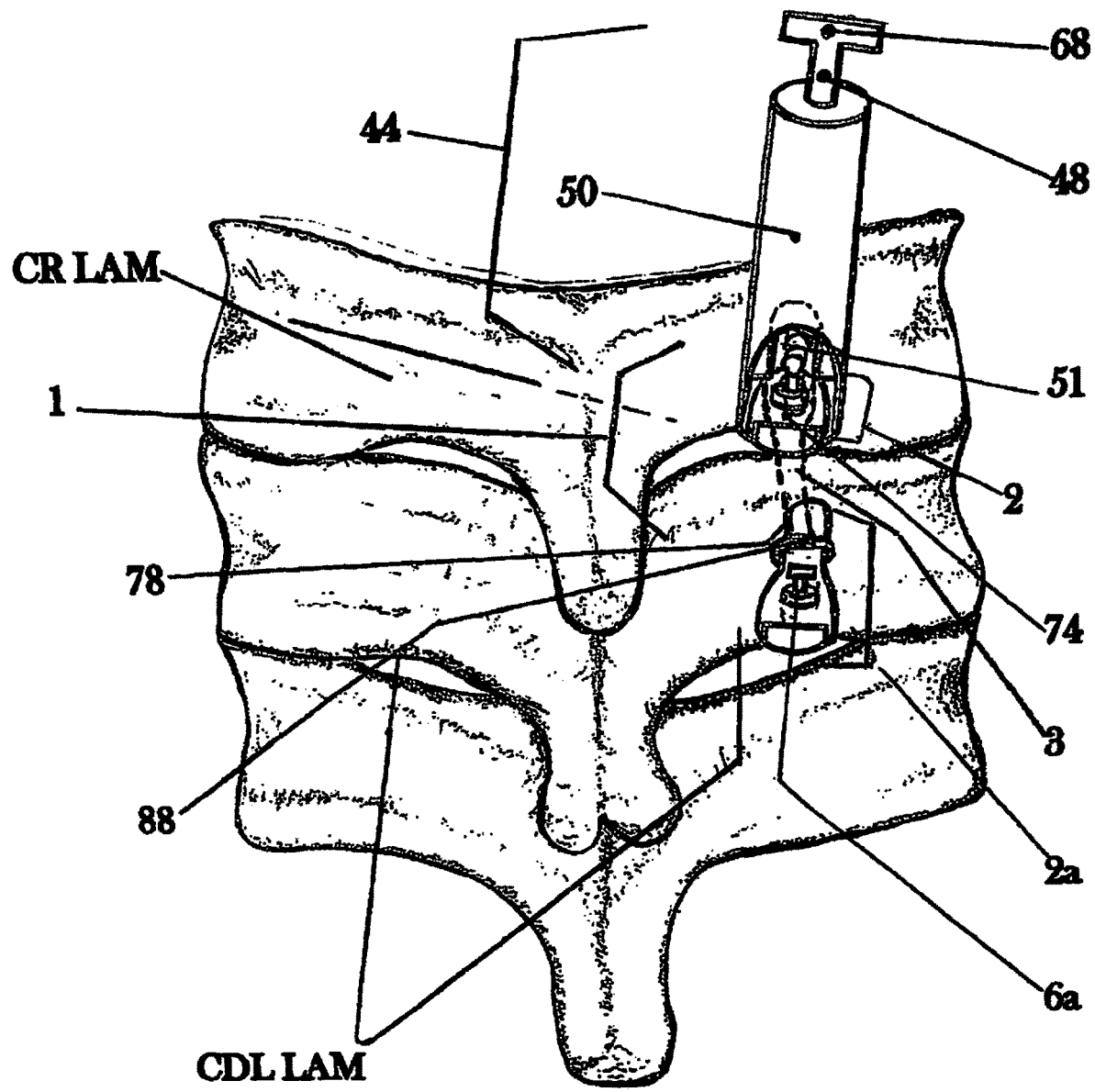
FIG. 22 A/B demonstrate the caudal laminar anchor being implanted, and the connecting element being secured to the cranial anchor.
Figure 22:
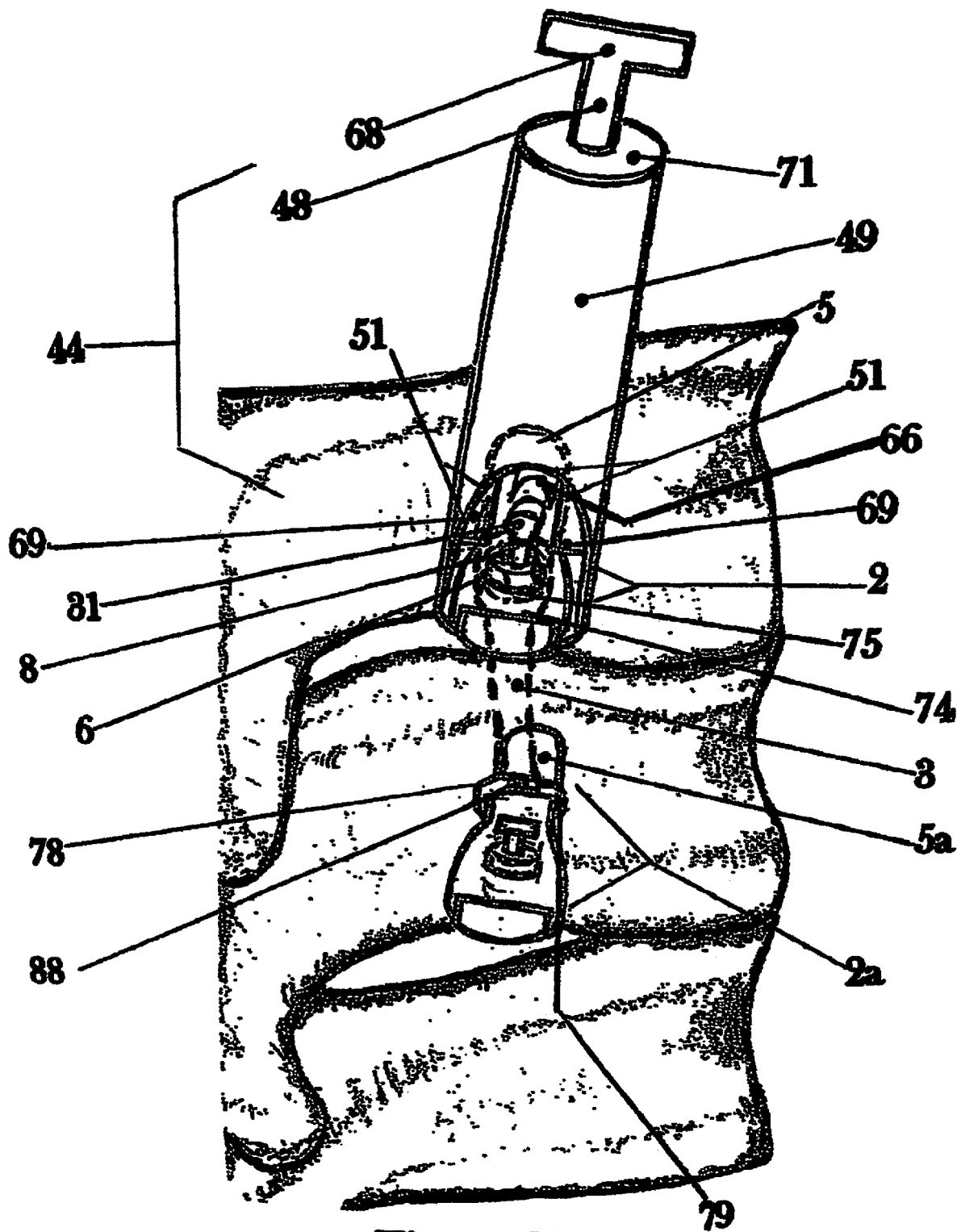

The next and final step necessary is to secure the connecting element 3 in position. This is illustrated in FIG. 22 B, which is an enlarged view of the CMIS 1 shown in FIG. 22 A; the enlargement permits a better illustration of the mechanism by which the leading end 74 of the connecting element 3 is captured and secured to the cranial anchor 2. In the preferred embodiment, the connecting element 3 is slidably coupled to the posterior jaw 5a of the caudal anchor 2a. This is accomplished, in the preferred embodiment, by providing a housing mechanism 78 which is a clamping mechanism actuated by the movable element 79 of this housing mechanism, which together form two clamping arms which are passed around the dorsal jaw 5a. Once the leading end 74 of the connecting element has been slid into the desired position, a securing screw 88 is tightened maintaining the position of the connecting element 3. The leading end 74 of the connecting element, which has been provided with an aperture 75 (shown in an outline of interrupted lines and solid circles) has been passed through the cutaway 51 of the implantation instrument 44, and is now positioned so that the aperture 75 can be disposed over the trailing end 8 of the securing screw 6 within the anchor. The inner cannula 49 within the instrument 44 can then be actuated by manually pushing its trailing end 71, which causes its bifurcated leading end 69 to push the leading end 74 anteriorly, disposing the aperture 75 over the horizontal bar 31 at the trailing end 8 of the screw 6; at that point, the trailing end 68 of the central trocar is actuated I manually rotated, causing the leading end 66 of the trocar 48 to engage the horizontal bar 31 which is consequently rotated until the bar locks the leading end 74 of the connecting element 3 into position. Please note that the connecting element 3 is shown as an interrupted line outline to elucidate other structures contributing to the locking mechanism of the cranial anchor.

Furthermore, the leading end of the dorsal jaw 5 of the cranial anchor is shown as a double interrupted line, distinguishing it from the other structures. Implantation is then considered complete. It should be appreciated that with modifications contingent upon the specific embodiments, the implantation technique described in this and the several previous drawings represents essentially the technique which would be utilized in all of the subsequent embodiments which have been disclosed and are illustrated in the drawings below.

Figure 23:
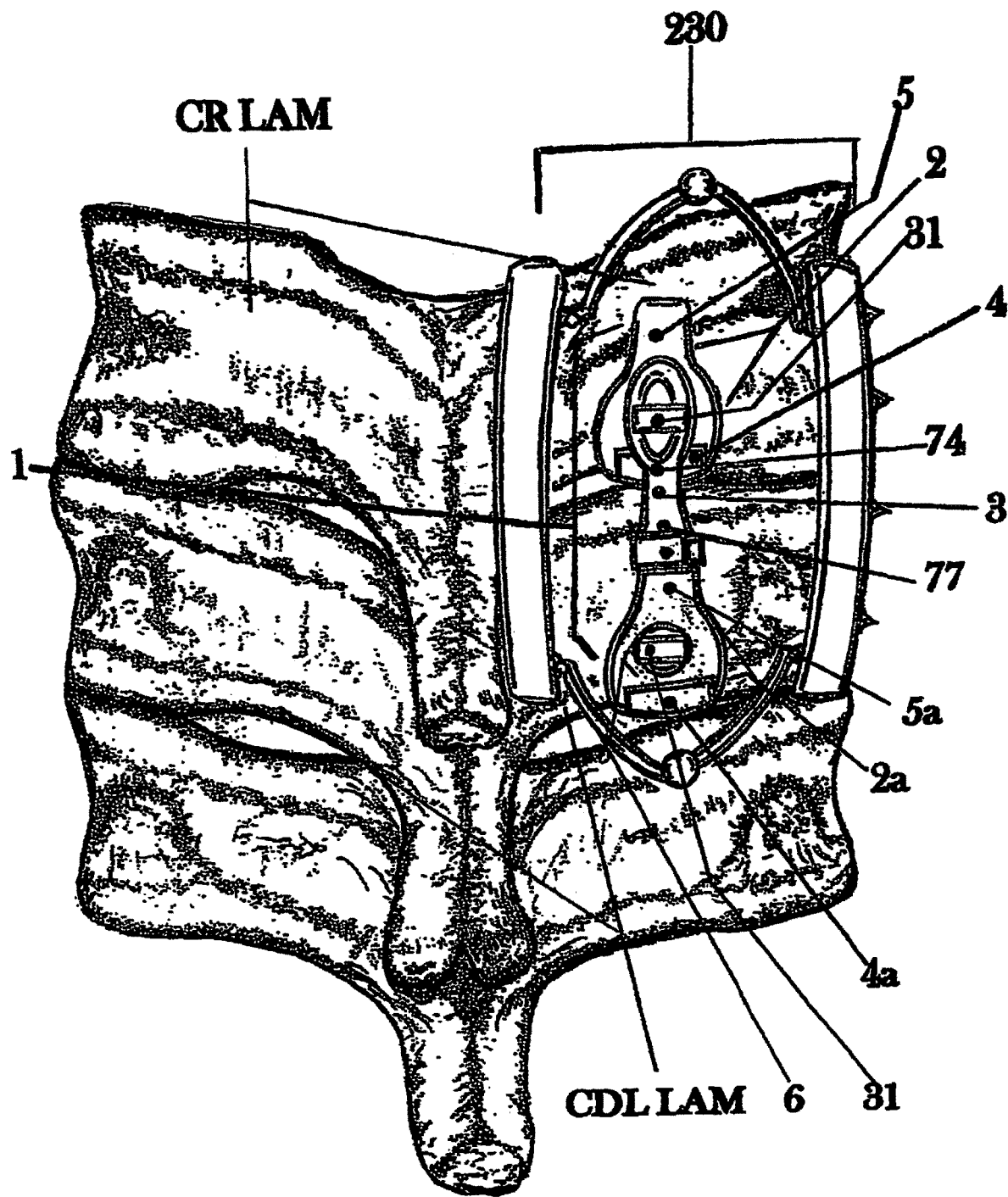
FIG. 23 is a posterior view showing the preferred embodiment of the CMIS linking two adjacent laminar anchors and stabilizing a target motion segment.

FIG. 23 is a posterior view showing the preferred embodiment of a right-sided CMIS 1 linking two adjacent laminar anchors and stabilizing a target motion segment. The patient is in the prone position. The retractor 230 illustrated in Paragraphs 142-149 maintains exposure, with the top of the page representing the top of the surgical field, and the patient's right side on the right side of the page. The dorsal jaw 5 of the cranial anchor 2 is at the top of the CMIS 1, with the cranial rim of the cranial lamina CR LAM seen above the superior edge of the jaw 5. In this preferred embodiment, the cranial anchor 2 does not require an associated connecting element. The horizontal bar 31 at the trailing end of the screw can be seen in a transverse position, with the edges of the bar capturing the leading end 74 of the connecting element 3, which extends caudally to couple with the caudal anchor 2a at the trailing end 77 of the connecting element 3. Again, the dorsal jaw 5a of that anchor 2a is seen, along with the horizontal bar 31 at the trailing end of the securing screw 6, which locked the anchor 2a to the caudal edge of the caudal lamina CDL LAM. The sublaminar jaws 4, 4a have been passed anterior to the respective laminae.

Figure 24:
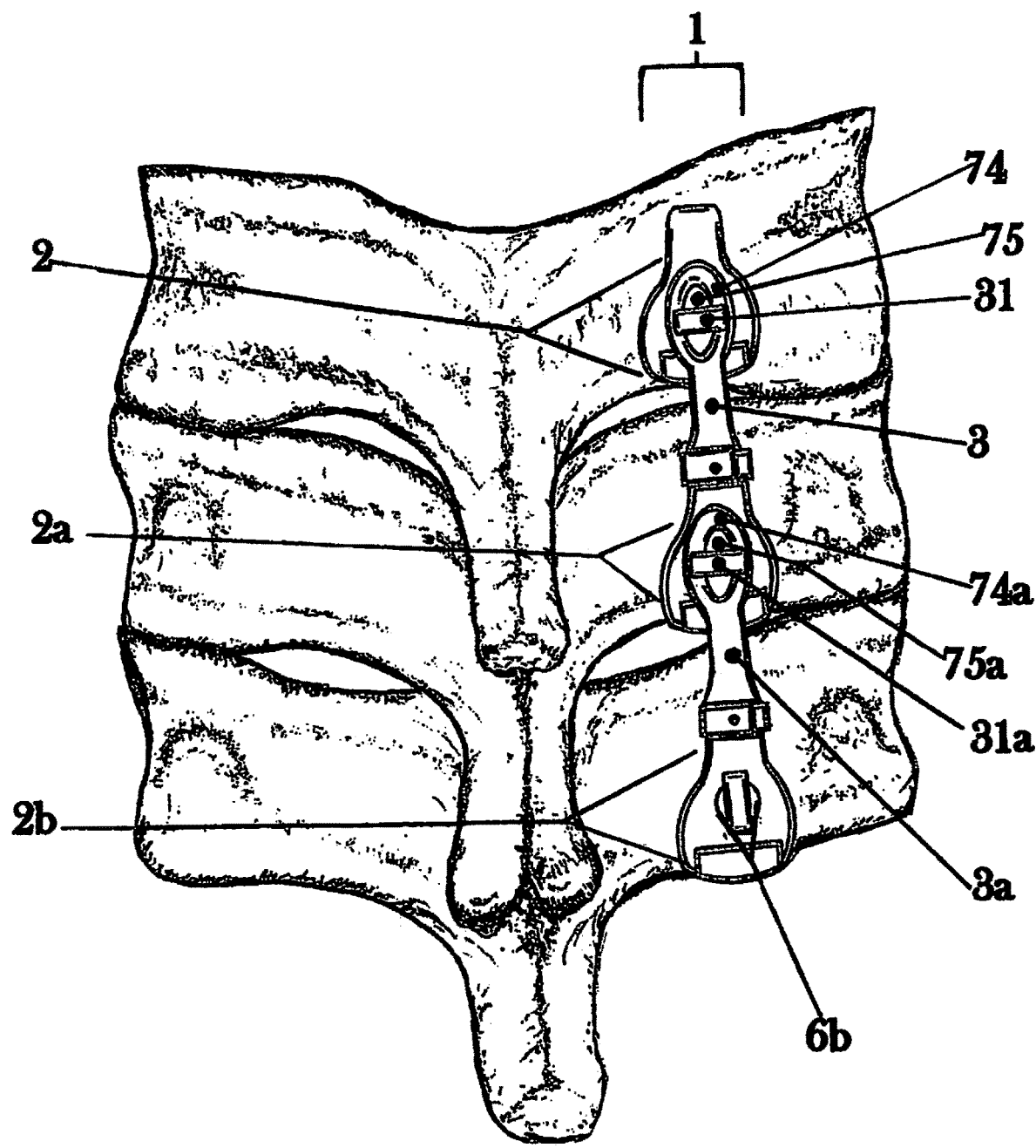
FIG. 24 reveals a two-level the construct spanning three vertebrae, shown in a posterior view.

A multilevel construct is also anticipated. FIG. 24 reveals another level laminar anchor 2b has been implanted onto the caudal vertebra of the original construct, shown again in a posterior view. The construct 1 is most easily extended by adding to the caudal end. When doing so, the connecting element 3a of the additional anchor 2b is coupled with the most caudal anchor 2a within the existing construct. Again it is noted that at each level, the aperture 75, 75a in the leading ends 74, 74a of the connecting elements 3, 3a are disposed over the horizontal bars 31, 31a at the trailing end of the securing screws at each level (6b is the only screw that can be seen in this projection); specifically, the configurations of the apertures 75, 75a are such that the horizontal bars 31, 31a can be disposed through the long axes of their apertures, but when the screws are rotated so that the horizontal bars 31, 31a are oriented orthogonal to the long axis of the apertures 75, 75a, the ends of the horizontal bars 31, 31a will overhang the sides of the leading ends 74, 74a of the connecting elements 3, 3a.

Figure 25:
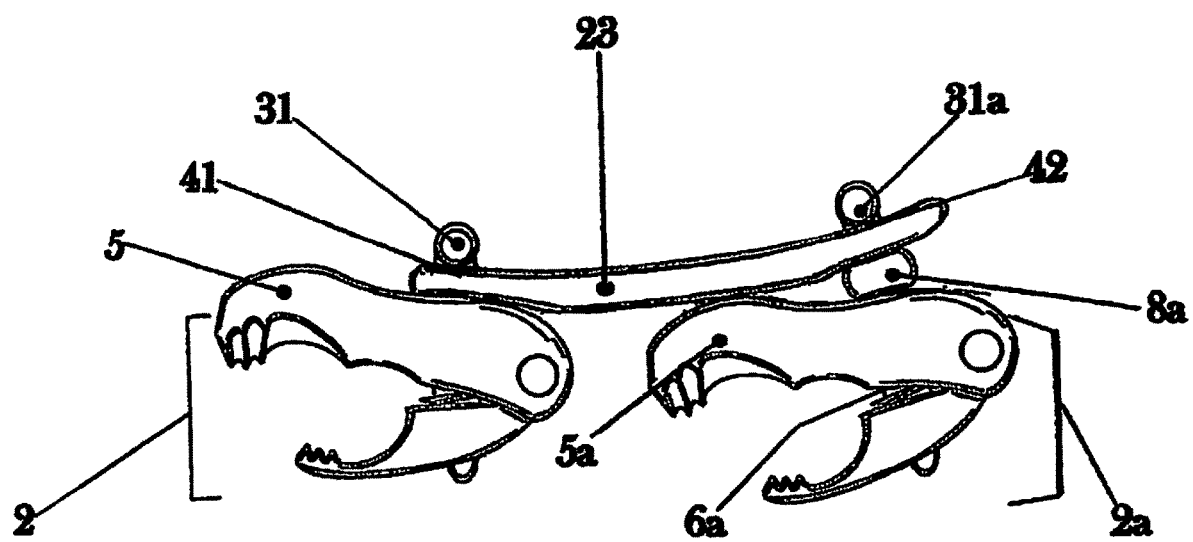
FIG. 25 shows an alternative embodiment of the connecting element that couples to each of the anchors, thus stabilizing the system.

FIG. 25 shows an alternative embodiment of the connecting element 23, specifically the trailing end thereof. It is recalled that in the preferred embodiment, this trailing end is a clamp-like configuration that couples with the dorsal jaw of the caudal anchor of a construct; the leading end of the preferred embodiment is a flattened segment with a central aperture. In this alternative embodiment, the connecting element 23 is provided with "mirror image," terminal segments 41, 42, each of which is configured to be flattened segments provided with apertures (not seen in this view), identical to the leading end in the preferred embodiment. Once the anchors 2, 2a are secured, the connecting element 23 is positioned so that the horizontal bars 31, 31a are disposed through the apertures and rotated, locking the construct against the dorsal jaws 5, 5a. When a lordotic curve is provided to the connecting element, such as in the image herein, the trailing end 5a of the seeming screw 6a may be modified as illustrated to accommodate the trailing end 42 of the element 23.

Figure 26:
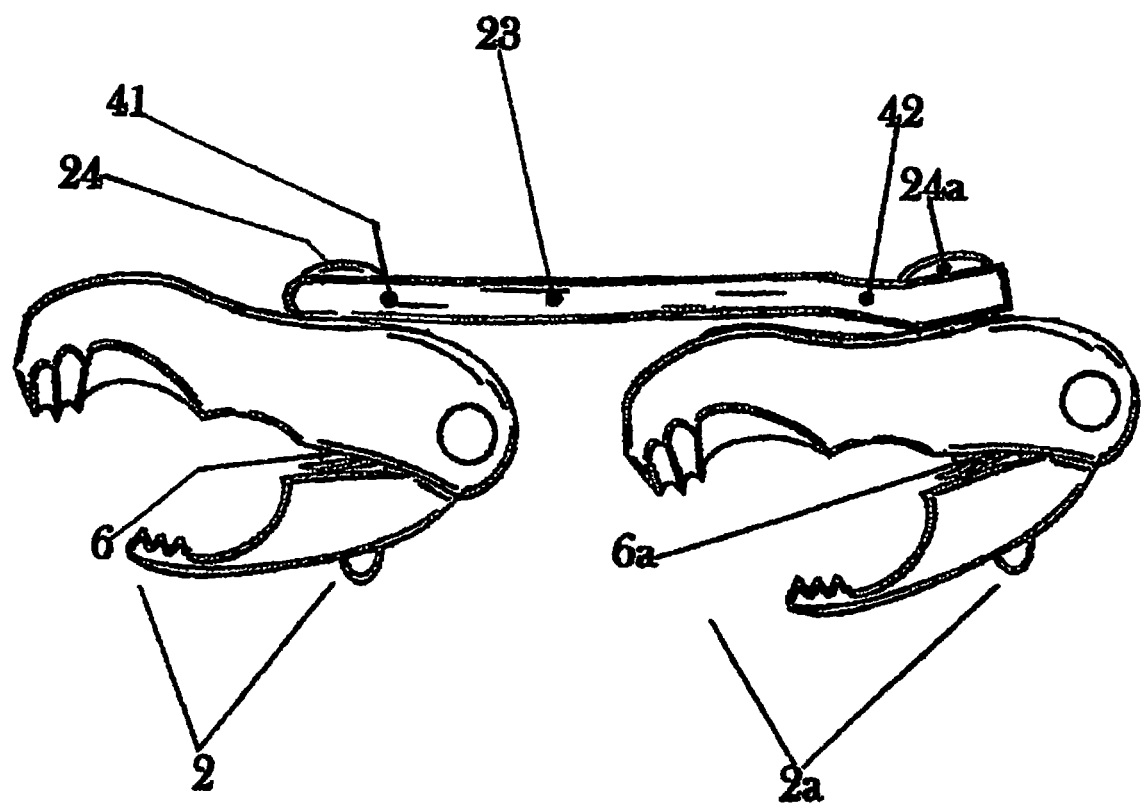
FIG. 26 is another alternative embodiment of the coupling of the connecting element to the laminar anchors.

The alternative connecting element 23 disclosed in FIG. 25 can be utilized with an alternative embodiment of the trailing ends of the securing screws 6, 6a, as demonstrated in a lateral view in FIG. 26. As such, these screws 6, 6a do not have the vertical extensions or horizontal bars seen in the preferred embodiment; rather, they terminate in a classical "screw head," embodiment 24. In this embodiment, the screws have been passed through both apertures in the terminal ends 41, 42 of the connecting element 23 prior to implantation—often referred to as "pre-loaded"—which mandates that the anchors 2, 2a must be implanted as a unit. Furthermore, it is readily apparent that those skilled in the art could anticipate another modification, in which the heads of the screws would be modified thus permitting the trailing ends of the connecting element to be disposed over the trailing ends of the screws, or other embodiments and relationships between the trailing ends of the screws and the connecting element. All such modifications can be anticipated herein, are in keeping with the Spirit and Scope of the Invention, and of course would be included within this application.

Figure 27:
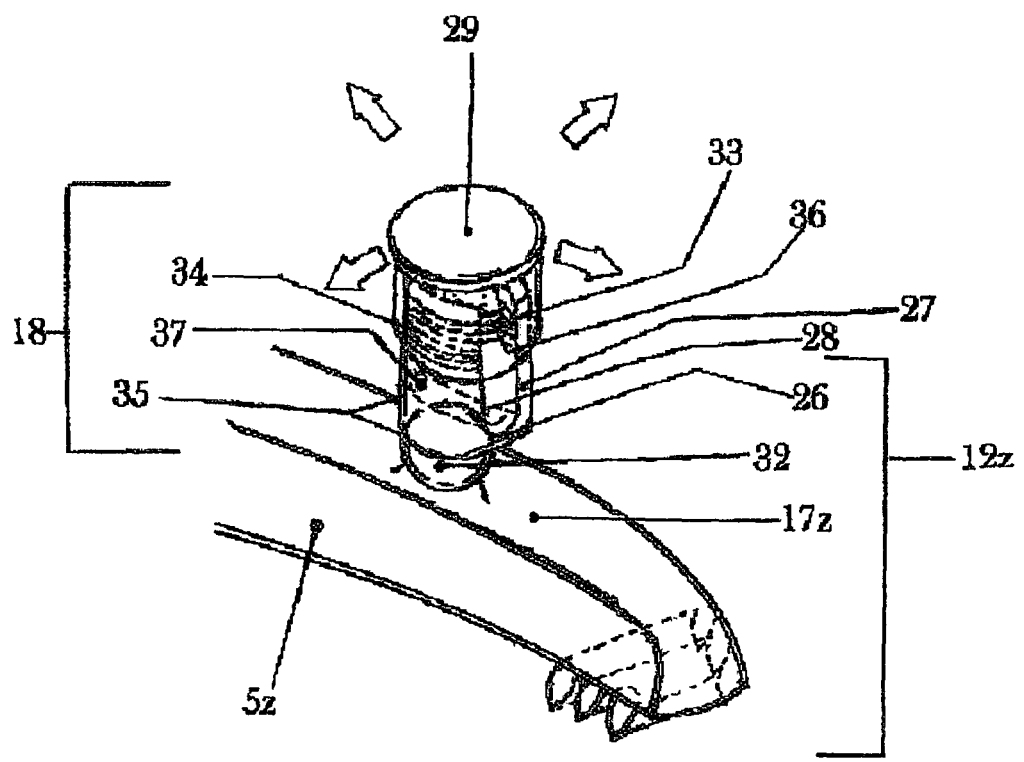
FIG. 27 illustrates an elevational perspective of an alternative embodiment of the laminar anchor which has been provided with a cradle which houses the connecting element that couples one laminar anchor to another.
Figure 28:
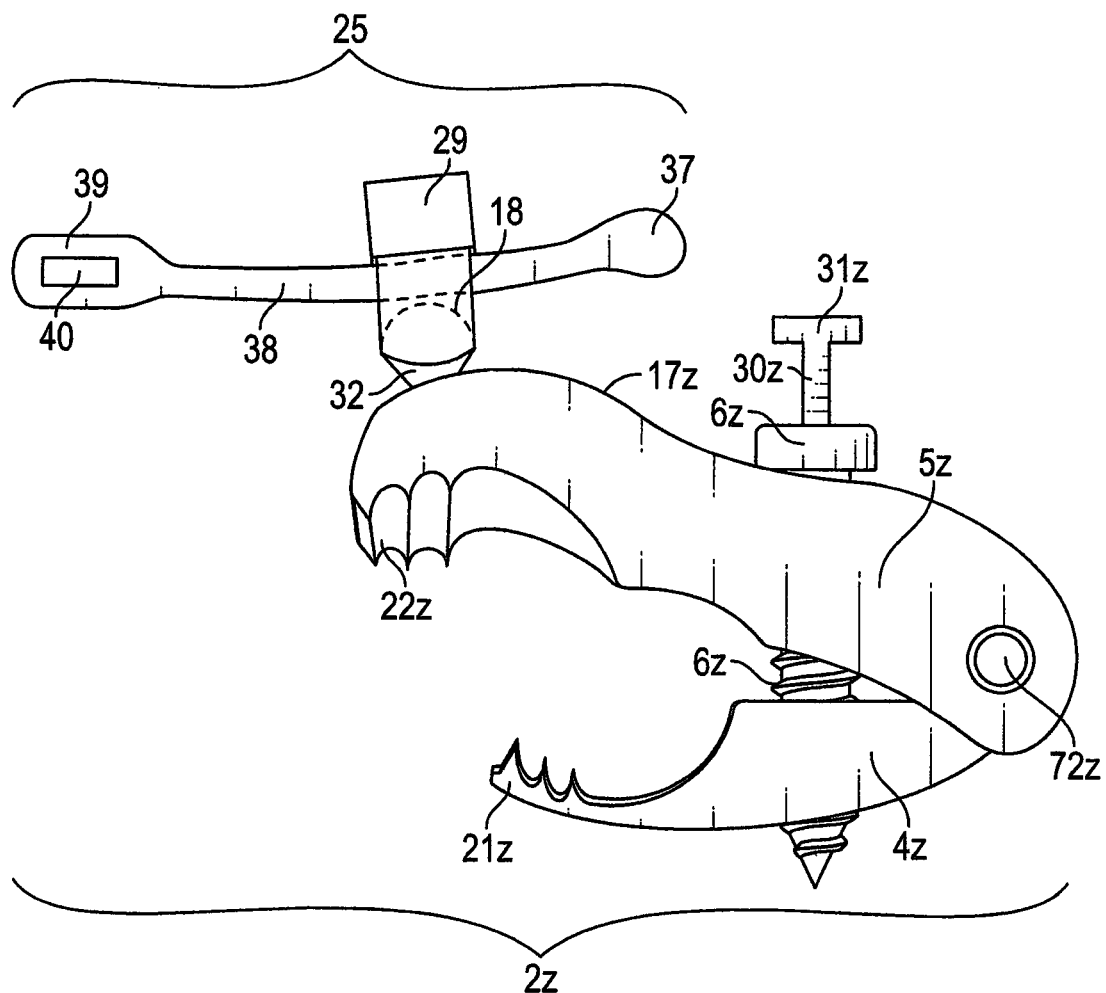
FIG. 28 demonstrates the connecting element of the laminar anchors which have been provided with the cradle embodiment.

FIG. 27 is an elevational view illustrating an alternative embodiment of the laminar anchor [2z in FIG. 28] in which a sphere 32 arises from the dorsal surface 17z of the cranial aspect 12z of the dorsal jaw 5z; this sphere 32 is irreversibly and rotatably coupled with a cradle 18, which in turn houses a connecting element (seen in FIG. 28) that couples this anchor 2z to the more cranial anchor. A hemisphere could also be anticipated in such an embodiment. This cradle 18 is a monolithic structure with a leading end 35 that encases the sphere 32, an articulation that confers upon the cradle 18 polyaxial movement, as indicated by the open arrows. Such movement permits reconciliation of slight changes in alignment of the anchors resulting from subtle anatomic variations after attachment to the adjacent laminae.

The cradle 18 is provided with a central channel 37 which has a base 26, a lateral wall 27 and a medial wall 28. This channel 37 houses an alternative embodiment of the connecting element 25, which is positioned for deployment within the cradle 18 at the time of implantation. One notes that the dorsalmost aspect of the cradle 18 is coupled with a screw-cap 29. The interior surfaces 33, 34 of the dorsalmost aspects of the channel 37 are provided with threading (partially shown in relief); the leading end 36 of the screw-cap 29 is also threaded, and with satisfactory positioning of the connecting element 25, the screw-cap 29 is deployed, securing the connecting element 25 in position.

It is again recognized that variations of these embodiments which maintain the spirit and scope of the invention can be envisioned. Such embodiments might include placing the threading disclosed above on the outside or exterior surfaces of the cradle rather than on the interior surfaces, which is then deployed by the use of a nut. In another embodiment, the walls of the cradle would be continuous with each other at the dorsalmost aspect of the cradle thus providing greater security to a central locking screw which would be disposed through this monolithic aspect of the cradle.

As viewed from the lateral perspective in FIG. 28, the connecting element 25 is contained within the cradle 18 at the time of the implantation. This element 25 may either be straight or [preferably] is provided with a slight lordotic curve, as demonstrated. Although this Figure demonstrates a lateral perspective, the connecting element 25 is rotated to demonstrate its unique configuration. One notes the components of the connecting element 25 including a leading end 39 which is substantially identical with that of the preferred embodiment disclosed in FIGS. 7, 8 above inasmuch that the current embodiment is also characterized by a flattened configuration which is ideally rectangular, but of course may be of any geometric configuration. This is, in turn, provided with a central aperture 40, which again is ideally a recapitulation of the same shape as the leading end 39 itself, but may be of any configuration. The aperture 40 is a critical component of the locking mechanism which secures the laminar anchors to each other, just as described in the preferred embodiment. In the ideal embodiment, the cross-section of the connecting element 25 is expected to be round so that it may easily disposed through the cradle 18, but any other geometric configuration is within the spirit and scope of the invention. Upon securing the caudal laminar anchor 2z to its target lamina, the connecting element 25 is advanced from its original position until its leading end 39 is secured to the anchor 2 at the superior level. The trailing end 37 of the connecting element 25 is slightly enlarged to serve as a stop on advancing the connecting element 25 inadvertently out of the cradle 18. Also seen in this image is the anterior jaw 4z, the coupling axle 72z, the securing screw 6z, and the teeth 21z, 22z of the anterior 4z and posterior 5z jaws, and the central portion 38 of the connecting element 25.

Figure 29:
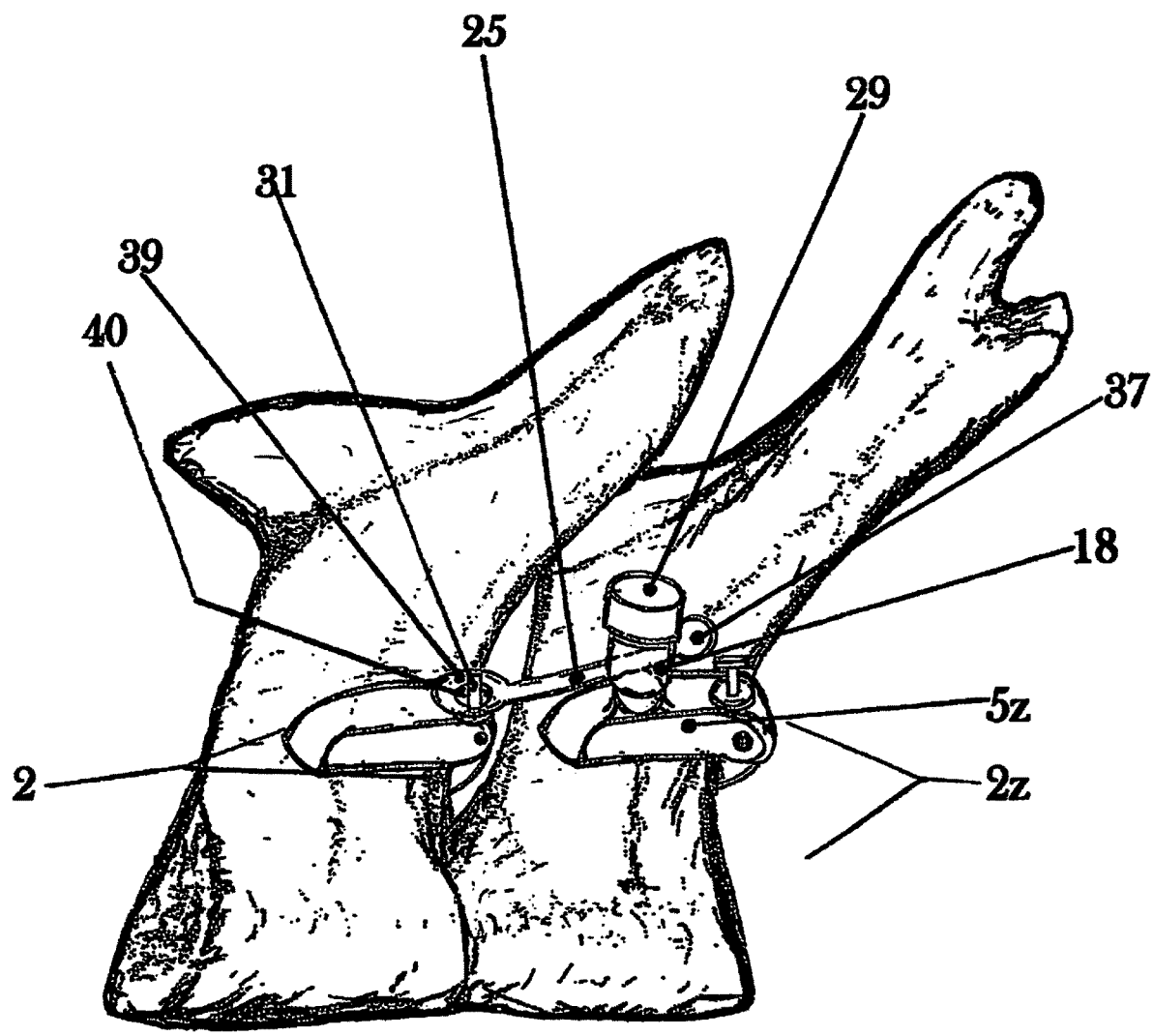
FIG. 29 studies a construct in which the laminar anchors are coupled to each other in the alternative embodiment in FIGS. 27-28.

FIG. 29 further illustrates the alternative embodiment disclosed in FIGS. 27-28. In this lateral elevational perspective, one notes the connecting element 25 has been advanced cranially until the leading end 39 is in a position such that its aperture 40 is disposed over the horizontal bar 31 of the trailing end of the securing screw; that horizontal bar 31 is then rotated 90°, locking the leading end 39 of the connecting element 25 against trailing end of the screw. The connecting element 25 is then secured caudally by tightening the securing cap 29 into the cradle 18, securing the trailing end 37 of the connecting element 25 in position. The cradle 18 can be seen as a component of the dorsal jaw 5z of the caudal anchor 2z, which has been secured against the caudal lamina. It can therefore be noted that the embodiment disclosed in FIGS. 27-29 would stabilizes a target motion segment in a unique, useful, novel and nonobvious fashion.

Figure 30A:
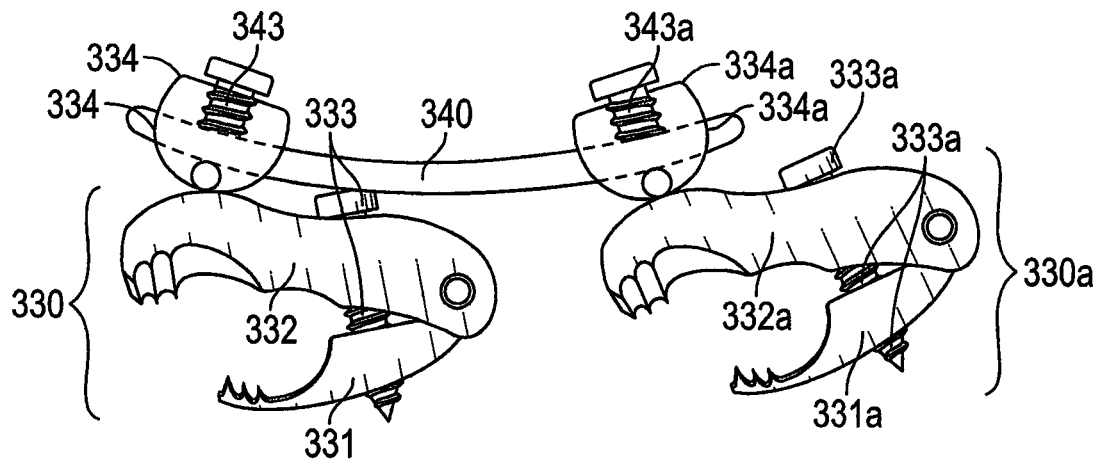
FIGS. 30 A/B/C are views showing embodiments in which cradles have been provided to the anchors, coupled by a rod.
Figure 30B:
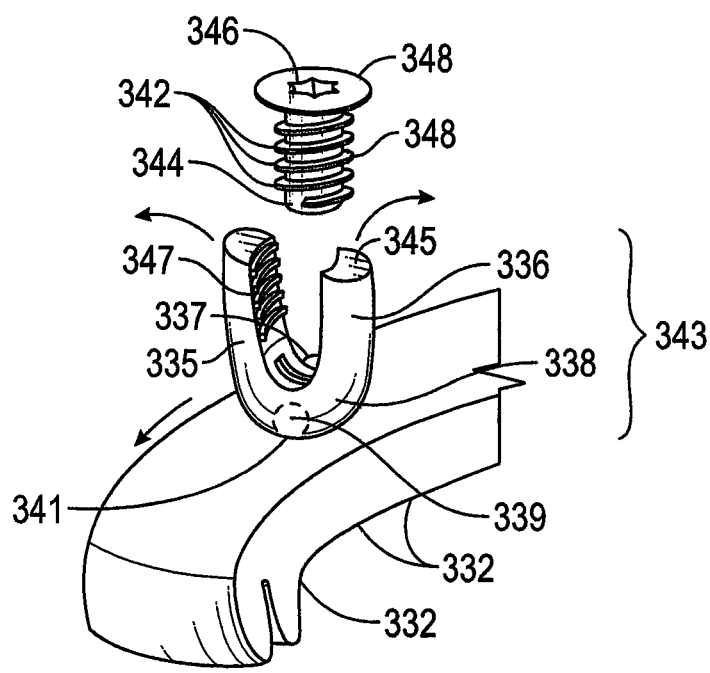

Another alternative embodiment is seen in FIGS. 30A, B; in FIG. 30A, one notes a lateral view showing anchors 330, 330a similar to those disclosed in the preferred embodiment inasmuch that they each are provided with a sublaminar jaw 331, 331a and a dorsal jaw 332, 332a which are secured against the laminae by actuating securing screws 333, 333a. Differentiating these anchors, however, are the tulips 334, 334a arising from the dorsal jaws 332, 332a and designed to accommodate a connecting rod 340 which stabilizes the construct. In FIG. 30A, one sees, in relief, images of the connecting rod 340 locked within the tulips 334, 334a by the locking screws 343, 343a. Certain aspects of the tulip 334 are more clearly demonstrated in FIG. 30B, which shows the dorsal jaw 332 giving rise to a pedestal 341 I sphere 339 complex. The leading end 338 of the tulip 334 is irreversibly coupled to the sphere 339, conferring polyaxial movement upon the tulip 334—as demonstrated by the curved arrows. This allows the embodiment to accommodate the varying geometry of the cervical spine FIG. 30B also demonstrates that the medial 335 [335a] and lateral 336 [336a] walls in turn create a channel 337 [337a] designed to accommodate the connecting rod 340. After securing the anchors 330, 330a to the laminae, the rod 340 is inserted into the channels 337 [337a]. The interiors of these channels 337 [337a] are provided with threading 347 [347a] which is configured to be complementary to the threading on the leading ends 344 [344a] of the locking screws 343 [343a]; these leading ends 344 [344a] are disposed through the trailing ends 345 [345a] of the tulips 334 [334a], and secured into position by a screwdriver securing the rod in place, thus stabilizing the construct. This stabilizes a target motion segment in a unique, useful, novel and nonobvious manner.

Figure 30C:
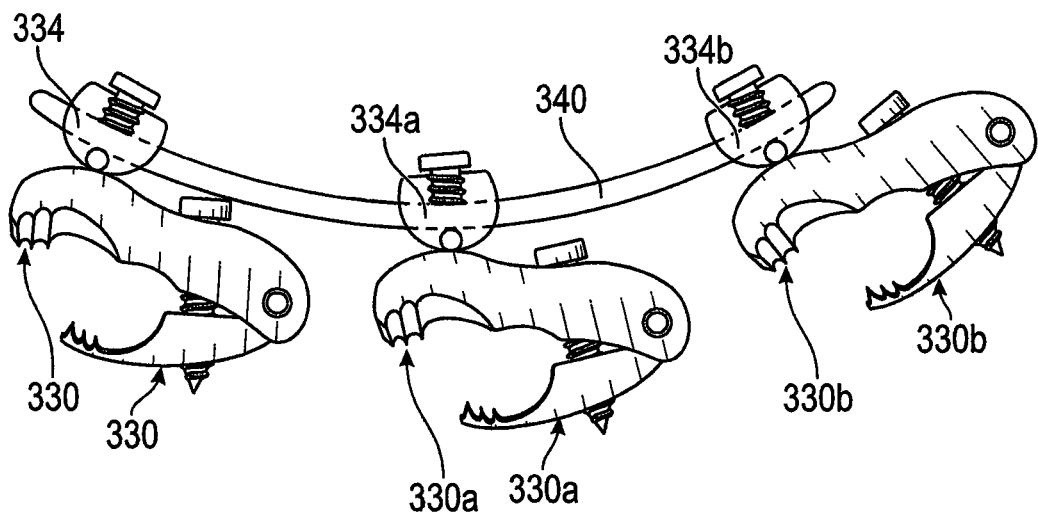

A multilevel iteration of this embodiment is certainly anticipated and achieved with the use of an additional anchor 330b, and is illustrated in FIG. 30 C. A longer rod 340, of course, would be utilized and passed into the channel 337b of the tulip 334b associated with the additional anchor 330b and secured in place, stabilizing the construct. Although a two-level construct is shown herein, using the same principles and iterations, a construct of any number of levels between C2 and the thoracic spine can be conceived. Variations of these embodiments can, of course, be envisioned and anticipated by those familiar with the art; all such variations are, of course, within the spirit and scope of the invention.

Figure 31:
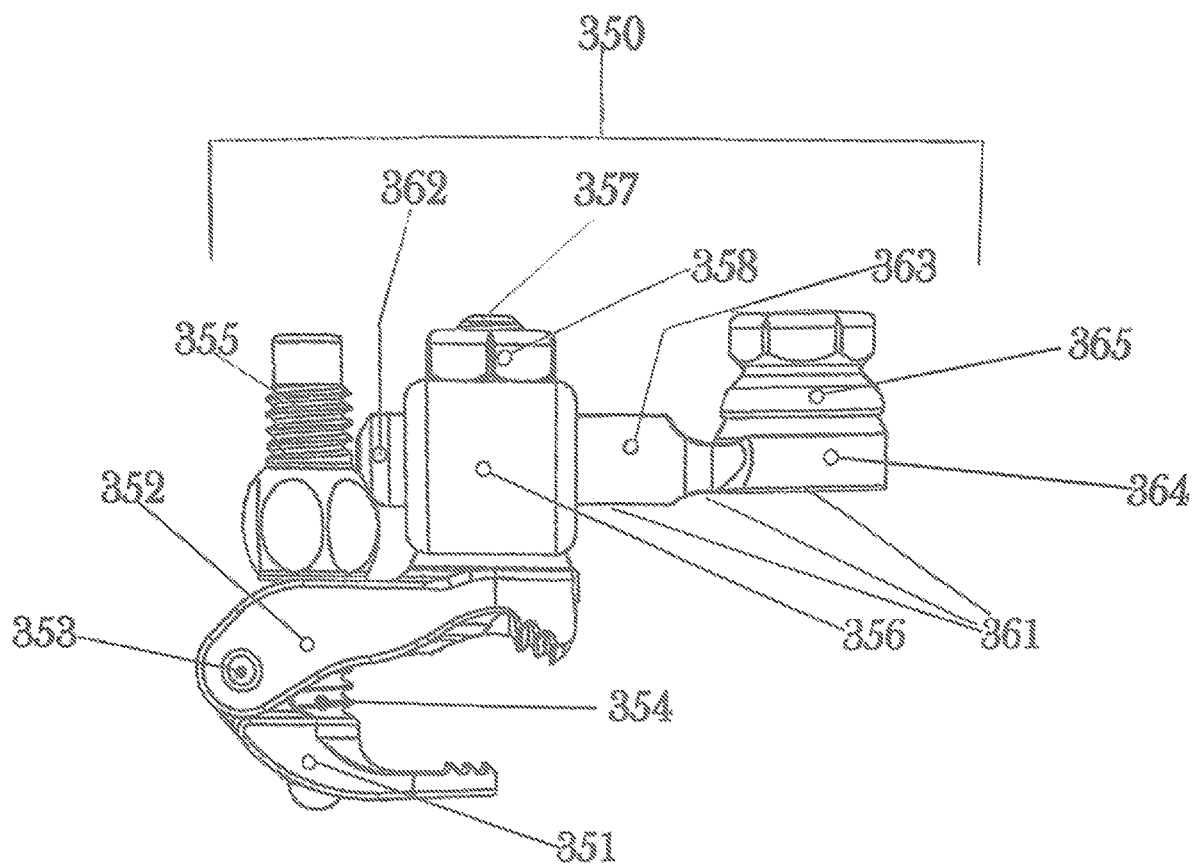
FIG. 31 is an alternative embodiment of the connecting element and how it is coupled to the anchor.

Another alternative embodiment of the CMIS which stabilizes a target motion segment in a unique, useful, novel and nonobvious manner is portrayed in a lateral view in FIG. 31. In this variation, an anchor 350 is again provided with a sublaminar jaw 351, as well as a dorsal jaw 352, which are irreversibly coupled by a pivoting axle 353, and compelled towards each other by a securing screw 354 capturing the lamina Additionally, it is noted that the trailing end 355 of the securing screw 354 is threaded, which allows it to accept a coupling with the anchor secured to the more caudal level. In addition, a housing mechanism 356 can be seen secured to the dorsal jaw 352 by means of a locking screw 357, which together with a locking nut 358 controls a coupling apparatus (not seen in this view) component of the housing mechanism 356. This apparatus slidably couples with the trailing end 362 of a connecting element 361, rendering this element positionable in multiple planes, which again accommodates the CMIS to anatomic variations.

Figure 32A:
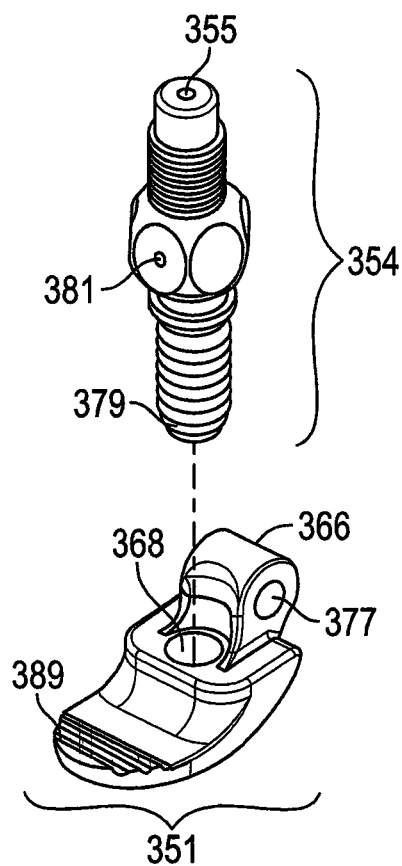
FIGS. 32 A-D depict various elevated, exploded views of the alternative system seen in FIG. 31.
Figure 32B:
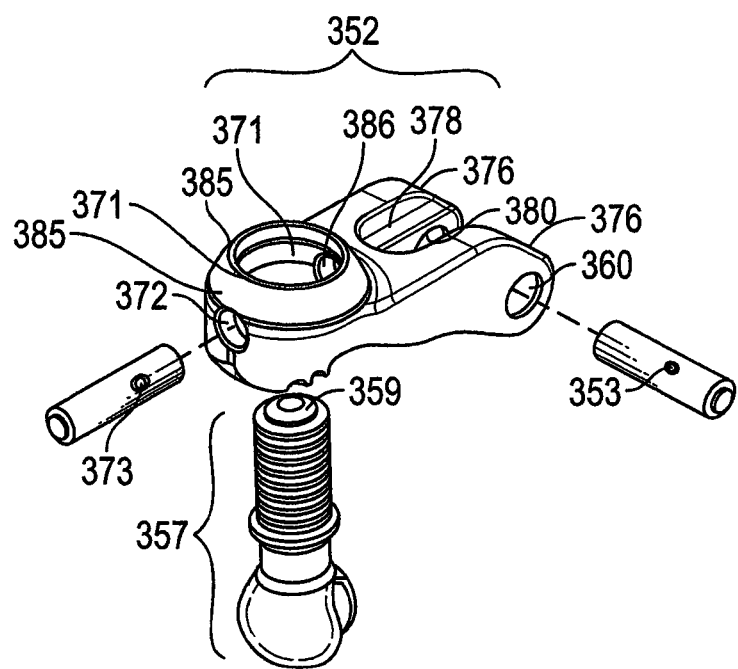
Figure 32:
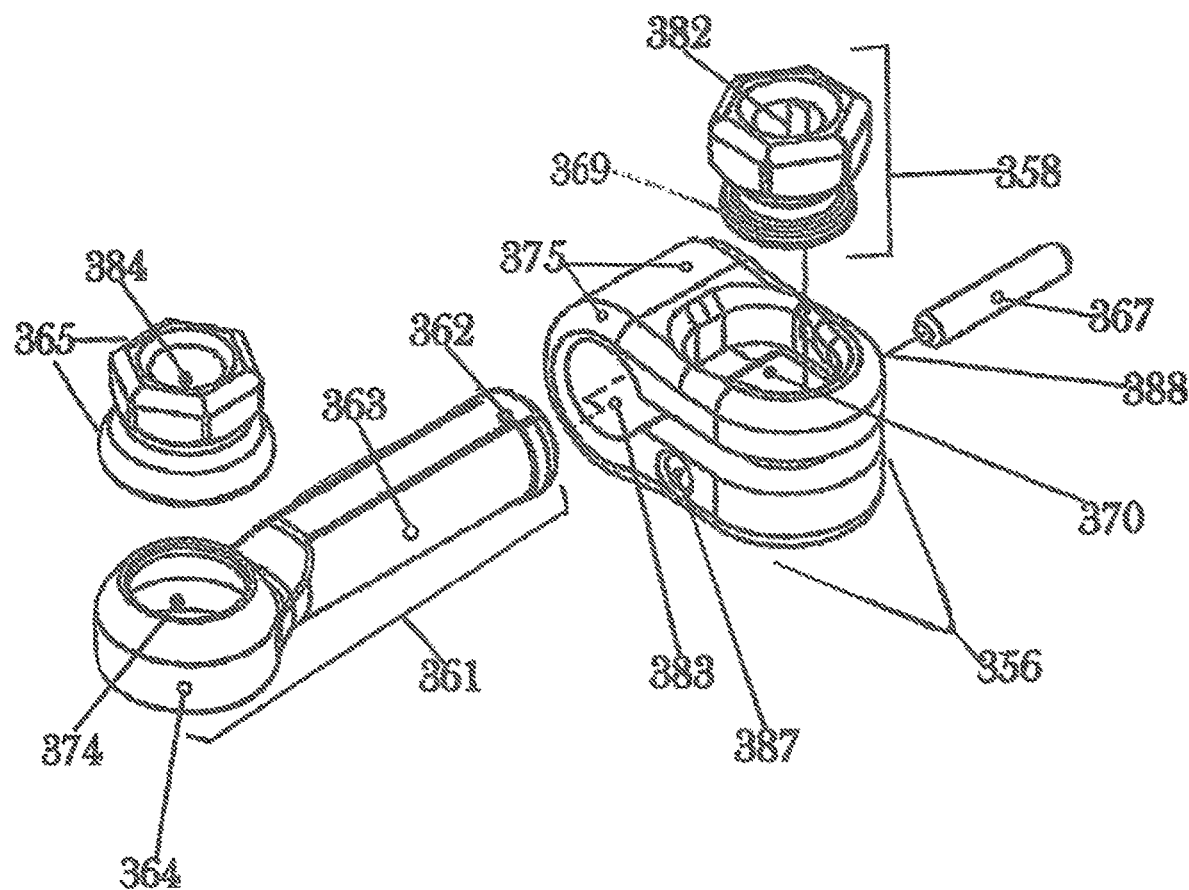
Figure 32:
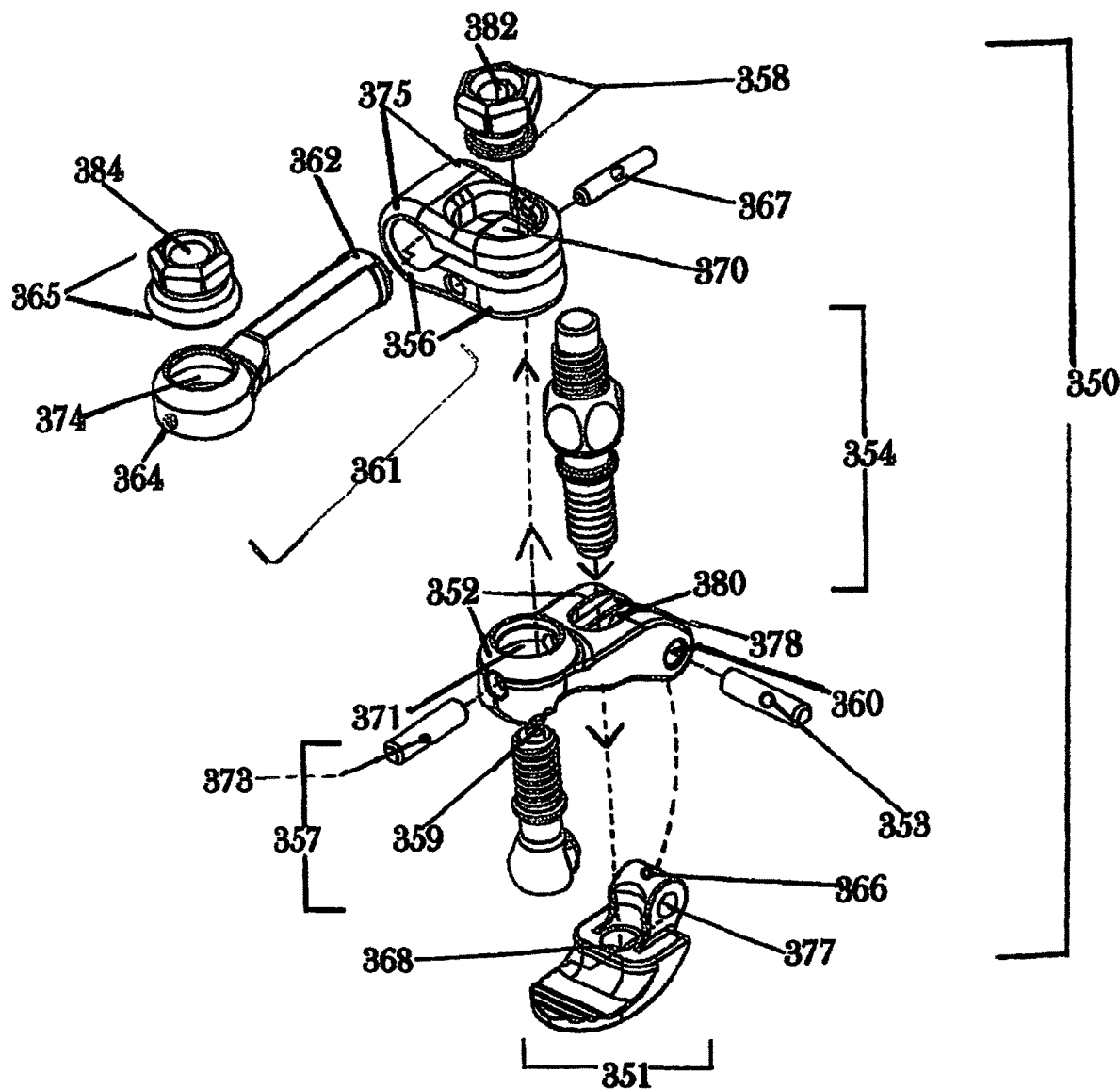

The complexity of the embodiment disclosed in FIG. 31 is appreciated in FIGS. 32 A-D, which depict elevational, exploded views of the components of the anchor 350 (32 A I B I C) as well entire embodiment. In FIG. 32 A, the sublaminar jaw 351 and securing screw 354 are portrayed, with the sublaminar jaw 351 provided with a dorsal extension 366 which is configured to articulate with the dorsal jaw, as illustrated in FIGS. 32 B and D. An aperture 377 in the dorsal extension 366 receives an articulating axle to couple with the dorsal jaw 352, again seen in FIGS. 32 B and D. This coupling confers the anteroposterior axis of movement upon the jaws 351, 352, which is actuated by the securing screw 354, the leading end 379 of which is disposed initially through the dorsal jaw, and then through the aperture 368 in the sublaminar jaw 351. Other features of the screw 354 include the trailing end 355 and a hexagonal portion 381 of the shaft which is configured to couple with the leading end of the connecting element arising from the anchor caudal to the subject illustrated herein. Also seen in this image are the small teeth 389 on the sublaminar jaw 351.

FIG. 32 B illustrates the dorsal jaw 352 coupling with the locking screw 357 which then couples the dorsal jaw 352 to the housing mechanism (FIG. 32 C). The leading end 385 of the dorsal jaw 352 is provided with a channel 371 through which a locking screw 357 is disposed; a retention pin 373 is passed through an aperture 372 at leading end 385, passing across the channel 371, as well as aperture 386 at the caudal aspect, this pin 373 maintains the locking screw 357 in position. The caudal end 376 of the dorsal jaw 352 is provided with a notch 378, through which the securing screw is positioned, as seen in 32 D. The axle 353 which couples the sublaminar jaw 351 with the dorsal jaw 352 is disposed through aperture 360 in the caudal end 376 of the dorsal jaw 352, and after passing through the dorsal extension of the sublaminar jaw (FIG. 32 D), this axle 353 is then secured into an aperture 380, which maintains the coupling of the jaws 351, 352.

The housing mechanism 356 and the connecting element 361 are portrayed in FIG. 32 C. Features of the housing mechanism 356 include a central channel 370 through which the lacking screw is disposed (see FIG. 32 D), with a threaded leading end 369 of a locking nut 358 securing the nut 358 to the dorsal aspect of the channel 370, with a channel 382 within the nut 358 that will receive the locking screw. A retention pin 367 will be passed through caudal and cranial apertures 387, 388 in the housing mechanism 356, to secure the locking screw during assembly. The connecting element 361 is coupled to the housing mechanism 356 which is provided with a coupling apparatus 375 that is actuated to optimally positions the element 361. This is achieved by tightening the securing nut 358 against the leading end of the locking screw, which causes the coupling apparatus 375 to narrow channel 383 into which the trailing end 362 and at least part of the shaft 363 of the connecting element 361 have been disposed, and are repositionable prior to narrowing the channel 383. Once narrowed, the connecting element 361 is locked into position, with the leading end 364 of the element 361 coupling to the more cranial anchor of the construct, with the trailing end of the screw of the cranial anchor disposed through and interfacing with internal threading within channel 384 of the securing nut 365. Upon successful positioning, the securing nut 365 is tightened, thus stabilizing the target motion segment.

The assembly of the components illustrated in FIGS. 32 A-C into the completed embodiment of anchor 350 is demonstrated in FIG. 32 D. The coupling of the jaws 351, 352 is accomplished by inserting the dorsal extension 366 of the sublaminar jaw 351 into the notch 378 of the dorsal jaw 352, as indicated by the arched interrupted line. Also indicated is the axle 353 passing through the aperture 360 in the dorsal jaw 352, and [presumably] passing through the channel 377 in the dorsal extension 366 once this is in position, and finally the leading end of the axle 353 is secured into aperture 380 again in the dorsal jaw, thus completing the coupling. In at least one embodiment, the axle 353 secures into aperture 380 with a "pressure fit." The securing screw 354 is disposed through the notch 378 in the dorsal jaw 352 and ultimately into the aperture 368 in the sublaminar jaw 351, as indicated by the interrupted line highlighted by the downward directed arrows. This arrangement positions the screw 354 such that upon actuating the screw 354, the jaws 351, 352 are compelled towards each other, which, as previously disclosed, secures the anchor to the lamina. The locking screw 357 passes through the channel 371 of the dorsal jaw 352 and into the channel 370 of the housing mechanism 356, as indicated by the interrupted line highlighted with the upward directed arrows. A retention pin 373 passed through aperture 372 in the dorsal jaw 352 maintains the screw 357 in position. The leading end 359 of this screw 357 is disposed through the channel 370 of the housing mechanism 375, and into the channel 382 of the locking nut 358, locking the dorsal jaw 352 to the housing mechanism 375. A retention pin 367 is used to maintain the screw 357 under tension. As previously disclosed, with tightening nut 358, the connecting element 361 is secured. Prior to securing this in place, the craniocaudal dimension may be adjusted by compression or distraction of the construct, and once this is accomplished and in satisfactory position, the locking nut 358 of the housing mechanism 356 is secured thus capturing the connecting element in the desired position.

A complete construct of the embodiment disclosed in FIGS. 31, 32 A-D is portrayed secured to the cervical spine in FIG. 33, a right-sided posterior oblique view of the C3 through C7 spinal segment. This demonstrates a construct 390 with right-sided anchors 350, 350a secured to the C5 and C6 laminae, with a connecting element 361a stabilizing that motion segment. When reduced to practice, the connecting element 361 associated with the more cranial anchor 350 would not be incorporated into the final construct, as it could interfere with the movements of the lamina above the construct—in this example, the C4 right sided lamina. Also, the final iteration would configure the caudal anchor 350a so that it would not have a caudal overhang that interferes with the lamina caudal to the construct. This image is illustrative only, and it would be anticipated that in clinical practice, constructs would likely be implanted bilaterally.

Figure 34:
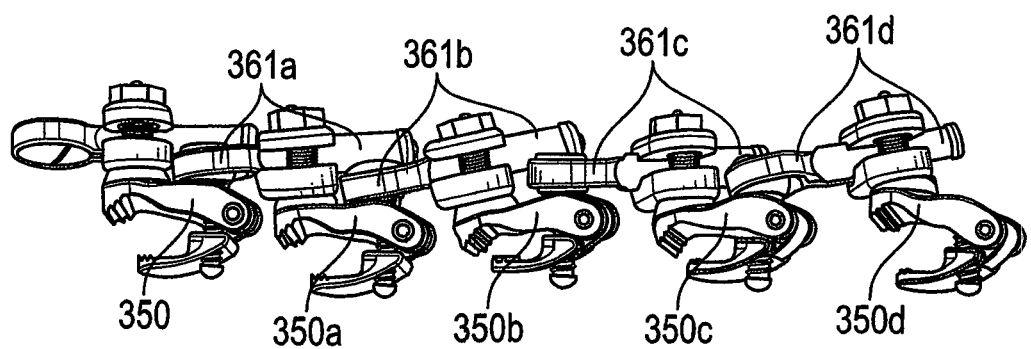
FIG. 34 shows a multilevel construct of the alternative embodiment in FIG. 31.

A multilevel construct of the alternative embodiment in FIG. 31 can be anticipated, and a lateral view of such a construct in the isolated state is shown in FIG. 34. Each successive anchor 350, 350a, 350b, 350c, 350d are coupled to the more cranial anchor by the connecting elements 361, a-d in the same manner as seen in the single-segment embodiment.

Figure 35:
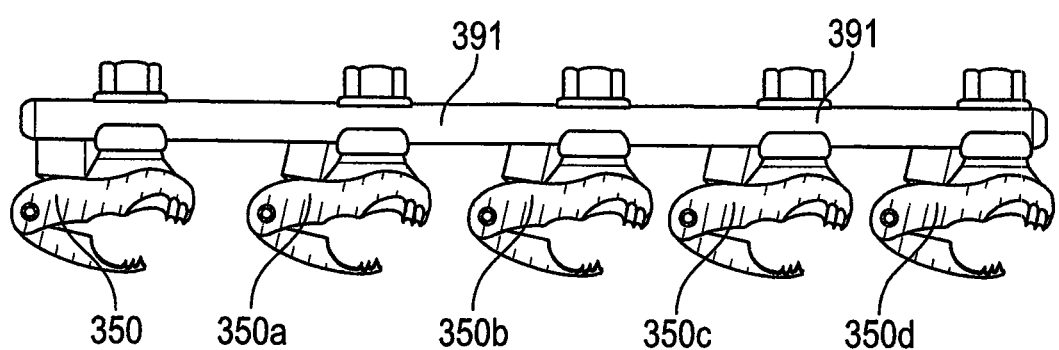
FIG. 35 depicts a multilevel construct of the alternative embodiment in FIG. 31 utilizing a rod connecting element.

FIG. 35 depicts a lateral view of an isolated, multilevel construct of the alternative embodiment of the anchor 350 presented in FIG. 31; however, this configuration utilizes a single rod connecting element 391 connected to the anchors 350, 350a-d and hence stabilize the construct. Variations of these embodiments can, of course, be envisioned and anticipated by those familiar with the art; all such variations are, of course, within the spirit and scope of the invention.

Figure 36A:
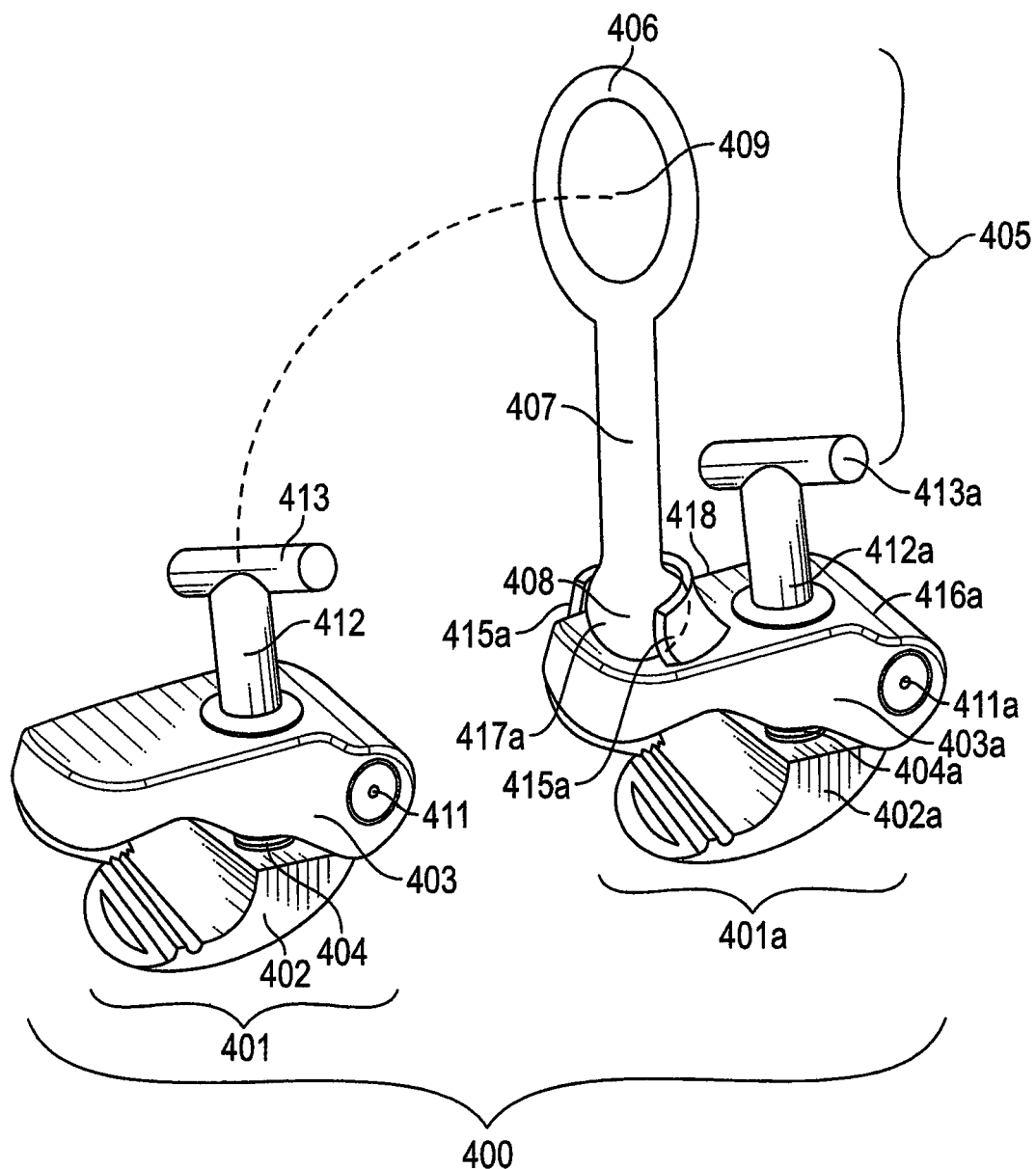
FIG. 36 A illustrates an elevational view of an embodiment in which the base of the connecting element is secured within a cup and is then rotated into position to couple with an adjacent anchor.
Figure 36B:
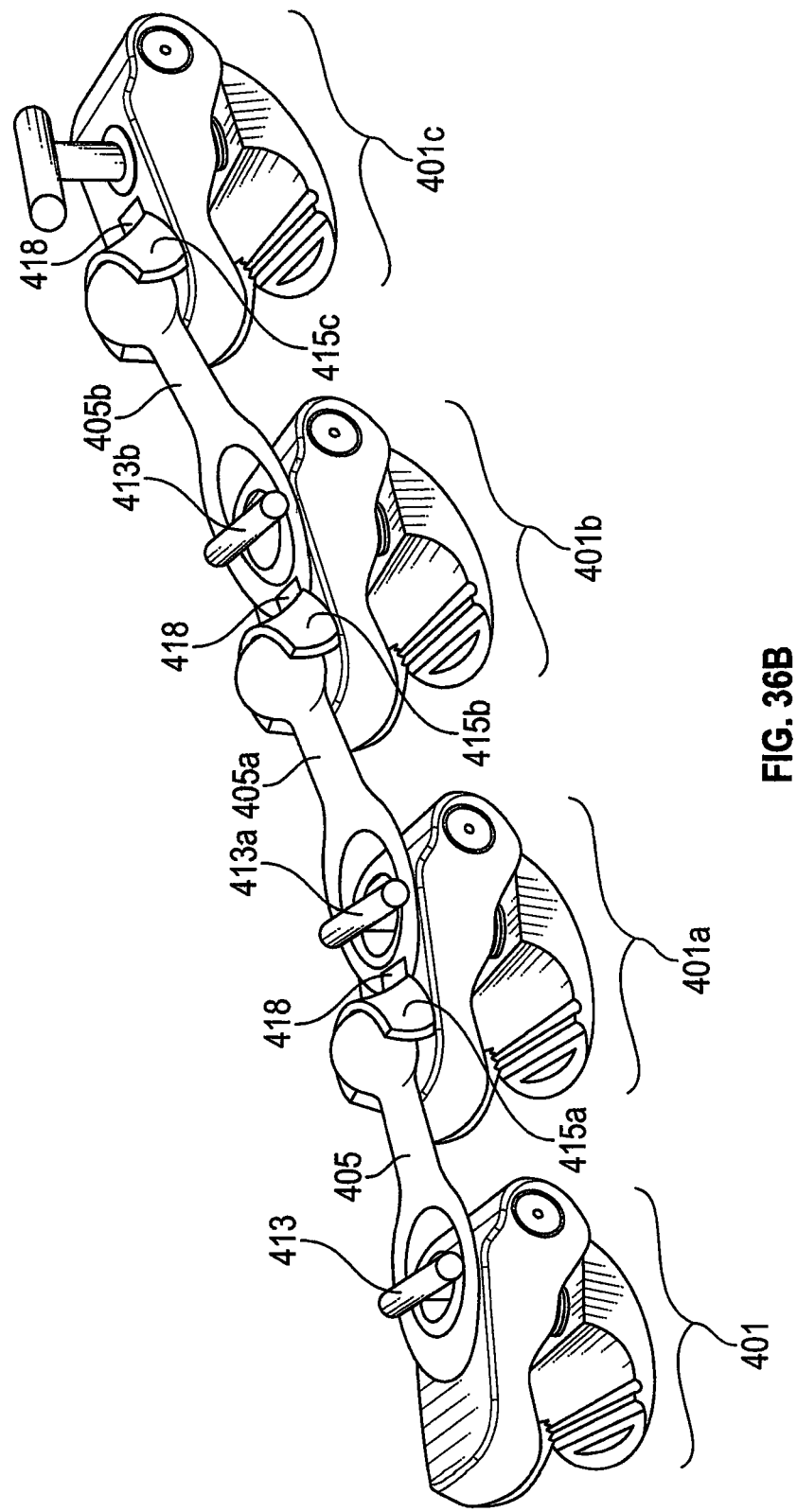

In another embodiment 400, anchors 401, 401a are again comprised of sublaminar jaws 402, 402a, dorsal jaws 403, 403a these pairs of anchors coupled by axles 411, 411a and actuated by securing screws 404, 404a disposed through the caudal aspects of the pairs of jaws 402, 403 and 402a, 403a and compelling the the jaws towards each other hence securing the anchors 401, 401a to the laminae in a manner substantially equivalent to the previous embodiments herein disclosed. Also, as in some previous embodiments, the relationships of the screws 404, 404a within the anchors are such that a series of audible clicks are appreciated as the screws 404, 404a are brought into various positions. As illustrated in FIG. 36 A, an elevational view of this embodiment, the distinguishing feature of this embodiment is the connecting element 405, which in this alternative embodiment is comprised of a leading end, 406, a central portion 407, and a trailing end 408; the deployment of this connecting element 405 provides a device 400 which stabilizes a target motion segment in a unique, useful, novel and non-obvious fashion. The leading end 406 of the connecting element 405 is substantially flattened and expanded, and elliptical or rectangular in configuration. It is provided with a central aperture 409, and is substantially similar in configuration to the preferred embodiment of the connecting elements disclosed in FIGS. 7, 8, 22A, 22B, 23, as well as those seen in the alternative embodiments disclosed in FIGS. 25 . . . 29. In this embodiment, after securing the cranial anchor 401 to the target lamina by actuating the securing screw 404, the first audible click indicates that the anchor is nearly completely secured, with the horizontal bar 413 provided to the trailing end 412 of the screw 404 is in ideal position (oriented along the craniocaudal axis) to accept the aperture 409 on the leading end 406 of the connecting element 405, which would be anticipated to be associated with the more caudal anchor 401a. A central feature of this embodiment is the trailing end 408 of the connecting element 405, which is a spherical configuration that is irreversibly anchored within a cupped socket 415a which arises from the muscular surface 416a of the dorsal jaw 403a. This configuration confers polyaxial movement upon the connecting element 405. A defect 417a in perimeter of the cupped socket 415 supports this coupling over a range of angles, accommodating slight variations in anatomy and placement. The connecting element is then deployed by pursuing the course demarcated by the arching, interrupted line, passing the aperture 409 over the horizontal bar 413 of the securing screw 404. The final craniocaudal dimension can be achieved as a function of the configuration of the aperture 409, which is greater in that dimension. This permits the surgeon to apply compression/distraction achieving the optimal craniocaudal position, at which point the horizontal bar 413 is then rotated into final position. At that point, one or more seeming screws 418 within the perimeter of the socket 415 are actuated to prevent rotation, achieving final locking and stabilization of the construct. It is also noted that the dorsal jaw 403 of the cranial anchor 401 is modified such that it is not provided with a socket as there is (obviously) no need for a [more] cranial connecting element. In a variant of this embodiment not illustrated herein, a socket is provided without a connecting element. Furthermore, these cupped sockets are designed such that the leading ends of the connecting elements can be inserted into the cups, having been provided with a configuration that permits the leading ends to be "snapped into" position if a cranialward extension is required in the future.

An isolated multilevel embodiment in which the connecting elements are rotated into position in this fashion is portrayed in FIG. 36 B. Again, the cranialmost anchor 401 is not provided with a connecting element mechanism. Otherwise, in the successive caudal direction, anchors 401a, 401b, and 401c are coupled to the more cranial anchors as the result of the deployment of connecting elements 405, 405a and 405b being locked by the horizontal bars 413, 413a and 413b. Again, within the perimeters of each of the sockets 415a, 415b, 415c are one or more screws 418 that upon actuation prevent spherical rotation. Variations of these embodiments can, of course, be envisioned and anticipated by those familiar with the art; all such variations are, of course, within the spirit and scope of the invention.

Figure 37:
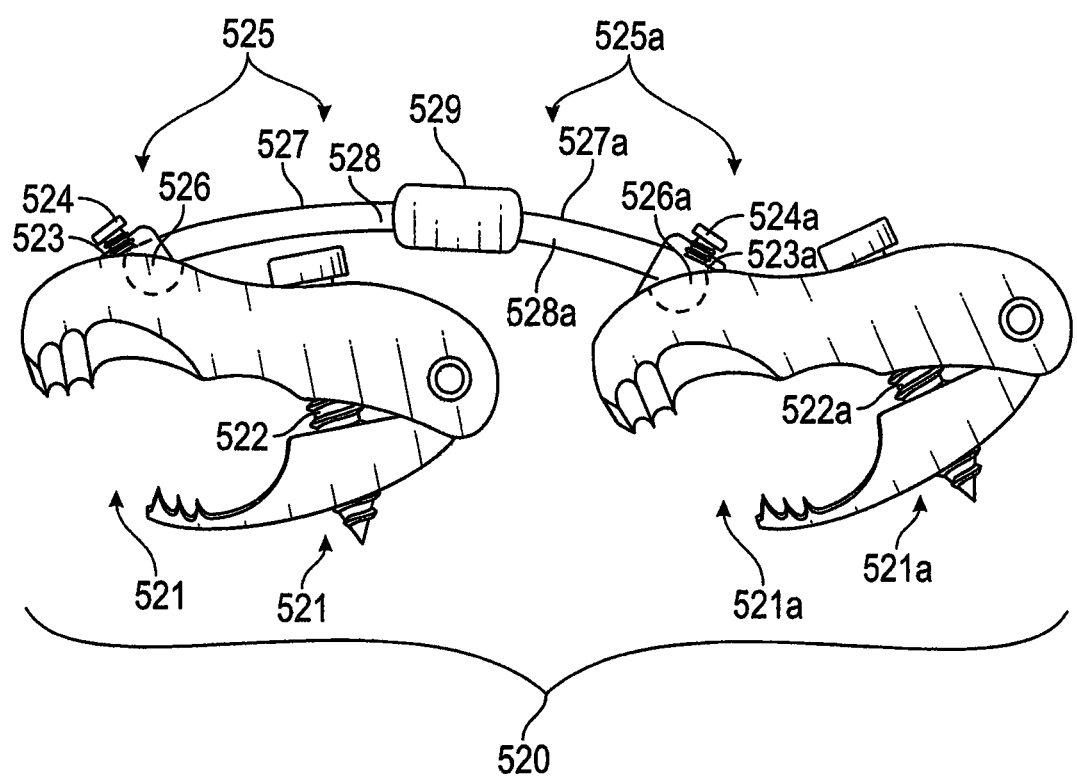
FIG. 37 is a lateral view of a variation of the embodiment examined in FIGS. 36 A, B.
Figure 38:
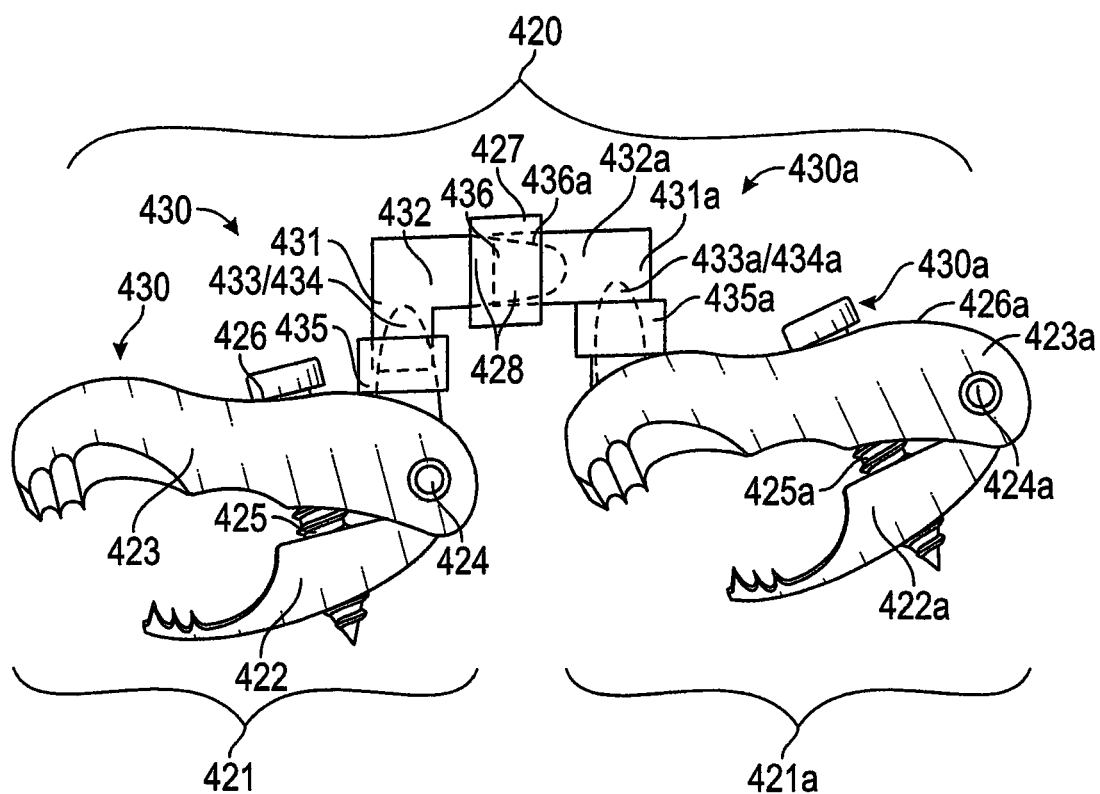

A variation of this embodiment 520 is examined in the lateral perspective in FIG. 37. As demonstrated, there are again cranial and caudal anchors 521, 521a which are actuated by screws 522, 522a to secure against target laminae. However, unlike embodiments disclosed hitherto, this is uniquely characterized inasmuch as there is no distinct connecting element coupling these anchors 521, 521a to stabilize the construct. Rather, each anchor is provided with an elongated, monolithic hemi-connector 525, 525a comprised of an elongated leading end 527, 527a and a spherical trailing end 526, 526a which is seated within a cuffed socket 523, 523a. This arrangement confers polyaxial movement upon the hemi-connector 525. After positioning the anchors 521, 521a, the hemi-connectors are repositioned such that the leadingmost ends 528, 528a approximate each other, hence creating a "modular" connecting element. A coupling element 529 then completes the construct using either threading provided to the element 529 as well as the leadingmost ends 528, 528a, or "cold weld," "pressure fit,"

or any other method known and acceptable to the art. As a final step, screws 524, 524a are tightened against the spheres 525, 525a, preventing rotation.

Figure 38:
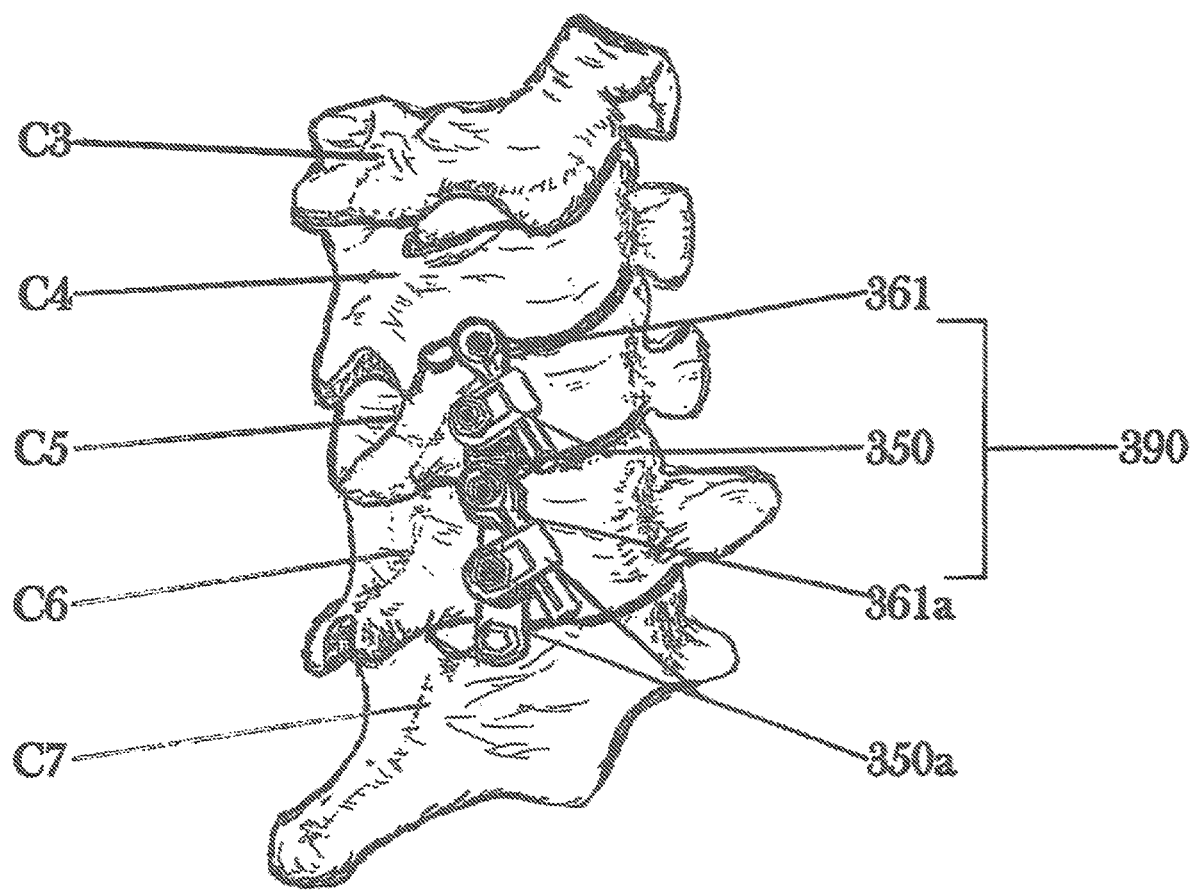
FIG. 38 reveals a lateral view of an alternative embodiment portraying extensions arising from the anchors and coupled by a unique coupling element.

A multi jointed embodiment can be envisioned, with a lateral view of such an embodiment 420 demonstrated in FIG. 38. Here it is noted that the anchors 421, 421a are again provided with sublaminar jaws 422, 422a, dorsal jaws 423, 423a, coupled by axles 424, 424a and actuated by securing screws 425, 425a, being secured against the laminae in the same manner as all anchors previously disclosed in this application. The distinguishing feature which confers upon this a unique, useful, novel and nonobvious method for stabilizing a target motion segment is the manner by which a connecting complex 430 arising from the cranial anchor 421 is coupled to a connecting complex 430a arising from the caudal anchor 421a, each being "mirror images," of the other and directed towards each other, and coupled by a central stabilizing joint 427, hence stabilizing the construct 420.

Each connecting complex 430, 430a is comprised of a vertical segment 431, 431a and a horizontal segment 432, 432a. Projections 433, 433a (superimposed interrupted lines) arise from the dorsal surfaces 426, 426a of the dorsal jaws 423, 423a and fit into chambers 434, 434a within the vertical segments 431, 431a. These junctions are modulated by threaded positioning connectors 435, 435a which interface with threading on the external surfaces of the projections 433, 433a and the vertical segments 431, 431a. These couplings provide the surgeon with the ability to adjust the vertical height of the construct as well as mediolateral rotation, accommodating anatomic variations. The horizontal segments 432, 432a are then coupled with the central stabilizing joint 427. In this illustration, the leading end 436 of the cranial horizontal segment is tapered and passed into a chamber in the leading end 436a of the caudal horizontal extension 432a; the central stabilizing joint 427 is substantially cylindrical, with a threaded central channel 428 (indicated by the diagonally-oriented series of shaded circles), again configured to enmesh with threading on the horizontal segments 432, 432a. The central stabilizing joint 427 can be independently introduced, or can be slidably coupled to one of the horizontal segments and repositioned. In another embodiment, the central stabilizing joint 427 is long enough to couple with the leading ends of both horizontal segments. Regardless of the embodiment, the central stabilizing joint 427 can satisfy the surgeon's requirements in the craniocaudal dimension, i.e. distraction I compression and the construct 420 is complete. Any other means of coupling, including cold welding, pressure fit, the use of a securing screw, and so forth are all within the spirit and scope of the invention. The orthogonal relationship of the vertical and horizontal segments is not an absolute; any angular relationship or any other configuration, including a single arched configuration, is within the spirit and scope of this application.

Figure 39A:
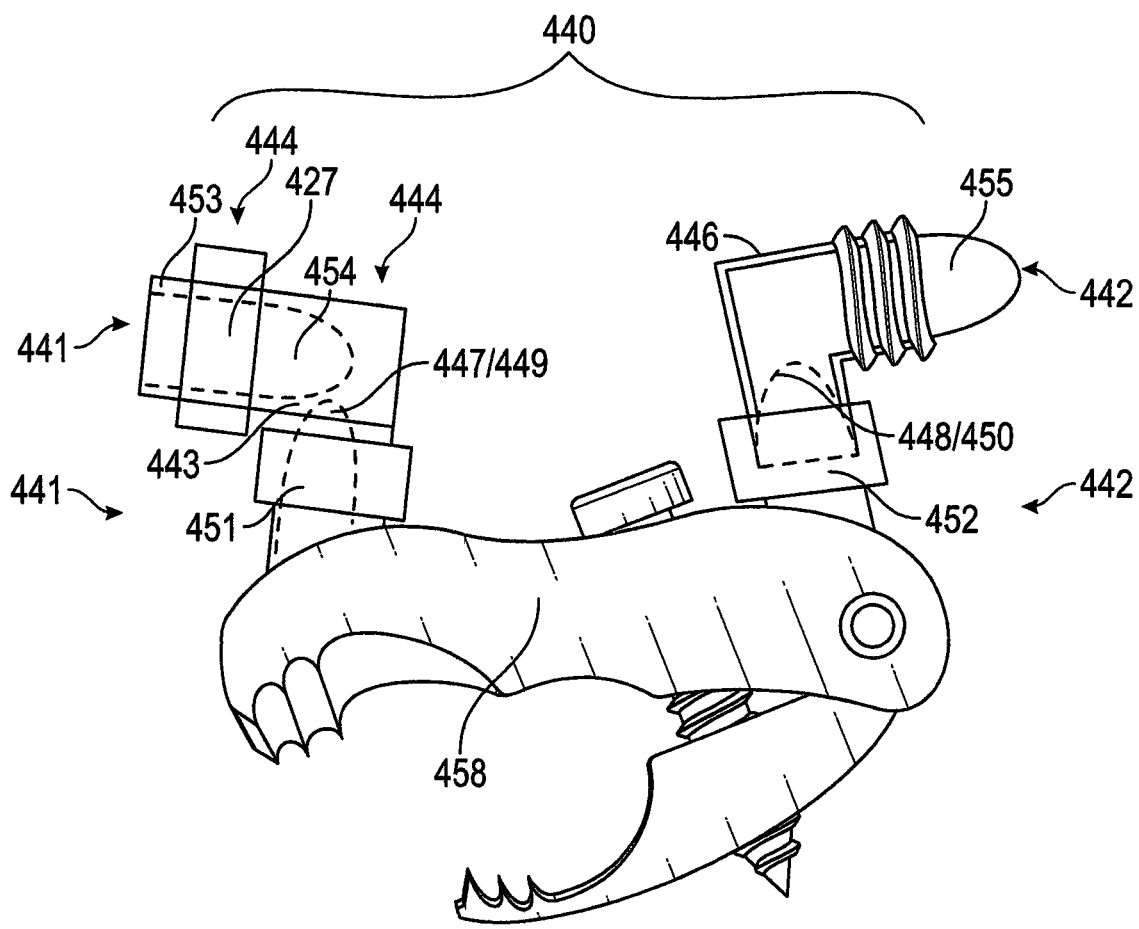
FIG. 39 A displays lateral view of an anchor utilized in a multilevel embodiment of the variation shown in FIG. 38.
Figure 39B:
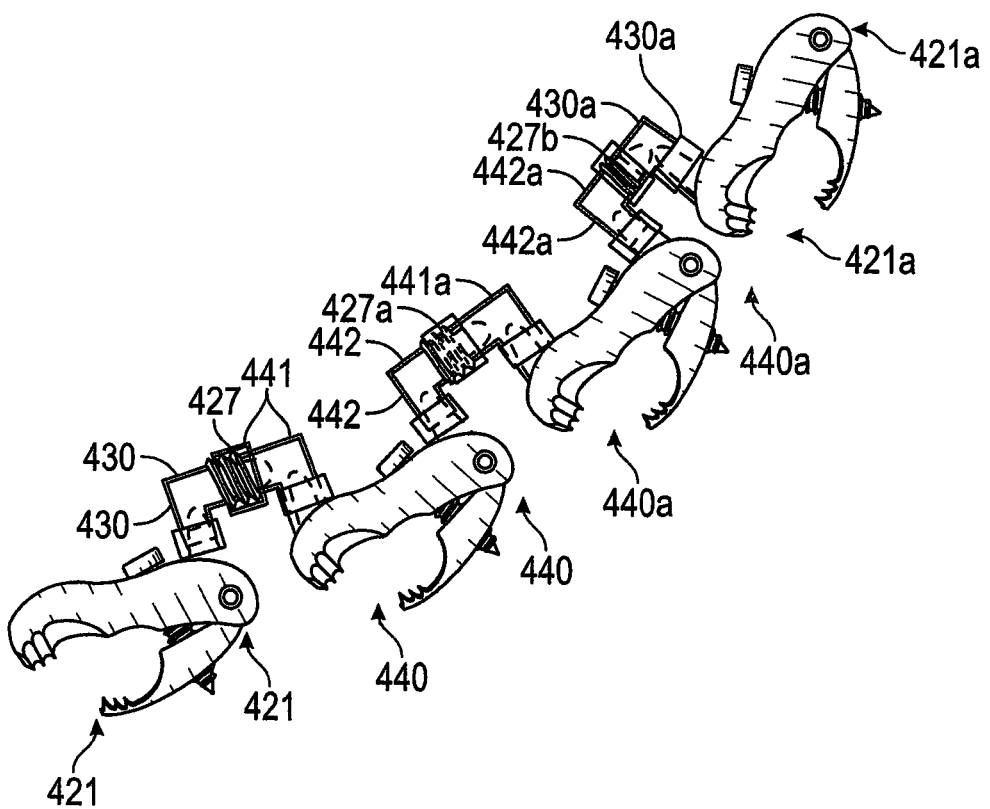

FIGS. 39 A/B reviews a multilevel embodiment of the embodiment displayed in FIG. 38. It is noted that this embodiment provides for an intermediate anchor 440, illustrated in FIG. 39 A, which shows that there is a cranial extension 441 and a caudal extension 442. These are each provided with a vertical segment 443, 444 and a horizontal segment 445, 446; the vertical extensions are provided with chambers 447, 448 which accept dorsal projections 449, 450 arising from the dorsal jaw 458, these junctions governed by positioning connectors 451, 452. The horizontal segments 445, 446 are the points of coupling to adjacent anchors, and are provided with unique components to achieve this. Again, the configurations can vary; in this image, it is noted that the cranial horizontal segment 445 is provided with a chamber 454, wherein the caudal horizontal segment 446 is provided with an extension 455 designed to be disposed into such a chamber; however, these could be reversed, or both segments could be provided with extensions. Also noted is the central stabilizing joint 427, which is in this illustration slidably and irreversibly coupled to the cranial horizontal segment 445. A flange 453 is provided to the leadingmost end of the horizontal segment 445, preventing the joint 427 from slipping off the end. One can envision the mating of this segment with a complimentary segment, with the joint 427 then being slidably repositioned prior to locking the construct. As shown in FIG. 39 B, these anchors 440, 440a couple with each other, as well as the cranial anchor 421 and the caudal anchor 421a using the cranial 430, 441 and caudal 430a, 442 extensions as well as the central stabilizing joints 427, 427a, 427b in the same manner as disclosed above. A construct extending over any number of motion segments can be anticipated.

Figure 40:
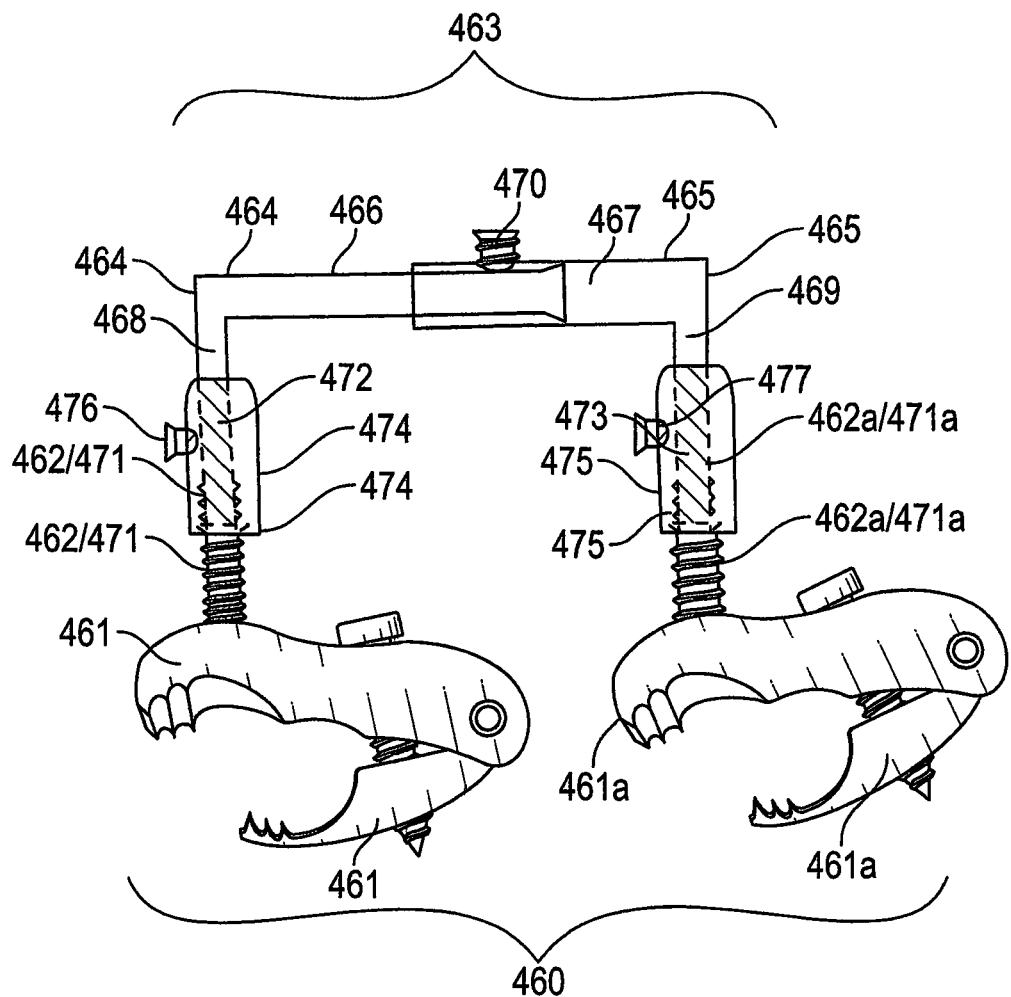
FIG. 40 is a lateral view of another alternative embodiment which is provided with threaded extensions arising from the anchors and a connecting element which is configured to couple with these extensions.

In FIG. 40, an embodiment 460 is seen which is similar is some features to that disclosed in FIGS. 38, 39. This lateral projection shows identical cranial 461 and caudal 461a anchors coupled to a central positioner 463, which is comprised of a cranial element 464 and a caudal element 465. These are comprised of vertical segments 468, 469 and horizontal segments 466, 467, the latter which are slidably coupled by the leading end of one segment (in this case 466) positionably inserted within a chamber of the other, slightly larger leading end. With precise craniocaudal positioning, a locking nut 470 secures the construct 460 in place, again creating a modular connecting element 463. The vertical segments 468, 469 have leading ends 472, 473 which are disposed into vertical couplers 474, 475 (these components of vertical segments denoted by stippling); the couplers are rotatable threaded cylinders 471, 471a configured to enmesh with threading on dorsal projections 462, 462a on the anchors 461, 461a. This configuration of the vertical segments and dorsal projections control the vertical dimension (anatomically, the anteroposterior dimension); additionally, the vertical segments can be rotated along the mediolateral axis, all of which accommodates variations in anatomy. Once the final position is achieved by the surgeon, the central positioner 463 is locked by securing the horizontal locking screw 470 and vertical locking screws 476, 477, thus stabilizing the construct 460 in a unique, useful, novel and nonobvious fashion.

Figure 41:
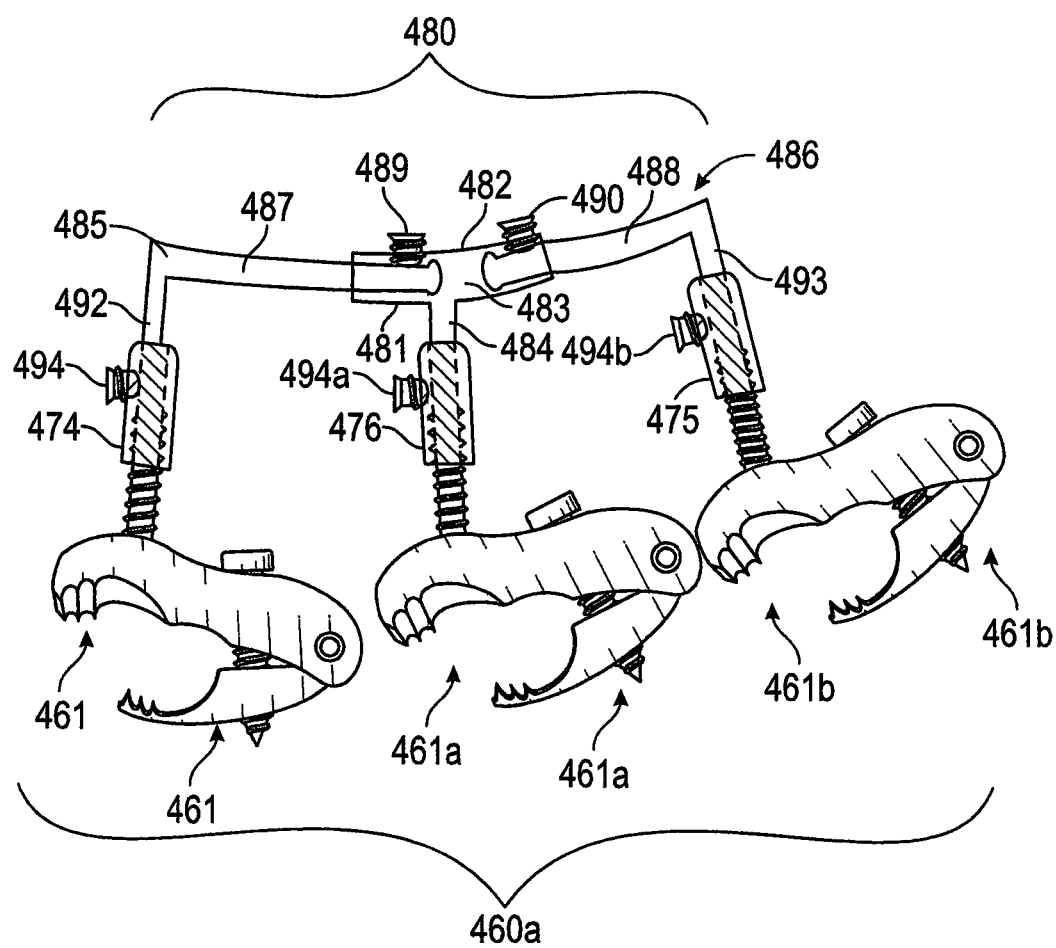
FIG. 41 shows a lateral view of the alternative embodiment in FIG. 40 coupling multiple laminar anchors.

FIG. 41 illustrates a lateral projection of a multilevel construct 460a of the construct depicted in FIG. 40. Again provided is a series of identical anchors 461, 461(a-z); moreover, the embodiment 460a has an expanded central positioner 480 wherein the cranial element 485 and the caudal element 486 of this positioner 480 are coupled with a substantially "T-Shaped," intermediate element 481 provided with a horizontally-oriented segment 482 with a central channel 483 which accepts the leading ends of the horizontal segments 487, 488 of the cranial 485 and caudal 486 elements, these being locked in place by securing screws 489, 490. A vertical component 484 of the intermediate element 481 is solid and monolithic, and is directed into the vertical coupler 476 (the vertical segment within the coupler is denoted by stippling) of the intermediate anchor 461a. Once this is secured by the locking screw 494a, then the horizontal segments 487, 488 are secured after slidably positioning them so that the vertical segments 492, 493 can be disposed into the vertical couplers (stippled within the couplers) 474,475 of the cranial 461 and caudal 461b anchors, locking them with locking screws 494, 494a, 494b, thus completing the construct 460a. It is noted that the horizontal segments 487, 488 are provided with a lordotic curve, which is probably necessary in a multilevel construct. In larger constructs, it is anticipated that an accessory connecting rod that would be positioned between two intermediate elements 481, 481a-z. Presumably, the construct can include as many intermediate anchors and elements as needed, denoted by the subpended letters.

Figure 42:
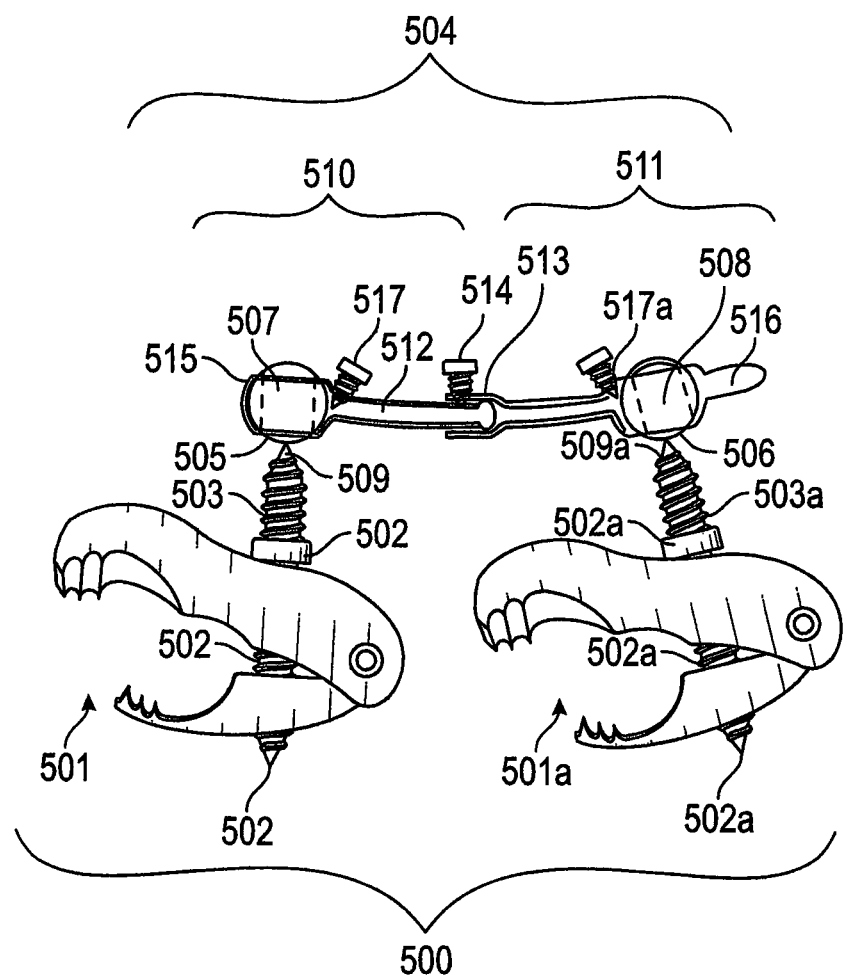
FIG. 42 illustrates a lateral view of a further variation of the embodiment examined in FIG. 40.

A further variation of an embodiment 500 in which threaded dorsal projections arise from the anchors is portrayed in FIG. 42, wherein a lateral view shows substantially standard anchors 501, 501a in which threaded projections 503, 503a extend from the dorsalmost aspect of the securing screw 502, 502a. The unique, useful, novel and nonobvious configuration of a modular connecting element 504 discloses a rod-like element comprised of a cranial 510 and caudal 511 components, with these components slidably coupled such that the free edge 512 of one component (in this example the cranial component 510) is disposed within an expanded central chamber 513 provided to the other component 511, slidably adjusting the craniocaudal dimensions. The components are then locked by the securing screw 514. Each component 510, 511 of the connecting element 504 is provided with a cradle 515, 516 within which spherical couplers 505, 506 are irreversibly retained, providing the couplers with a substantial range of motion. These couplers 505, 506 are provided with threaded chambers 507, 508 (outlined by interrupted lines) which are disposed over the free ends 509, 509a, as indicated by arrows, with the spheres 505, 506 being rotated by a specialized instrument (not shown) until the construct is in place. Securing screws 517, 517a then lock the entire construct 500 in place. One can envision securing nuts being used in addition to, or in lieu of these screws. Multilevel embodiments can of course be anticipated and are within the spirit and scope of the invention.

Figure 43:
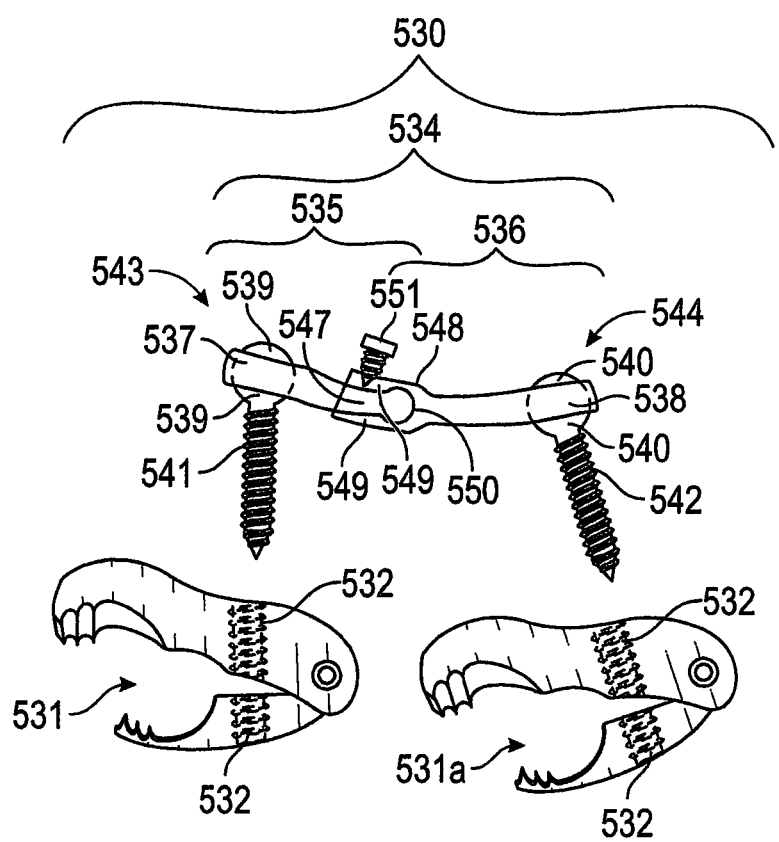
FIG. 43 is a lateral view of an even further variation of an embodiment utilizing threaded extensions to couple the construct.

An even more radical variation of this concept is conceived and shown in FIG. 43, a lateral view of a construct 530 in which the modified anchors 531, 531a do not include securing screws. Instead, the anchors 531, 531a are stabilized against the laminae by a purpose-specific modified implant instrument (not shown) while the unique, useful, novel and nonobvious design of a modular connecting element 534 stabilizes the construct 530. The connecting element 534 is provided with cranial 535 and caudal 536 extensions, each provided with a coupling end 543, 544 which in turn is provided with a cradle 537, 538 which houses an articulating sphere 539, 540. Securing screws 541, 542 are continuous and monolithic with said spheres 539, 540; this configuration confers upon the spheres 539, 540, and hence the screws 541, 542 a significant range of motion. The screws 541, 542 are disposed through tracts 532, 532a within the anchors 531, 531a; this action simultaneously locks the anchors 531, 531a and stabilizes the construct 530. The construct 530 can also be adjusted along the craniocaudal axis. This adjustability results from coupling of the free ends 547, 548 of the extensions 535, 536, wherein the free end of one extension (in this case the caudal extension) is provided with an expanded free end within which a chamber 549 is present which accommodates an expansion 550 at the free end 547 of the cranial extension 535; this expansion assists in locking the extensions. The ends 547, 548 can be slidably repositioned with respect to each other, and hence the craniocaudal adjustability. Once the desired position is achieved, a locking screw 551 secures the connecting element 534 in place.

Figure 44A:
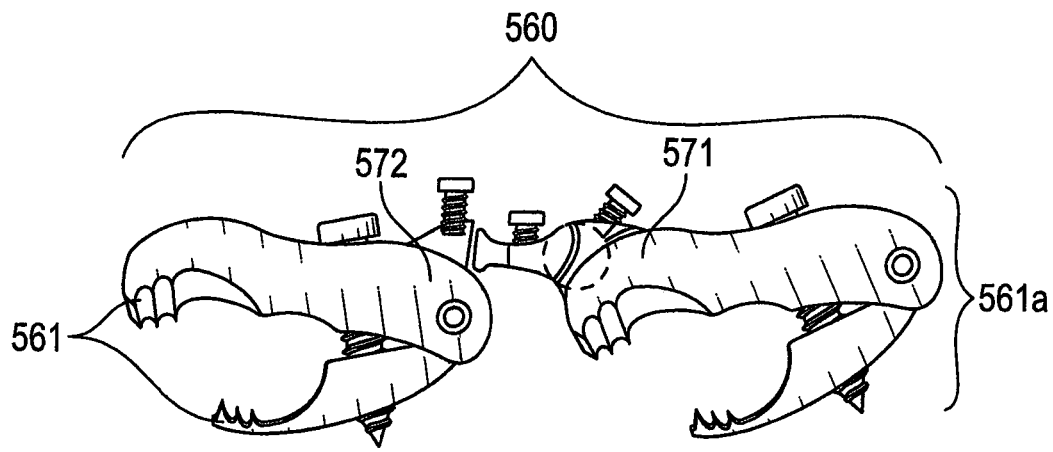
FIGS. 44 A/B reveals a lateral view of an alternative embodiment with a very low profile.
Figure 44B:
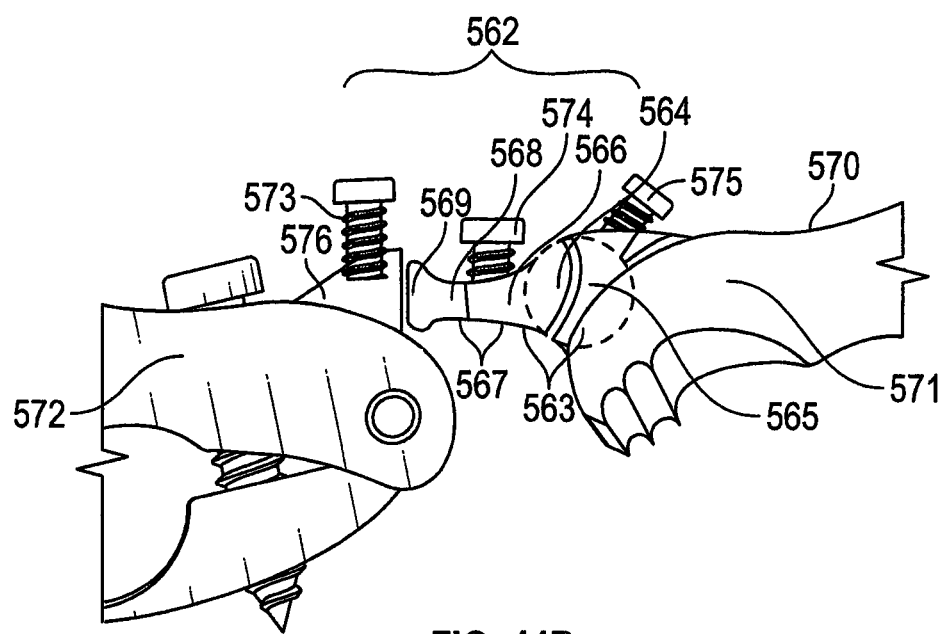

FIG. 44A depicts a lateral view, the best perspective to appreciate the unique feature of an alternative embodiment 560 which is characterized by the lowest anterior-posterior profile of any of the embodiments disclosed in this specification. This is accomplished by disclosing a complex connecting element 562 to uniquely couple with the cranialmost 571 and caudal most 572 aspects of the anchors 561, 561a, said element 562 being best understood by scrutinizing the enlargement in FIG. 44B. This demonstrates that the connecting element 562 is provided with a trailing end 563 and a leading end 567. The trailing end 563 is monolithic but has two aspects, a spherical base 565 which is continuous with a connecting extension 564. The connecting extension 564 itself is provided with a receiving chamber within the free end 566 which accepts and slidably couples than adjustment rod 568 of the leading end 567 of the connecting element 562, adjusting for the craniocaudal dimension, and then locked by the middle securing screw 574. The spherical base 565 is irreversibly retained within a socket 570 that is a component of the cranialmost aspect 571 of the caudal anchor 561a, as seen in both FIGS. 44A, B. This configuration confers a polyaxial range of movement upon the connecting element 562 to accommodate anatomic variations. Once the desired orientation of the connecting element 562 is accomplished, the caudal securing screw 575 is deployed. The leadingmost aspect 569 of the leading end 567 of the connecting element demonstrates an enlargement, which is then disposed into housing chamber 576, and locked with the cranial securing screw 573. While in this portrayal, the spherical end 565 is coupled to the caudal anchor 561a, certainly an embodiment representing a reversal of the configuration can be anticipated and is within the spirit and scope of the invention.

Figure 45:
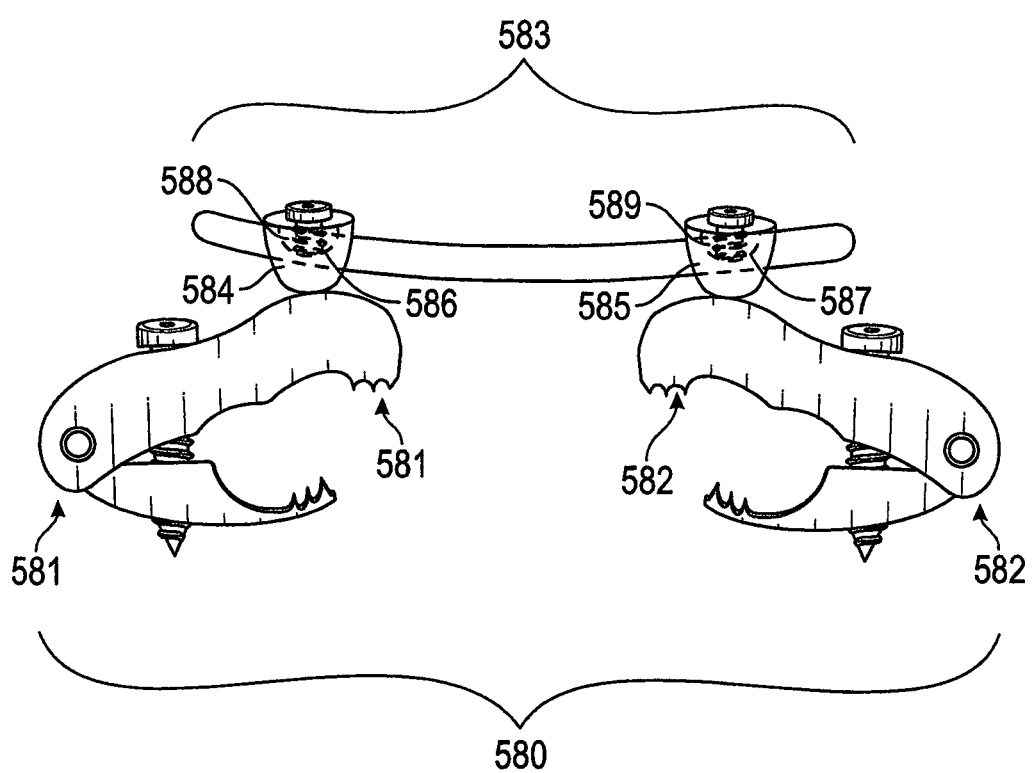
FIG. 45 demonstrates an alternative embodiment in which the jaws anchors are oriented to be confronting each other.

One can continue to envision still other embodiments. In FIG. 45, an alternative embodiment 580 shows one laminar anchor 581 secured to the cranial aspect of the lamina of the cranial vertebra of the target motion segment, which is diametrically contrasted to the typical fashion disclosed in this specification. This anchor 581 is then coupled by a rod-like connecting element 583 to a laminar anchor 582 which is secured to the lamina of the caudal vertebra in the standard fashion disclosed in all embodiments above. Each of these anchors 581, 582 are provided with cradles 584, 585, similar to those disclosed FIGS. 30 A-C. Such as the cradles in those embodiments, the cradles 584, 585 herein are provided with central channels 586, 587, as demonstrated by lines. The bases of these channels 586, 587 are configured to accommodate the connecting element 583; furthermore, the walls of these channels 586, 587 are provided with threading to interface with threading provided to the external surfaces of the securing bolts 588, 589. These bolts 588, 589 are outlined in interrupted lines within the cradles 584, 585, with their trailing ends at the tops of the cradles 584, 585. To complete the construct, the connecting element 583 is positioned within the channels and locked with the securing nuts 588, 589, stabilizing the construct 580.

It is important to recognize that combinations of the embodiments presented above can be envisioned and anticipated, and that any combination of the embodiments presented would be considered within the spirit and scope of this application.

The iterations and embodiments are presented in their general format, but it is recognized that others who read and become knowledgeable regarding the inventions presented herein, and in particular those generally skilled in the art may evolve and demonstrate other embodiments which are obvious when viewed in the face of these disclosures; clearly, all similar embodiments and iterations are within the spirit and scope of the invention.

The foregoing is considered as illustrative only of the principle of the invention. Furthermore, since numerous modifications and changes will readily occur to those skilled in the art, it is not considered desirable to limit the invention to the exact construction and operation shown and described. While the preferred embodiment has been described, the details may be changed without departing from the invention, which will be described by the claims when the subsequent Non-Provisional application is filed.

What is claimed is:

1. A noninvasive system for stabilizing cervical vertebrae comprising: A first non-invasive bone clamp with a dorsal jaw; a sublaminar jaw; an articulating axle and a screw wherein said sublaminar jaw has a first leading end and a second anterior end said sublaminar first leading end has a relatively thin plate portion; and an axle for pivotally coupling said sublaminar jaw and said dorsal jaw; and means locking nut for a securing said screw said threaded activation piece actuator that connects to said sublaminar jaw and said dorsal jaw through threaded tracts; and, a second non-invasive bone clamp with a sublaminar jaw and a dorsal jaw, an axle that pivotally connects said sublaminar jaw and said dorsal jaw; and a connecting element which connects said first non-invasive bone clamp to said second non-invasive bone clamp.

2. The non-invasive system for stabilizing cervical vertebrae of claim 1 wherein said sublaminar jaws of said first nonintrusive bone clamp and said sublaminar jaw of said second nonintrusive bone clamp are substantially hemi-ovoid in configuration and have at least one rounded tooth at the anterior end portion and hold a cervical vertebral lamina between said sublaminar jaw and said dorsal jaw by providing contact pressure at an axis diagonal to the lamina when said anchor is deployed.

3. The non-invasive system for stabilizing cervical vertebrae of claim 2 wherein said dorsal jaw of said first nonintrusive bone clamp and said dorsal jaw of said second nonintrusive second bone clamps are substantially hemi-ovoid in configuration and are connectable together on a superior end of said screw with said connecting element.

4. The non-invasive system of claim 3 wherein said connector element comprises a rod with a first end and a second end; a pivotally attached adaptor disposed on said first end that is attachably connected to the main body of said dorsal jaw body.

5. A non-invasive bone anchor for stabilizing cervical vertebrae comprising: a dorsal jaw with a main body and a threaded tract to carry a screw; a sublaminar jaw; an articulating axle that pivotally connects said sublaminar jaw and said dorsal jaw; a connector element disposed in the main body of said dorsal jaw and wherein said sublaminar jaw has a first leading end and a second anterior end said sublaminar first leading end has a relatively thin plate portion; and wherein said dorsal jaw comprising an articulating axle coupling said sublaminar jaw and said dorsal jaw; and said screw connects to said sublaminar jaw through a threaded groove and wherein said dorsal jaw has a main body attached to the connector element.

6. The non-invasive bone anchor for stabilizing cervical vertebrae of claim 5 wherein said dorsal jaws of said first and second bone clamps are substantially hemi-ovoid in configuration and are connectable together on a superior end of said main body of said dorsal jaw with said connector element.

7. A noninvasive system for stabilizing cervical vertebrae comprising: a first non-invasive bone clamp comprising;
- a dorsal jaw with a main body with a threaded tract; a sublaminar jaw; an axle pivotally connecting said sublaminar jaw and said dorsal jaw and a screw wherein said sublaminar jaw has a first leading end and a second anterior end, said sublaminar first leading end has a relatively thin plate portion; and said dorsal jaw has a threaded groove where said screw couples with said sublaminar jaw and said dorsal jaw; and said screw connects to said sublaminar jaw through a threaded groove and said dorsal jaw through said threaded track;
- a second non-invasive bone clamp; and a connecting element which connects said first non-invasive bone clamp to said second non-invasive bone clamp, and wherein said sublaminar jaw and said dorsal jaw when drawn together by said screw sit at an angle to the lamina when positioned as anchor; and
- a connecting element having a shaft-like central portion and a cranial end and a trailing end, wherein said cranial end and said first end attaches main body of said first bone anchor and said trailing end attaches to main body of dorsal jaw of the second bone anchor.

* * * * *